US007034015B2

(12) United States Patent
Ottosen et al.

(10) Patent No.: US 7,034,015 B2
(45) Date of Patent: Apr. 25, 2006

(54) AMINOBENZOEPHENONES

(75) Inventors: Erik Rytter Ottosen, Ølstykke (DK); Anne Marie Horneman, Humlebæk (DK); Xifu Liang, Frederiksberg (DK)

(73) Assignee: Leo Pharma A/S, Ballerup (DK)

( * ) Notice: Subject to any disclaimer, the term of this patent is extended or adjusted under 35 U.S.C. 154(b) by 0 days.

(21) Appl. No.: 10/228,954

(22) Filed: Aug. 28, 2002

(65) Prior Publication Data

US 2003/0119902 A1    Jun. 26, 2003

Related U.S. Application Data

(60) Provisional application No. 60/315,025, filed on Aug. 28, 2001.

(30) Foreign Application Priority Data

Feb. 8, 2002    (DK) ............................ 2002 00189

(51) Int. Cl.
  *A61K 31/277*    (2006.01)
  *A61K 31/221*    (2006.01)
  *A61K 31/165*    (2006.01)
  *A61K 31/135*    (2006.01)
  *A61K 31/15*     (2006.01)

(52) U.S. Cl. .................. 514/114; 514/119; 514/230.8; 514/237.8; 514/255.04; 514/328; 514/331; 514/369; 514/376; 514/389; 514/390; 514/417; 514/424; 514/425; 514/456; 514/459; 514/460; 514/465; 514/467; 514/471; 514/478; 514/479; 514/518; 514/533; 514/534; 514/535; 514/536; 514/537; 514/546; 514/547; 514/548; 514/549; 514/567; 514/580; 514/595; 514/616; 514/630; 514/648; 514/709; 544/162; 544/165; 544/173; 544/397; 546/220; 546/232; 548/183; 548/317.1; 548/317.5; 548/319.5; 548/226; 548/451; 548/481; 548/543; 548/545; 548/546; 549/396; 549/419; 549/435; 549/451; 549/476; 549/491; 549/496; 558/48; 558/166; 558/167; 558/275; 560/12; 560/16; 560/27; 560/34; 560/38; 560/39; 560/43; 560/45; 560/47; 560/169; 560/179; 560/250; 560/251; 560/255; 562/441; 564/15; 564/27; 564/47; 564/97; 564/150; 564/157; 564/158; 564/175; 564/200; 564/323; 564/326; 564/328

(58) Field of Classification Search .................. 564/328
  See application file for complete search history.

(56) References Cited

FOREIGN PATENT DOCUMENTS

| | | |
|---|---|---|
| JP | 57-177058 | 10/1982 |
| WO | WO 98/32730 A1 | 7/1998 |
| WO | WO 01/05744 A1 | 1/2001 |
| WO | WO 01/05745 A1 | 1/2001 |
| WO | WO 01/05746 A1 | 1/2001 |
| WO | WO 01/05749 A1 | 1/2001 |
| WO | WO 01/05751 A1 | 1/2001 |
| WO | WO 01/42189 A1 | 6/2001 |

OTHER PUBLICATIONS

Database CAPLUS on STN, Acc. No. 2001:435023, WO 2001042189, Jun. 14, 2001 (abstract).*
Database CAPLUS on STN, Acc. No. 1998:527309, Ottosen et al., WO 9832730, Jul. 30, 1998 (abstract).*
Database CAPLUS on STN, Acc. No. 2001:63956, Ottosen, WO 2001005746 Jan. 25, 2001 (abstract).*
Hussein et al., *Iraqi J. Sci.*, vol. 22, No. 1, pp. 54-66, 1981.
Bhavsar et al., *Man-Made Textiles in India*, vol. 30, No. 6, pp. 275-276, Jun., 1987.
Bhavsar et al., *Man-Made Textiles in India*, vol. 29, No. 5, pp. 224-230, May, 1986.
Bhavsar et al., *Man-Made Textiles in India*, vol. 28, No. 11, pp. 425, 427-431, Nov., 1985.

* cited by examiner

*Primary Examiner*—Brian Davis
(74) *Attorney, Agent, or Firm*—Birch, Stewart, Kolasch & Birch, LLP

(57) ABSTRACT

The invention relates to a novel class of aminobenzophenones derivatives, to pharmaceutical preparations comprising said compounds, to dosage units of such preparations, to methods of treating patients comprising administering said compounds, and to the use of said compounds in the manufacture of pharmaceutical preparations.

22 Claims, No Drawings

AMINOBENZOEPHENONES

This application claims priority on provisional Application No. 60/315,025 filed on Aug. 28, 2001, the entire contents of which are hereby incorporated by reference.

FIELD OF THE INVENTION

The invention relates to a novel class of compounds, namely aminobenzophenone derivatives, to pharmaceutical preparations comprising said compounds, to dosage units of such preparations, to methods of treating patients comprising administering said compounds, and to the use of said compounds in the manufacture of pharmaceutical preparations.

BACKGROUND OF THE INVENTION

Previously, a series of closely related aminobenzophenones (e.g. 4-(2-amino-4-nitrophenylamino)benzophenone) have been described (Hussein, F. A. et al, Iraqi J. Sci., 22, 54–66 (1981). However, there is no description of their uses. WO 98/32730, WO 01/05744, WO 01/05746, WO01/05749, WO 01/05751, WO 01/05745 and WO 01/42189 disclose aminobenzophenone inhibitors of interleukin 1β (IL-1β) and tumour necrosis factor α (TNF-α) secretion in vitro, said compounds being potentially useful for treatment of inflammatory diseases in which the production of cytokines is involved in the pathogenesis, e.g. asthma, rheumatoid arthritis, psoriasis, contact dermatitis and atopic dermatitis.

Furthermore, the compounds of the above mentioned patent applications were tested in vivo for anti-inflammatory properties in the 12-O-tetradecanoylphorbol-13-acetate (TPA) induced murine chronic skin inflammation model, (De Young, L. M. et al., Agents Actions, 26, 335–341 (1989); Carlson, R. P. et al., Agents Actions, 17, 197–204 (1985); Alford, J. G. et al., Agents Action, 37, (1992);
Stanley, P. L. et al., Skin Pharmacol, 4, 262–271 (1991). In this chronic skin inflammation model the compounds had a potency similar to the reference compound hydrocortisone.

The preparation of structurally related aminobenzophenones useful as dyes for textiles is disclosed in Man-Made Text. India (1987), 30(6), 275–6, Man-Made Text. India (1986), 29(5), 224–30, and Man-Made Text. India (1985), 28(11), 425, 427–9, 431; and a structurally related aminobenzophenone is disclosed in JP 81–61259 as a reactant in the preparation of fluoran dye precursors.

The purpose of the present invention is to provide further pharmacologically active benzophenone derivatives with superior physico-chemical properties, in particular with improved bioavailability.

SUMMARY OF THE INVENTION

It has surprisingly been found that novel aminobenzophenone derivatives according to the general formula I are potent inhibitors of interleukin 1β(IL-1β) and tumour necrosis factor α (TNF-α) secretion in vitro, making them potentially useful for treatment of inflammatory diseases, in which the secretion and regulation of cytokines or more specifically interleukin 1β (IL-1β) and tumour necrosis factor α (TNF-α) are involved in the pathogenesis. The inhibition or down regulation of the cytokines is possibly due to an inhibition of MAP kinases. Accordingly, the invention relates to compounds of the general formula I

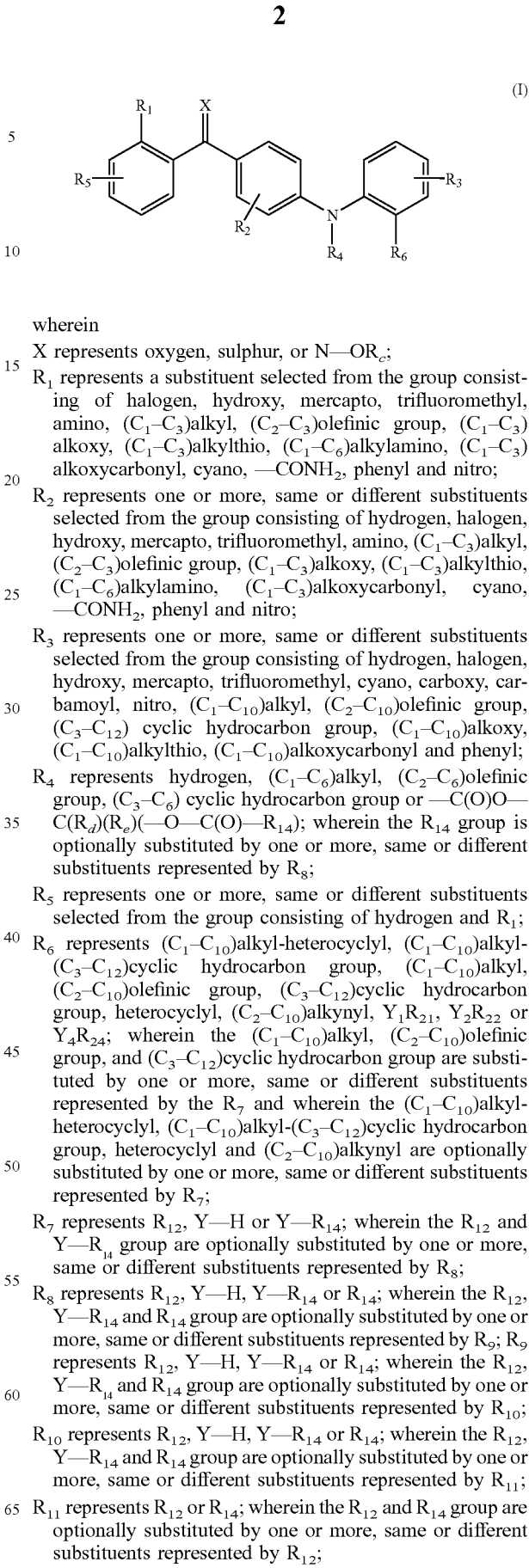

wherein
X represents oxygen, sulphur, or N—$OR_c$;
$R_1$ represents a substituent selected from the group consisting of halogen, hydroxy, mercapto, trifluoromethyl, amino, ($C_1$–$C_3$)alkyl, ($C_2$–$C_3$)olefinic group, ($C_1$–$C_3$) alkoxy, ($C_1$–$C_3$)alkylthio, ($C_1$–$C_6$)alkylamino, ($C_1$–$C_3$) alkoxycarbonyl, cyano, —$CONH_2$, phenyl and nitro;
$R_2$ represents one or more, same or different substituents selected from the group consisting of hydrogen, halogen, hydroxy, mercapto, trifluoromethyl, amino, ($C_1$–$C_3$)alkyl, ($C_2$–$C_3$)olefinic group, ($C_1$–$C_3$)alkoxy, ($C_1$–$C_3$)alkylthio, ($C_1$–$C_6$)alkylamino, ($C_1$–$C_3$)alkoxycarbonyl, cyano, —$CONH_2$, phenyl and nitro;
$R_3$ represents one or more, same or different substituents selected from the group consisting of hydrogen, halogen, hydroxy, mercapto, trifluoromethyl, cyano, carboxy, carbamoyl, nitro, ($C_1$–$C_{10}$)alkyl, ($C_2$–$C_{10}$)olefinic group, ($C_3$–$C_{12}$) cyclic hydrocarbon group, ($C_1$–$C_{10}$)alkoxy, ($C_1$–$C_{10}$)alkylthio, ($C_1$–$C_{10}$)alkoxycarbonyl and phenyl;
$R_4$ represents hydrogen, ($C_1$–$C_6$)alkyl, ($C_2$–$C_6$)olefinic group, ($C_3$–$C_6$) cyclic hydrocarbon group or —C(O)O—$C(R_d)(R_e)$(—O—C(O)—$R_{14}$); wherein the $R_{14}$ group is optionally substituted by one or more, same or different substituents represented by $R_8$;
$R_5$ represents one or more, same or different substituents selected from the group consisting of hydrogen and $R_1$;
$R_6$ represents ($C_1$–$C_{10}$)alkyl-heterocyclyl, ($C_1$–$C_{10}$)alkyl-($C_3$–$C_{12}$)cyclic hydrocarbon group, ($C_1$–$C_{10}$)alkyl, ($C_2$–$C_{10}$)olefinic group, ($C_3$–$C_{12}$)cyclic hydrocarbon group, heterocyclyl, ($C_2$–$C_{10}$)alkynyl, $Y_1R_{21}$, $Y_2R_{22}$ or $Y_4R_{24}$; wherein the ($C_1$–$C_{10}$)alkyl, ($C_2$–$C_{10}$)olefinic group, and ($C_3$–$C_{12}$)cyclic hydrocarbon group are substituted by one or more, same or different substituents represented by the $R_7$ and wherein the ($C_1$–$C_{10}$)alkyl-heterocyclyl, ($C_1$–$C_{10}$)alkyl-($C_3$–$C_{12}$)cyclic hydrocarbon group, heterocyclyl and ($C_2$–$C_{10}$)alkynyl are optionally substituted by one or more, same or different substituents represented by $R_7$;
$R_7$ represents $R_{12}$, Y—H or Y—$R_{14}$; wherein the $R_{12}$ and Y—$R_{14}$ group are optionally substituted by one or more, same or different substituents represented by $R_8$;
$R_8$ represents $R_{12}$, Y—H, Y—$R_{14}$ or $R_{14}$; wherein the $R_{12}$, Y—$R_{14}$ and $R_{14}$ group are optionally substituted by one or more, same or different substituents represented by $R_9$; $R_9$ represents $R_{12}$, Y—H, Y—$R_{14}$ or $R_{14}$; wherein the $R_{12}$, Y—$R_{14}$ and $R_{14}$ group are optionally substituted by one or more, same or different substituents represented by $R_{10}$;
$R_{10}$ represents $R_{12}$, Y—H, Y—$R_{14}$ or $R_{14}$; wherein the $R_{12}$, Y—$R_{14}$ and $R_{14}$ group are optionally substituted by one or more, same or different substituents represented by $R_{11}$;
$R_{11}$ represents $R_{12}$ or $R_{14}$; wherein the $R_{12}$ and $R_{14}$ group are optionally substituted by one or more, same or different substituents represented by $R_{12}$;

$R_{12}$ represents halogen, hydroxy, mercapto, trifluoromethyl, amino, $(C_1–C_3)$alkoxy, $(C_1–C_3)$alkylthio, $(C_1–C_6)$alkylamino, $(C_1–C_3)$alkoxycarbonyl, $(C_1–C_9)$trialkylammonium in association with an anion, $(C_2–C_{10})$dialkylphosphinoyl, $(C_1–C_5)$alkyl(hydroxy)phosphinoyl, $(C_2–C_{10})$dialkylphosphinoyloxy, $(C_1–C_5)$alkyl(hydroxy)phosphinoyloxy, dihydroxyphosphinoyl, dihydroxyphosphinoyloxy, cyano, azido, nitro, —CHO, —COOH, —CONH$_2$, —CONHR', or —CONRR' wherein R and R' represent $(C_1–C_3)$alkyl;

Y represents —O—, —S—, —S(O)—, —S(O)$_2$—, —NR$_a$—, —NR$_a$C(Z)NR$_b$—, —NR$_a$C(Z)—, —C(Z)NR$_a$—, —C(O)—, —C(S)—, —C(Z)O—, —C(O)Z—, —C(S)S— —OC(Z)—, —NR$_a$C(Z)O—, —OC(Z)NR$_a$—, —S(O)$_2$O—, —OS(O)$_2$—, —S(O)$_2$NR$_a$—, —NR$_a$S(O)$_2$—, —OC(Z)O—, —OC(Z)Z—, —OP(O)(OR$_a$)O—, —P(O)(OR$_a$)O—, —C(NR$_a$)—, —C(NOR$_a$)—, N=C(R$_a$)—, —N=C(OR$_a$)—, —N(OR$_a$)—, —ON(R$_a$)—, —N(R$_a$)O—, —N(R$_a$)C(=NR$_b$)NRC—, —C(=NR$_a$)NR$_b$— or —N(R$_a$)C(=NR$_b$)—;

Z represents oxygen or sulphur;

$R_{14}$ represents $(C_1–C_6)$alkyl, $(C_2–C_6)$olefinic group, $(C_3–C_{12})$cyclic hydrocarbon group, heterocyclyl or $(C_2–C_6)$alkynyl;

$Y_1$ represents —NR$_a$C(S)NR$_b$—, —C(O)—, —C(S)—, —C(S)O—, —C(O)S—, —C(S)S— —OC(S)—, —OC(O)—, —NR$_a$C(S)O—, —OC(Z)NR$_a$—, —S(O)$_2$O—, —OS(O)$_2$—, —S(O)$_2$NR$_a$—, —NR$_a$S(O)$_2$—, —OC(Z)O—, —OC(Z)Z—, —OP(O)(OR$_a$)O—, —P(O)(OR$_a$)O—, —C(NR$_a$)—, —C(NOR$_a$)—, —N=C(R$_a$)—, —N=C(OR$_a$)—, —N(OR$_a$)—, —ON(R$_a$)—, —N(R$_a$)O—, —N(R$_a$)C(=NR$_b$)NRC—, —C(=NR$_a$)NR$_b$— or —N(R$_a$)C(=NR$_b$)—;

$R_{21}$ represents $(C_1–C_{10})$alkyl-heterocyclyl, $(C_1–C_{10})$alkyl-$(C_3–C_{12})$cyclic hydrocarbon group, $(C_1–C_{10})$alkyl, $(C_2–C_{10})$olefinic group, $(C_3–C_{12})$cyclic hydrocarbon group, heterocyclyl or $(C_2–C_{10})$alkynyl; any of which are optionally substituted by one or more, same or different substituents represented by $R_7$;

$Y_2$ represents —O—, —S—, —C(O)O— or —C(O)NR$_a$—;

$R_{22}$ represents $(C_1–C_{10})$alkyl-heterocyclyl, $(C_1–C_{10})$alkyl-$(C_3–C_{12})$cyclic hydrocarbon group, heterocyclyl, $(C_2–C_{10})$alkynyl, $(C_1–C_{10})$alkyl, $(C_2–C_{10})$olefinic group or $(C_3–C_{12})$monocyclic hydrocarbon group; wherein the $(C_1–C_{10})$alkyl is substituted by one or more, same or different substituents represented by $R_7$ and wherein the $(C_1–C_{10})$alkyl-heterocyclyl, $(C_1–C_{10})$alkyl-$(C_3–C_{12})$cyclic hydrocarbon group, heterocyclyl, $(C_2–C_{10})$alkynyl, $(C_2–C_{10})$olefinic group, and $(C_3–C_{12})$monocyclic hydrocarbon group are optionally substituted by one or more, same or different substituents represented by $R_7$;

$Y_4$ stands for —NR$_a$C(O)NR$_b$CH(R$_c$)—, —NR$_a$C(O)NR$_b$S(O)$_2$—, —NR$_a$—, —NR$_a$C(Z)—, —NR$_a$C(O)OCH(R$_c$)—, —NR$_a$C(O)NR$_b$C(R$_d$)(R$_e$)—OC(O)— or —NR$_a$C(O)OC(R$_d$)(R$_e$)—OC(O)—;

$R_{24}$ represents $(C_1–C_{10})$alkyl-heterocyclyl, $(C_1–C_{10})$alkyl-$(C_3–C_{12})$cyclic hydrocarbon group, heterocyclyl, $(C_2–C_{10})$alkynyl, $(C_1–C_{10})$alkyl, $(C_2–C_{10})$olefinic group or $(C_3–C_{12})$cyclic hydrocarbon group; wherein the $(C_1–C_{10})$alkyl, $(C_2–C_{10})$olefinic group and $(C_3–C_{12})$cyclic hydrocarbon group are substituted by one or more, same or different substituents represented by $R_{15}$, and wherein the $(C_1–C_{10})$alkyl, $(C_2–C_{10})$olefinic group, $(C_3–C_{12})$cyclic hydrocarbon group, $(C_1–C_{10})$alkyl-heterocyclyl, $(C_1–C_{10})$alkyl-$(C_3–C_{12})$cyclic hydrocarbon group, heterocyclyl and $(C_2–C_{10})$alkynyl are optionally substituted by one or more, same or different substituents represented by $R_7$;

$R_{15}$ represents $R_{12a}$, $R_{12b}$ or $R_{12c}$; wherein $R_{12a}$, $R_{12b}$ and $R_{12c}$ are optionally substituted by one or more, same or different substituents represented by $R_7$;

$R_{12a}$ represents $(C_1–C_3)$alkoxy, $(C_1–C_3)$alkylthio, $(C_1–C_6)$alkylamino, $(C_1–C_3)$alkoxycarbonyl, —CONHR' or —CONRR' wherein R and R' represents $(C_1–C_3)$alkyl; any of which are substituted by one or more, same or different substituents represented by $R_{42}$; with the proviso that when $R_{12a}$ or $R_{15}$, including further substitution by $R_{42}$, represent groups of the formulas —(Q—O)$_n$—Q or —CH$_2$(Q—O)$_n$—Q, where Q is a $(C_1–C_3)$alkyl and n is an integer larger than 1, then said groups comprise a continuous linear sequence of atoms with at least 16 atoms;

$R_{12b}$ represents $(C_4–C_{10})$alkoxy, $(C_4–C_{10})$alkylthio, $(C_7–C_{12})$alkylamino, $(C_4–C_{10})$alkoxycarbonyl, —CONHR' or —CONRR' wherein R and R' represent $(C_4–C_{10})$alkyl; any of which are optionally substituted by one or more, same or different substituents represented by $R_7$;

$R_{12c}$ represents —Y$_5$$(C_1–C_{10})$alkyl, —Y-aryl, —Y-heterocyclyl, —Y—$(C_3–C_{12})$cyclic hydrocarbon group and —Y—$(C_2–C_{10})$olefinic group; any of which are optionally substituted by one or more, same or different substituents represented by $R_7$;

$Y_5$ stands for —S(O)—, —S(O)$_2$—, —NR$_a$C(Z)—, —NR$_a$C(Z)NR$_b$—, —C(S)NR$_a$—, —C(O)—, —C(S)—, —C(S)O—, —C(O)S—, —C(S)S— —OC(Z)—, —NR$_a$C(Z)O—, —OC(Z)NR$_a$—, —S(O)$_2$O—, —OS(O)$_2$—, —S(O)$_2$NR$_a$—, NR$_a$S(O)$_2$—, —OC(Z)O—, —OC(Z)Z—, —OP(O)(OR$_a$)O—, —P(O)(OR$_a$)O—, —C(NR$_a$)—, —C(NOR$_a$)—, —N=C(R$_a$)—, —N=C(OR$_a$)—, —N(OR$_a$)—, ON(R$_a$)—, —N(R$_a$)O—, N(R$_a$)C(=NR$_b$)NR$_c$—, —C(=NR$_a$)NR$_b$— or —N(R$_a$)C(=NR$_b$)—;

$R_{42}$ represents —Y—H, Y—$R_{14}$, $R_{52}$, halogen, trifluoromethyl, cyano, azido or nitro; wherein $R_{52}$ and —Y—$R_{14}$ are optionally substituted by one or more, same or different substituents represented by $R_8$;

$R_{52}$ represents $(C_6–C_{10})$alkyl, $(C_2–C_6)$olefinic group, $(C_3–C_{12})$cyclic hydrocarbon group, heterocyclyl, $(C_2–C_6)$alkynyl or heteroaryl;

$R_a$, $R_b$ and $R_c$ represent independently hydrogen, $(C_1–C_6)$alkyl, $(C_2–C_6)$olefinic group, $(C_3–C_{12})$cyclic hydrocarbon group, aryl, heterocyclyl or $(C_2–C_6)$alkynyl; any of which are optionally substituted by one or more, same or different substituents represented by $R_{12}$;

$R_d$ and $R_e$ represent independently hydrogen, $(C_1–C_6)$alkyl, $(C_2–C_6)$olefinic group and $(C_3–C_{12})$cyclic hydrocarbon group; any of which are optionally substituted by one or more, same or different substituents represented by $R_{12}$;

and pharmaceutically acceptable salts, solvates, e.g. hydrate thereof.

In a still further aspect, the invention relates to a pharmaceutical preparation comprising a compound of formula I or a pharmaceutically acceptable salt thereof, optionally together with a pharmaceutically acceptable excipient or vehicle.

In a still further aspect, the invention relates to a method of treating inflammation in patients, the method comprising administering to said patients an effective amount of a compound of formula I.

In a still further aspect, the invention relates to the use of a compound of formula I, optionally together with a pharmaceutically acceptable excipient or vehicle in the manufacture of a medicament for the treatment of inflammation.

DETAILED DESCRIPTION OF THE INVENTION

It is a well known and common experience in the course of many, if not most, drug developments that candidates, which appear promising during the in vitro screening phase fail to deliver any therapeutic effect when tested in vivo. There may be several explanations to such observations, e.g. rapid drug metabolism or insufficient plasma stability, but very often the cause is insufficient bioavailability. Bioavailability of a drug is controlled by several factors broadly referred to as the physico-chemical characteristics. Physico-chemical characteristics pivotal to bioavailability are e.g. water solubility and log P, defined as $$\log \frac{\text{Solubility in octane}}{\text{Solubility in water}}.$$

A log P value between 1 and 5 will endow most drugs with the optimal bioavailability. Accordingly, any drug development programme will benefit if it succeeds in identifying one or more groups in a molecular structure, which can be substituted, without compromising the biological activity, to manipulate the physico-chemical characteristics, and thus the bioavailability. The present inventors have surprisingly found that the substituent represented by $R_6$ can be manipulated, while largely maintaining the biological activity of the compounds of formula I, to control the physico-chemical characteristics of said compounds.

Accordingly, preferred compounds of the present invention are those wherein $R_1$ represents a substituent selected from the group consisting of halogen, hydroxy, trifluoromethyl, amino, $(C_1-C_3)$alkyl, $(C_2-C_3)$olefinic group, $(C_1-C_3)$alkoxy and cyano.

In another preferred embodiment, $R_2$ represents one or more substituents independently selected from the group of hydrogen, halogen, hydroxy, trifluoromethyl, $(C_1-C_3)$alkyl, $(C_2-C_3)$olefinic group and $(C_1-C_3)$alkoxy.

In another preferred embodiment, $R_3$ represents one or more substituents independently selected from the group consisting of hydrogen, halogen, hydroxy, trifluoromethyl, cyano, nitro, $(C_1-C_6)$alkyl, $(C_2-C_6)$olefinic group, $(C_3-C_6)$ monocyclic hydrocarbon group, $(C_1-C_6)$alkoxy and $(C_1-C_6)$alkoxycarbonyl.

In another preferred embodiment, $R_4$ represents hydrogen, $(C_1-C_6)$alkyl or $(C_2-C_6)$olefinic group.

In another preferred embodiment, $R_5$ represents one or more substituents independently selected from the group consisting of hydrogen and halogen, hydroxy, trifluoromethyl, amino, $(C_1-C_3)$alkyl, $(C_2-C_3)$olefinic group, $(C_1-C_3)$alkoxy, $(C_1-C_3)$alkoxycarbonyl and cyano.

In another preferred embodiment, X represents O or N—$OR_c$.

In another preferred embodiment, $R_6$ represents $(C_1-C_6)$alkyl-heterocyclyl, $(C_1-C_6)$alkyl-$(C_3-C_9)$cyclic hydrocarbon group, $(C_1-C_6)$alkyl, $(C_2-C_6)$olefinic group, $(C_3-C_6)$ cyclic hydrocarbon group, heterocyclyl, $(C_2-C_6)$alkynyl, $Y_1R_{21}$, $Y_2R_{22}$ or $Y_4R_{24}$; wherein the $(C_1-C_6)$alkyl, $(C_2-C_6)$ olefinic group and $(C_3-C_6)$cyclic hydrocarbon group are substituted by one or more, same or different substituents represented by $R_7$ and wherein the $(C_1-C_6)$alkyl-heterocyclyl, $(C_1-C_6)$alkyl-$(C_3-C_9)$cyclic hydrocarbon group heterocyclyl and $(C_2-C_6)$alkynyl are optionally substituted by one or more, same or different substituents represented by $R_7$;

$R_7$ represents $R_{12}$, Y—H or Y—$R_{14}$; wherein the $R_{12}$ and Y—$R_{14}$ group are optionally substituted by one or more, same or different substituents represented by $R_8$;

$R_8$ represents $R_{12}$, Y—H, Y—$R_{14}$ or $R_{14}$; wherein the $R_{12}$, Y—$R_{14}$ and $R_{14}$ group are optionally substituted by one or more, same or different substituents represented by $R_9$;

$R_9$ represents $R_{12}$, Y—H, Y—$R_{14}$ or $R_{14}$; wherein the $R_{12}$, Y—$R_{14}$ and $R_{14}$ group are optionally substituted by one or more, same or different substituents represented by $R_{10}$;

$R_{10}$ represents $R_{12}$ or $R_{14}$; wherein the $R_{12}$, Y—$R_{14}$ and $R_{14}$ group are optionally substituted by one or more, same or different substituents represented by $R_{12}$;

$R_{12}$ represents halogen, hydroxy, mercapto, trifluoromethyl, amino, $(C_1-C_3)$alkoxy, $(C_1-C_3)$alkylthio, $(C_1-C_6)$alkylamino, $(C_1-C_3)$alkoxycarbonyl, $(C_1-C_6)$trialkylammonium in association with an anion, $(C_2-C_6)$dialkylphosphinoyl, $(C_1-C_3)$alkyl(hydroxy)phosphinoyl, $(C_2-C_6)$ dialkylphosphinoyloxy, $(C_1-C_3)$alkyl(hydroxy)phosphinoyloxy, dihydroxyphosphinoyl, dihydroxyphosphinoyloxy, cyano, azido, nitro, —CHO, —COOH, —CONH$_2$, —CONHR', or —CONRR'; wherein R and R' represent $(C_1-C_3)$alkyl;

Y represents —O—, —S—, —S(O)—, —S(O)$_2$—, —NR$_a$—, —NR$_a$C(Z)NR$_b$—, —NR$_a$C(Z)—, —C(Z) NR$_a$—, —C(O)—, —C(Z)O—, —OC(Z)—, —NR$_a$C(Z) O—, —OC(Z)NR$_a$—, —S(O)$_2$O—, —OS(O)$_2$—, —S(O)$_2$NR$_a$—, —NR$_a$S(O)$_2$—, —OC(Z)Z—, —OP(O) (OR$_a$)O—, —P(O)(OR$_a$)O—, —C(NOR$_a$)—, —N(OR$_a$)—, —ON(R$_a$)—, —N(R$_a$)O—, —N(R$_a$)C (=NR$_b$)NR$_c$—, —C(=NR$_a$)NR$_b$— or —N(R$_a$)C (=NR$_b$)—;

Z represents oxygen;

$R_{14}$ represents $(C_1-C_6)$alkyl, $(C_2-C_6)$olefinic group, $(C_3-C_9)$cyclic hydrocarbon group, heterocyclyl or $(C_2-C_6)$alkynyl;

$Y_1$ represents —NR$_a$C(S)NR$_b$—, —C(O)—, —OC(O)—, —NR$_a$C(S)O—, —OC(Z)NR$_a$—, S(O)$_2$NR$_a$—, NR$_a$S (O)$_2$—, —OC(Z)O—, —C(NR$_a$)—, —C(NOR$_a$)—, —N(OR$_a$)—, —ON(R$_a$)—, —N(R$_a$)O—, —N(R$_a$)C (=NR$_b$)NRC—, —C(=NR$_a$)NR$_b$— or —N(R$_a$)C (=NR$_b$)—;

$R_{21}$ represents $(C_1-C_6)$alkyl-heterocyclyl, $(C_1-C_6)$alkyl-$(C_3-C_9)$cyclic hydrocarbon group, $(C_1-C_6)$alkyl, $(C_2-C_6)$ olefinic group, $(C_3-C_9)$cyclic hydrocarbon group, heterocyclyl or $(C_2-C_6)$alkynyl; any of which are optionally substituted by one or more, same or different substituents represented by $R_7$;

$Y_2$ represents —O—, —S—, —C(O)O— or —C(O)NR$_a$)—;

$R_{22}$ represents $(C_1-C_6)$alkyl-heterocyclyl, $(C_1-C_6)$alkyl-$(C_3-C_9)$cyclic hydrocarbon group, heterocyclyl, $(C_2-C_6)$ alkynyl, $(C_1-C_6)$alkyl, $(C_2-C_6)$olefinic group or $(C_3-C_9)$ monocyclic hydrocarbon group; wherein the $(C_1-C_6)$ alkyl is substituted by one or more, same or different substituents represented by $R_7$ and wherein the $(C_1-C_6)$ alkyl-heterocyclyl, $(C_1-C_6)$alkyl-$(C_3-C_9)$cyclic hydrocarbon group, heterocyclyl, $(C_2-C_6)$alkynyl, $(C_2-C_6)$olefinic group, and $(C_3-C_9)$monocyclic hydrocarbon group are optionally substituted by one or more, same or different substituents represented by $R_7$;

$Y_4$ represents for —NR$_a$C(O)NR$_b$CH(R$_c$)—, —NR$_a$C(O) NR$_b$S(O)$_2$—, —NR$_a$—, —NR$_a$C(Z)—, —NR$_a$C(O)OCH (R$_c$)—, —NR$_a$C(O)NR$_b$C(R$_d$)(R$_e$)—OC(O)— or —NR$_a$C(O)OC(R$_d$)(R$_e$)—OC(O)—;

R$_{24}$ represents (C$_1$–C$_6$)alkyl-heterocyclyl, (C$_1$–C$_6$)alkyl-(C$_3$–C$_9$)cyclic hydrocarbon group, heterocyclyl, (C$_2$–C$_6$)alkynyl, (C$_1$–C$_6$)alkyl, (C$_2$–C$_6$)olefinic group or (C$_3$–C$_9$)cyclic hydrocarbon group; wherein the (C$_1$–C$_6$)alkyl, (C$_2$–C$_6$)olefinic group, and (C$_3$–C$_9$)cyclic hydrocarbon group are substituted by one or more, same or different substituents represented by R$_{15}$, and wherein the (C$_1$–C$_6$)alkyl, (C$_2$–C$_6$)olefinic group, (C$_3$–C$_9$)cyclic hydrocarbon group, (C$_1$–C$_6$)alkyl-heterocyclyl, (C$_1$–C$_6$)alkyl-(C$_3$–C$_9$)cyclic hydrocarbon group, heterocyclyl and (C$_2$–C$_6$)alkynyl are optionally substituted by one or more, same or different substituents represented by R$_7$;

R$_{15}$ represents R$_{12a}$, R$_{12b}$ or R$_{12c}$; wherein R$_{12a}$, R$_{12b}$ and R$_{12c}$ are optionally substituted by one or more, same or different substituents represented by R$_7$;

R$_{12a}$ represents (C$_1$–C$_3$)alkoxy, (C$_1$–C$_3$)alkylthio, (C$_1$–C$_6$)alkylamino, (C$_1$–C$_3$)alkoxycarbonyl, —CONHR' or —CONRR' wherein R and R' represents (C$_1$–C$_3$)alkyl; any of which are substituted by one or more, same or different substituents represented by R$_{42}$; with the proviso that when R$_{12a}$ or R$_{15}$, including further substitution by R$_{42}$, represent groups of the formulas —(Q—O)$_n$—Q or —CH$_2$(Q—O)$_n$—Q, wherein Q is a (C$_1$–C$_3$)alkyl and n is an integer larger than 1, then said groups comprise a continuous linear sequence of atoms with at least 16 atoms;

R$_{12b}$ represents (C$_4$–C$_6$)alkoxy, (C$_4$–C$_6$)alkylthio, (C$_7$–C$_{12}$)alkylamino, (C$_4$–C$_8$)alkoxycarbonyl, —CONHR' or —CONRR'; wherein R and R' represent (C$_4$–C$_8$)alkyl; any of which are optionally substituted by one or more, same or different substituents represented by R$_7$;

R$_{12c}$ represents —Y$_5$(C$_1$–C$_6$)alkyl, —Y-aryl, —Y-heterocyclyl, —Y—(C$_3$–C$_9$)cyclic hydrocarbon group and —Y—(C$_2$–C$_6$)olefinic group; any of which are optionally substituted by one or more, same or different substituents represented by R$_7$;

Y$_5$ represents —S(O)—, —S(°)$_2$—, —NR$_a$C(Z)—, —NR$_a$C(Z)NR$_b$—, —C(O)—, —OC(Z)—, —NR$_a$C(Z)O—, —OC(Z)NR$_a$—, —S(O)$_2$NR$_a$—, —NR$_a$S(O)$_2$—, —OC(Z)O—, —OP(O)(OR$_a$)O—, —P(O)(OR$_a$)O—, —C(NR$_a$)—, —C(NOR$_a$)—, —N(OR$_a$)—, —ON(R$_a$)—, —N(R$_a$)O—, —N(R$_a$)C(=NR$_b$)NR$_c$—, —C(=NR$_a$)NR$_b$— or —N(R$_a$)C(=NR$_b$)—;

R$_{42}$ represents —Y—H, —Y—R$_{14}$, R$_{52}$, halogen, trifluoromethyl, cyano, azido or nitro; wherein R$_{52}$ and —Y—R$_{14}$ are optionally substituted by one or more, same or different substituents represented by R$_8$;

R$_{52}$ represents (C$_6$–C$_8$)alkyl, (C$_2$–C$_4$)olefinic group, (C$_3$–C$_6$)cyclic hydrocarbon group, heterocyclyl, (C$_2$–C$_4$)alkynyl or heteroaryl;

R$_a$, R$_b$, and R$_c$ independently represent hydrogen, (C$_1$–C$_4$)alkyl, (C$_2$–C$_4$)olefinic group, (C$_3$–C$_9$)cyclic hydrocarbon group, aryl, heterocyclyl or (C$_2$–C$_4$)alkynyl; any of which are optionally substituted by one or more, same or different substituents represented by R$_{12}$;

R$_d$ and R$_e$ independently represent hydrogen, (C$_1$–C$_4$)alkyl, (C$_2$–C$_4$)olefinic group, and (C$_3$–C$_9$)cyclic hydrocarbon group; any of which are optionally substituted by one or more, same or different substituents represented by R$_{12}$.

In still another preferred embodiment, R$_1$ represents a substituent selected from the group consisting of halogen, hydroxy, trifluoromethyl, amino, (C$_1$–C$_3$)alkyl, (C$_2$–C$_3$)olefinic group, (C$_1$–C$_3$)alkoxy and cyano;

R$_2$ represents one or more substituents independently selected from the group of hydrogen, halogen, hydroxy, trifluoromethyl, (C$_1$–C$_3$)alkyl, (C$_2$–C$_3$)olefinic group and (C$_1$–C$_3$)alkoxy;

R$_3$ represents one or more substituents independently selected from the group consisting of hydrogen, halogen, hydroxy, trifluoromethyl, cyano, nitro, (C$_1$–C$_6$)alkyl, (C$_2$–C$_6$)olefinic group, (C$_3$–C$_6$)monocyclic hydrocarbon group, (C$_1$–C$_6$)alkoxy and (C$_1$–C$_6$)alkoxycarbonyl;

R$_4$ represents hydrogen, (C$_1$–C$_6$)alkyl or (C$_2$–C$_6$)olefinic group;

and R$_5$ represents one or more substituents independently selected from the group consisting of hydrogen and halogen, hydroxy, trifluoromethyl, amino, (C$_1$–C$_3$)alkyl, (C$_2$–C$_3$)olefinic group, (C$_1$–C$_3$)alkoxy, (C$_1$–C$_3$)alkoxycarbonyl and cyano.

In a more preferred embodiment, R$_1$ represents substituents selected from the group consisting of halogen, cyano, methyl and methoxy.

In a more preferred embodiment, R$_2$ represents one or more substituents independently selected from the group consisting of hydrogen, halogen, cyano, methyl and methoxy.

In a more preferred embodiment, R$_3$ represents one or more substituents independently selected from the group consisting of hydrogen, halogen, hydroxy, methyl, methoxy and cyano.

In a more preferred embodiment, R$_4$ represents hydrogen, methyl or ethyl.

In a more preferred embodiment, R$_5$ represents one or more substituents independently selected from the group consisting of hydrogen, halogen, hydroxy, trifluoromethyl, methyl, ethyl and methoxy.

In a more preferred embodiment, X represents O.

In a more preferred embodiment, R$_6$ represents (C$_1$–C$_4$)alkyl-heterocyclyl, (C$_1$–C$_4$)alkyl-(C$_3$–C$_6$)cyclic hydrocarbon group, (C$_1$–C$_6$)alkyl, (C$_2$–C$_4$)olefinic group, heterocyclyl, (C$_2$–C$_4$)alkynyl, Y$_1$R$_{21}$, Y$_2$R$_{22}$ or Y$_4$R$_{24}$; wherein the (C$_1$–C$_6$)alkyl and (C$_2$–C$_4$)olefinic group are substituted by one or more, same or different substituents represented by R$_7$, and wherein the (C$_1$–C$_4$)alkyl-heterocyclyl, (C$_1$–C$_4$)alkyl-(C$_3$–C$_6$)cyclic hydrocarbon group heterocyclyl and (C$_2$–C$_4$)alkynyl are optionally substituted by one or more, same or different substituents represented by R$_7$;

R$_7$ represents R$_{12}$, Y—H or Y—R$_{14}$; wherein the R$_{12}$ and Y—R$_{14}$ group are optionally further substituted by one or more, same or different substituents represented by R$_8$;

R$_8$ represents R$_{12}$, Y—H, Y—R$_{14}$ or R$_{14}$; wherein the R$_{12}$, Y—R$_{14}$ and R$_{14}$ group are optionally further substituted by one or more, same or different substituents represented by R$_9$;

R$_9$ represents R$_{12}$, Y—R$_{14}$ or R$_{14}$; wherein the R$_{12}$, Y—R$_{14}$, and R$_{14}$ group are optionally further substituted by one or more, same or different substituents represented by R$_{12}$;

R$_{12}$ represents halogen, hydroxy, trifluoromethyl, amino, (C$_1$–C$_3$)alkoxy, (C$_1$–C$_3$)alkylthio, (C$_1$–C$_6$)alkylamino, (C$_1$–C$_3$)alkoxycarbonyl, (C$_1$–C$_6$)trialkylammonium in association with an anion, (C$_2$–C$_6$)dialkylphosphinoyl, (C$_2$–C$_6$)dialkylphosphinoyloxy, dihydroxyphosphinoyl, dihydroxyphosphinoyloxy, cyano, —COOH, —CONH$_2$, —CONHR' or —CONRR';

wherein R and R' represent (C$_1$–C$_3$)alkyl;

Y represents —O—, —S—, —S(O)—, —S(O)$_2$—, —NR$_a$—, —NR$_a$C(Z)NR$_b$—, —NR$_a$C(Z)—, —C(Z)NR$_a$—, —C(O)—, —C(Z)O—, —OC(Z)—, —NR$_a$C(Z)O—, —OC(Z)NR$_a$—, —S(O)20—, —OS(O)$_2$—, —S(O)

$_2NR_a$—, —$NR_aS(O)_2$—, —OC(Z)Z—, —$N(R_a)C(=NR_b)NR_c$—, —$C(=NR_a)NR_b$— or —$N(R_a)C(=NR_b)$—;

Z represents oxygen;

$R_{14}$ represents $(C_1-C_4)$alkyl, $(C_2-C_4)$olefinic group, $(C_3-C_6)$cyclic hydrocarbon group, heterocyclyl or $(C_2-C_3)$alkynyl;

$Y_1$ represents —$NR_aC(S)NR_b$—, —C(O)—, —OC(O)—, —$NR_aC(S)O$—, —$OC(Z)NR_a$—, —$S(O)_2NR_a$—, —$NR_aS(O)_2$— or —OC(Z)O—;

$R_{21}$ represents $(C_1-C_4)$alkyl-heterocyclyl, $(C_1-C_4)$alkyl-$(C_3-C_6)$cyclic hydrocarbon group, $(C_1-C_6)$alkyl, $(C_2-C_4)$olefinic group, $(C_3-C_6)$cyclic hydrocarbon group, heterocyclyl or $(C_2-C_6)$alkynyl; any of which are optionally substituted by one or more, same or different substituents represented by $R_7$;

$Y_2$ represents —O—, —S—, —C(O)O— or $C(O)NR_a$—;

$R_{22}$ represents $(C_1-C_4)$alkyl-heterocyclyl, $(C_1-C_4)$alkyl-$(C_3-C_6)$cyclic hydrocarbon group, heterocyclyl, $(C_2-C_4)$alkynyl, $(C_1-C_6)$alkyl, $(C_2-C_4)$olefinic group or $(C_3-C_6)$ monocyclic hydrocarbon group; wherein the $(C_1-C_6)$ alkyl is substituted by one or more, same or different substituents represented by $R_7$ and wherein the $(C_1-C_4)$ alkyl-heterocyclyl, $(C_1-C_4)$alkyl-$(C_3-C_6)$cyclic hydrocarbon group, heterocyclyl, $(C_2-C_4)$alkynyl, $(C_2-C_4)$olefinic group and $(C_3-C_6)$monocyclic hydrocarbon group are optionally substituted by one or more, same or different substituents represented by $R_7$;

$Y_4$ represents —$NR_aC(O)NR_bCH(R_c)$—, —$NR_aC(O)NR_bS(O)_2$—, —$NR_a$—, —$NR_aC(Z)$—, —$NR_aC(O)OCH(R_c)$—, —$NR_aC(O)NR_bC(R_d)(R_e)$—OC(O)— or —$NR_aC(O)OC(R_d)(R_e)$—OC(O)—;

$R_{24}$ represents $(C_1-C_4)$alkyl-heterocyclyl, $(C_1-C_4)$alkyl-$(C_3-C_6)$cyclic hydrocarbon group, heterocyclyl, $(C_2-C_4)$alkynyl, $(C_1-C_6)$alkyl, $(C_2-C_4)$olefinic group or $(C_3-C_9)$ cyclic hydrocarbon group; wherein the $(C_1-C_6)$alkyl, $(C_2-C_4)$olefinic group, and $(C_3-C_9)$cyclic hydrocarbon group are substituted by one or more, same or different substituents represented by $R_{15}$ and wherein the $(C_1-C_6)$ alkyl, $(C_2-C_4)$olefinic group, $(C_3-C_9)$cyclic hydrocarbon group, $(C_1-C_4)$alkyl-heterocyclyl, $(C_1-C_4)$alkyl-$(C_3-C_6)$ cyclic hydrocarbon group, heterocyclyl and $(C_2-C_4)$alkynyl are optionally substituted by one or more, same or different substituents represented by $R_7$;

$R_{15}$ represents $R_{12a}$, $R_{12b}$ or $R_{12c}$; wherein $R_{12a}$, $R_{12b}$ and $R_{12c}$ are optionally substituted by one or more, same or different substituents represented by $R_7$;

$R_{12a}$ represents $(C_1-C_3)$alkoxy, $(C_1-C_3)$alkylthio, $(C_1-C_6)$ alkylamino, $(C_1-C_3)$alkoxycarbonyl, —CONHR' or —CONRR' wherein R and R' represent $(C_1-C_3)$alkyl; any of which are substituted by one or more, same or different substituents represented by $R_{42}$; with the proviso that when $R_{12a}$ or $R_{15}$, including further substitution by $R_{42}$, represent groups of the formulas —(Q—O)$_n$—Q or —$CH_2$(Q—O)$_n$—Q, wherein Q is a $(C_1-C_3)$alkyl and n is an integer larger than 1, then said groups comprise a continuous linear sequence of atoms with at least 16 atoms;

$R_{12b}$ represents $(C_4-C_6)$alkoxy, $(C_4-C_6)$alkylthio, $(C_7-C_{12})$ alkylamino, $(C_4-C_8)$alkoxycarbonyl, —CONHR' or —CONRR' wherein R and R' represent $(C_4-C_8)$alkyl; any of which are optionally substituted by one or more, same or different substituents represented by $R_7$;

$R_{12c}$ represents —$Y_5(C_1-C_6)$alkyl, —Y-aryl, —Y-heterocyclyl, —Y—$(C_3-C_9)$cyclic hydrocarbon group and —Y—$(C_2-C_6)$olefinic group; any of which are optionally substituted by one or more, same or different substituents represented by $R_7$;

$Y_5$ represents —S(O)—, —$S(O)_2$—, —$NR_aC(Z)$—, —$NR_aC(Z)NR_b$—, —C(O)—, —OC(Z)—, —$NR_aC(Z)O$—, —$OC(Z)NR_a$—, —$S(O)_2NR_a$—, —$NR_aS(O)_2$— or —OC(Z)O—;

$R_{42}$ represents —Y—H, Y—$R_{14}$, $R_{52}$, halogen, trifluoromethyl, cyano, azido or nitro; wherein $R_{52}$ and —Y—$R_{14}$ are optionally substituted by one or more, same or different substituents represented by $R_8$;

$R_{52}$ represents $(C_6-C_8)$alkyl, $(C_2-C_4)$olefinic group, $(C_3-C_6)$cyclic hydrocarbon group, heterocyclyl, $(C_2-C_4)$ alkynyl or heteroaryl;

$R_a$, $R_b$ and $R_c$ independently represent hydrogen, $(C_1-C_2)$ alkyl, $(C_2-C_3)$olefinic group or $(C_2-C_3)$alkynyl; any of which are optionally substituted by one or more, same or different substituents represented by $R_{12}$;

$R_d$ and $R_e$ independently represent hydrogen or $(C_1-C_2)$ alkyl.

In a more preferred embodiment, $R_1$ represents substituents selected from the group consisting of halogen, cyano, methyl and methoxy;

$R_2$ represents one or more substituents independently selected from the group consisting of hydrogen, halogen, cyano, methyl and methoxy;

$R_3$ represents one or more substituents independently selected from the group consisting of hydrogen, halogen, hydroxy, methyl, methoxy and cyano;

$R_4$ represents hydrogen, methyl or ethyl;

$R_5$ represents one or more substituents independently selected from the group consisting of hydrogen, halogen, hydroxy, trifluoromethyl, methyl, ethyl and methoxy;

and X represents O.

In a particularly preferred embodiment, X represents O; $R_1$ represents methyl; $R_2$ represents 2-Cl; $R_3$ represents hydrogen or 4-Br, and $R_4$ and $R_5$ represent hydrogen.

The bioavailability of a drug is generally inversely proportional with the molecular weight of said drug. Rephrased, it means that any biological active structure will have an upper weight limit above which it ceases to be active due to a number of factors, such as insufficient solubility, inability to cross membranes, steric hindrance of drug-receptor interaction etc. Accordingly, in a more preferred embodiment, the invention relates to compounds of formula I with a molecular weight below 1500 Da or about 1500 Da, more preferably below 1200 Da or about 1200 Da, and even more preferably below 800 Da or about 800 Da.

In a still more preferred embodiment, the compound of formula I is selected from the group consisting of

[2-Chloro-4-({2-[2-(tetrahydro-2H-pyran-2-yloxy)ethyl] phenyl}amino)phenyl](2-methylphenyl)methanone;

(2-Chloro-4-{[2-(2-hydroxyethyl)phenyl]amino}phenyl)(2-methylphenyl)methanone;

2-(2-{[3-Chloro-4-(2-methylbenzoyl)phenyl] amino}phenyl)ethyl acetate;

4-(2-{2-[(3-Chloro-4-(2-methylbenzoyl)phenyl)amino] phenyl}ethoxy)-4-oxobutanoic acid;

2-(2-{[3-Chloro-4-(2-methylbenzoyl)phenyl] amino}phenyl)ethyl hexanoate;

2-(2-{[3-Chloro-4-(2-methylbenzoyl)phenyl] amino}phenyl)-1-methylethyl acetate;

(2-Chloro-4-{[2-(2-hydroxypropyl)phenyl]amino}phenyl) (2-methylphenyl)methanone;

[2-Chloro-4-({2-[(1E)-3-hydroxyprop-1-enyl] phenyl}amino)phenyl](2-methylphenyl)methanone;

(2-Chloro-4-{[2-(3-hydroxypropyl)phenyl]amino}phenyl)(2-methylphenyl)methanone;
[2-Chloro-4-({2-[(1E)-4-hydroxybut-1-enyl]phenyl}amino)phenyl](2-methylphenyl)methanone;
[4-({2-[(1E)-3-aminoprop-1-enyl]phenyl}amino)-2-chlorophenyl](2-methylphenyl)methanone;
Diethyl (2E)-3-(2-{[3-chloro-4-(2-methylbenzoyl)phenyl]amino}phenyl)prop-2-enylphosphonate;
[2-Chloro-4-({2-[(1E)-3-hydroxy-3-methylbut-1-enyl]phenyl}amino)phenyl](2-methylphenyl)methanone;
Ethyl (2E)-3-(2-{[3-chloro-4-(2-methylbenzoyl)phenyl]amino}phenyl)acrylate;
(2E)-3-(2-{[3-chloro-4-(2-methylbenzoyl)phenyl]amino}phenyl)acrylic acid;
{2-Chloro-4-[(2-{(1E)-3-[(2,2-dimethyl-1,3-dioxolan-4-yl)methoxy]prop-1-enyl}phenyl)amino]phenyl}(2-methylphenyl)methanone;
[2-Chloro-4-({2-[(1E)-3-(2,3-dihydroxypropoxy)prop-1-enyl]phenyl}amino)phenyl](2-methylphenyl)methanone;
Tert-butyl (1R)-3-{[(2E)-3-(2-{[3-chloro-4-(2-methylbenzoyl)phenyl]amino}phenyl)prop-2-enyl]amino}-1-(hydroxymethyl)-2-oxoethylylcarbamate;
Methyl O-(tert-butyl)-N-({[(2E)-3-(2-{[3-chloro-4-(2-methylbenzoyl)phenyl]amino}phenyl)prop-2-enyl]amino}carbonyl)-L-serinate;
N-(tert-butyl)-N'-[(2E)-3-(2-{[3-chloro-4-(2-methylbenzoyl)phenyl]amino}phenyl)prop-2-enyl]thiourea;
N-[(2E)-3-(2-{[3-chloro-4-(2-methylbenzoyl)phenyl]amino}phenyl)prop-2-enyl]-4-oxopentanamide;
N-[(2E)-3-(2-{[3-chloro-4-(2-methylbenzoyl)phenyl]amino}phenyl)prop-2-enyl]-N'-ethylurea;
Ethyl 4-{[(2E)-3-(2-{[3-chloro-4-(2-methylbenzoyl)phenyl]amino}phenyl)prop-2-enyl]amino}-4-oxobutanoate;
N-[(2E)-3-(2-{[3-chloro-4-(2-methylbenzoyl)phenyl]amino}phenyl)prop-2-enyl]-N'-cyclohexylurea; N'-[(2E)-3-(2-{[3-chloro-4-(2-methylbenzoyl)phenyl]amino}phenyl)prop-2-enyl]-N,N-dimethylsuccinamide;
Dimethyl [(2E)-3-(2-{[3-chloro-4-(2-methylbenzoyl)phenyl]amino}phenyl)prop-2-enyl]malonate;
[2-Chloro-4-({2-[(1E)-3-morpholin-4-ylprop-1-enyl]phenyl}amino)phenyl](2-methylphenyl)methanone;
6-O-[(2E)-3-(2-{[3-chloro-4-(2-methylbenzoyl)phenyl]amino}phenyl)prop-2-enyl]-1,2:3,4-di-O-(1-methylethylidene)-α-D-galactopyranose;
Methyl 5-O-[(2E)-3-(2-{[3-chloro-4-(2-methylbenzoyl)phenyl]amino}phenyl)prop-2-enyl]-2,3-O-(1-methylethylidene)-β-D-ribofuranoside;
Methyl 5-O-[(2E)-3-(2-{[3-chloro-4-(2-methylbenzoyl)phenyl]amino}phenyl)prop-2-enyl]-β-D-ribofuranoside;
Methyl (4E)-5-(2-{[3-chloro-4-(2-methylbenzoyl)phenyl]amino}phenyl)-2-(methylsulfonyl)pent-4-enoate;
Ethyl {[(2E)-3-(2-{[3-chloro-4-(2-methylbenzoyl)phenyl]amino}phenyl)prop-2-enyl]thio}acetate;
[2-Chloro-4-{[2-((1E)-3-{bis[2-(acetyloxy)ethyl]amino}prop-1-enyl)phenyl]amino}phenyl](2-methylphenyl)methanone;
[2-Chloro-4-{[2-((1E)-3-{bis[2-(hydroxy)ethyl]amino}prop-1-enyl)phenyl]amino}phenyl](2-methylphenyl)methanone;
(2-Chloro-4-{[2-((1E)-3-{4-[2-(acetyloxy)ethyl]piperidin-1-yl}prop-1-enyl)phenyl]amino}phenyl)(2-methylphenyl)methanone;
{2-chloro-4-[(2-{(1E)-3-[4-(hydroxyethyl)piperidin-1-yl]prop-1-enyl}phenyl)amino] phenyl}(2-methylphenyl)methanone;

{2-Chloro-4-[(2-{2-[(tetrahydrofuran-2-ylmethyl)amino]ethyl}phenyl)amino]phenyl}(2-methylphenyl)methanone;
[2-Chloro-4-({2-[2-(4-methylpiperazin-1-yl)ethyl]phenyl}amino)phenyl](2-methylphenyl)methanone;
{2-Chloro-4-[(2-{2-[(3-morpholin-4-ylpropyl)amino]ethyl}phenyl)amino]phenyl}(2-methylphenyl)methanone;
(2-Chloro-4-{[2-(2-{[2-(dimethylamino)ethyl]amino}ethyl)phenyl]amino}phenyl)(2-methylphenyl)methanone;
{2-Chloro-4-[(2-{2-[(2-methoxyethyl)amino]ethyl}phenyl)amino]phenyl}(2-methylphenyl)methanone;
1-[3-({2-[2-({3-Chloro-4-[(2-methylphenyl)carbonyl]phenyl}amino)phenyl]ethyl}amino)propyl]pyrrolidin-2-one;
{2-Chloro-4-[(2-{2-[methyl(tetrahydrofuran-2-ylmethyl)amino]ethyl}phenyl)amino]phenyl}(2-methylphenyl)methanone;
(2-Chloro-4-{[2-(2-{[(2,2-dimethyl-1,3-dioxolan-4-yl)methyl]amino}ethyl)phenyl]amino}phenyl)(2-methylphenyl)methanone;
{2-Chloro-4-[(2-{2-[4-(2-methoxyethyl)piperazin-1-yl]ethyl}phenyl)amino]phenyl}(2-methylphenyl)methanone;
(2-Chloro-4-{[2-(2-morpholin-4-yiethyl)phenyl]amino}phenyl)(2-methylphenyl)methanone;
{2-Chloro-4-[(2-{2-[(2,3-dihydroxypropyl)amino]ethyl}phenyl)amino]phenyl}(2-methylphenyl)methanone;
(4-{[2-(Aminomethyl)phenyl]amino}-2-chlorophenyl)(2-methylphenyl)methanone;
(2-Chloro-4-{[2-({2-[2-(tetrahydro-2H-pyran-2-yloxy)ethoxy]ethoxy}methyl)phenyl]amino}phenyl)(2-methylphenyl)methanone;
{2-Chloro-4-[(2-{[(tetrahydro-2H-pyran-2-yloxy)ethoxy]methyl}phenyl)amino]phenyl}(2-methylphenyl)methanone;
[2-Chloro-4-({2-[(2-{2-[2-(tetrahydro-2H-pyran-2-yloxy)ethoxy]ethoxy}ethoxy)methyl]phenyl}amino)phenyl](2-methylphenyl)methanone;
[2-Chloro-4-({2-[(3,3,3-trifluoropropoxy)methyl]phenyl}amino)phenyl](2-methylphenyl)methanone;
Diethyl 2-({3-chloro-4-[(2-methylphenyl)carbonyl]phenyl}amino)benzylphosphonate;
2-[2-({3-Chloro-4-[(2-methylphenyl)carbonyl]phenyl}amino)benzyl]-1H-isoindole-1,3(2H)-dione;
{2-Chloro-4-[(2-{[2-(2-hydroxyethoxy)ethoxy]methyl}phenyl)amino]phenyl}(2-methylphenyl)methanone;
[2-Chloro-4-{[2-[(hydroxyethoxy)methyl]phenyl}amino)phenyl](2-methylphenyl)methanone;
(2-Chloro-4-{[2-({2-[2-(2-hydroxyethoxy)ethoxy]ethoxy}methyl)phenyl]amino}phenyl)(2-methylphenyl)methanone;
[4-({4-Bromo-2-[(2-hydroxyethoxy)methyl]phenyl}amino)-2-chlorophenyl](2-methylphenyl)methanone;
(4-{[4-Bromo-2-({2-[2-(2-hydroxyethoxy)ethoxy]methyl)phenyl]amino}-2-chlorophenyl)(2-methylphenyl)methanone;
{4-[(4-Bromo-2-{[2-(2-hydroxyethoxy)methyl]phenyl}amino]-2-chlorophenyl}(2-methylphenyl)methanone;
Diethyl 5-bromo-2-({3-chloro-4-[(2-methylphenyl)carbonyl]phenyl}amino)benzylphosphonate;

[4-({4-Bromo-2-[(3,3,3-trifluoropropoxy)methyl]
  phenyl}amino)-2-chlorophenyl](2-methylphenyl)methanone;
2-{[2-({3-Chloro-4-[(2-methylphenyl)carbonyl]
  phenyl}amino)benzyl]oxy}ethyl 4-methylbenzenesulfonate;
2-{[5-Bromo-2-({3-chloro-4-[(2-methylphenyl)carbonyl]
  phenyl}amino)benzyl]oxy}ethyl 4-methylbenzenesulfonate;
2-(2-{[5-Bromo-2-({3-chloro-4-[(2-methylphenyl)carbonyl]phenyl}amino) benzyl]oxy}ethoxy)ethyl 4-methylbenzenesulfonate;
2-[2-(2-{[5-Bromo-2-({3-chloro-4-[(2-methylphenyl)carbonyl]phenyl}amino)benzyl]oxy}ethoxy)ethoxy]ethyl 4-methylbenzenesulfonate;
[4-({4-Bromo-2-[(2-iodoethoxy)methyl]phenyl}amino)-2-chlorophenyl](2-methylphenyl)methanone;
{4-[(4-Bromo-2-{[2-(2-iodoethoxy)ethoxy]methyl}phenyl)amino]-2-chlorophenyl}(2-methylphenyl)methanone;
(4-{[4-Bromo-2-({2-[2-(2-iodoethoxy)ethoxy]ethoxy}methyl)phenyl]amino}-2-chlorophenyl)(2-methylphenyl)methanone;
[2-Chloro-4-({2-[(2-iodoethoxy)methyl]phenyl}amino) phenyl](2-methylphenyl)methanone;
Diethyl 2-{[2-({3-chloro-4-[(2-methylphenyl)carbonyl] phenyl}amino)benzyl]oxy}ethylphosphonate;
Diethyl 2-{[5-bromo-2-({3-chloro-4-[(2-methylphenyl)carbonyl]phenyl}amino) benzyl]oxy}ethylphosphonate;
Diethyl 2-({[5-bromo-2-({3-chloro-4-[(2-methylphenyl)carbonyl]phenyl}amino) benzyl]oxy}ethoxy)ethylphosphonate;
Diethyl 2-[2-(2-{[5-bromo-2-({3-chloro-4-[(2-methylphenyl)carbonyl]phenyl}amino)benzyl]oxy}ethoxy)ethoxy]ethylphosphonate;
Diethyl 2-{[2-({3-chloro-4-[(2-methylphenyl)carbonyl] phenyl}amino)benzyl]amino}-2-oxoethylphosphonate;
Diethyl 2-{[5-bromo-2-({3-chloro-4-[(2-methylphenyl)carbonyl]phenyl}amino)phenyl]amino}-2-oxoethylphosphonate;
{[2-({5-Bromo-3-Chloro-4-[(2-methylphenyl)carbonyl] phenyl}amino)benzyl]oxy}ethyl (diethoxyphosphoryl) acetate;
2-({3-Chloro-4-[(2-methylphenyl)carbonyl]phenyl}amino) benzylphosphonic acid;
N-[2-({3-Chloro-4-[(2-methylphenyl)carbonyl] phenyl}amino)benzyl]-2,2,2-trifluoroethanesulfonamide;
N-[5-Bromo-2-({3-chloro-4-[(2-methylphenyl)carbonyl] phenyl}amino)phenyl]-2,2,2-trifluoroethanesulfonamide;
{2-Chloro-4-[(2-{[(tetrahydro-2H-pyran-2-yloxy)propoxy] methyl}phenyl)amino]phenyl}(2-methylphenyl)methanone;
[2-Chloro-4-({2-[(hydroxypropoxy)methyl]phenyl}amino) phenyl](2-methylphenyl)methanone;
Diethyl 3-{[2-({3-chloro-4-[(2-methylphenyl)carbonyl] phenyl}amino) benzyl]oxy}propylphosphonate;
Diethyl 2-[2-({3-chloro-4-[(2-methylphenyl)carbonyl] phenyl}amino) phenyl]ethylphosphonate;
Diethyl 2-[5-bromo-2-({3-chloro-4-[(2-methylphenyl)carbonyl]phenyl}amino)phenyl]ethylphosphonate;
2-{[2-({3-Chloro-4-[(2-methylphenyl)carbonyl] phenyl}amino) benzyl]amino}-2-oxoethylphosphonic acid;
(2-{[3-Chloro-4-(2-methylbenzoyl)phenyl]amino}phenyl)-carbamic acid phenethyl ester;
N-(2-{[3-Chloro-4-(2-methylbenzoyl)phenyl] amino}phenyl)-2-phenoxy-acetamide;
N-(2-{[3-Chloro-4-(2-methylbenzoyl)phenyl] amino}phenyl)-3-phenoxy-propionamide;
N-(2-{[3-Chloro-4-(2-methylbenzoyl)phenyl] amino}phenyl)-2-(1,3-dioxo-1,3-dihydro-isoindole-2-yl)-acetamide;
N-(2-{[3-Chloro-4-(2-methylbenzoyl)phenyl] amino}phenyl)-succinamic acid 2-(2-methoxy-ethoxy) ethyl ester;
N-(2-{[3-Chloro-4-(2-methylbenzoyl)phenyl] amino}phenyl)-benzenesulfonamide;
Acetic acid (2-{[3-chloro-4-(2-methylbenzoyl)phenyl] amino} phenylcarbamoyl)-methyl ester;
1-(2-{[3-Chloro-4-(2-methylbenzoyl)phenyl] amino}phenyl)pyrrolidine-2,5-dione;
2-(2-{[3-Chloro-4-(2-methylbenzoyl)phenyl] amino}phenyl)ethyl propionate;
2,2-Dimethyl-propionic acid 2-(2-{[3-chloro-4-(2-methylbenzoyl)phenyl]amino}phenyl)ethyl ester;
[2-Chloro-4-({2-[3-(tetrahydro-2H-pyran-2-yloxy)propoxy] phenyl}amino) phenyl](2-methylphenyl)methanone;
(2-Chloro-4-{[2-(3-hydroxypropoxy)phenyl] amino}phenyl)(2-methylphenyl)methanone;
tert-Butyl 2-(2-{[3-chloro-4-(2-methylbenzoyl)phenyl] amino}phenyl)ethyl carbonate;
2-({[(5-Bromo-2-{[3-chloro-4-(2-methylbenzoyl)phenyl] amino}phenyl)amino]carbonyl}amino)ethyl 2-methylacrylate;
(4-{[4-Bromo-2-(2-hydroxyethyl)phenyl]amino}-2-chlorophenyl)(2-methylphenyl)methanone;
3-(2-{[3-Chloro-4-(2-methylbenzoyl)phenyl] amino}phenoxy)propyl acetate;
[2-Chloro-4-({2-[3-(morpholin-4-yl)propoxy] phenyl}amino)phenyl](2-methylphenyl)methanone;
N-(2-{[3-Chloro-4-(2-methylbenzoyl)phenyl] amino}phenyl) —N'-(4-phenoxybutyl)succinamide;
N-(2-{[3-Chloro-4-(2-methylbenzoyl)phenyl] amino}phenyl) —N'-(6-hydroxyhexyl)succinamide;
N-(2-{[3-Chloro-4-(2-methylbenzoyl)phenyl] amino}phenyl)-N'-(2,3-dihydroxyproyl)succinamide;
tert-Butyl (1R)-3-(2-{[3-chloro-4-(2-methylbenzoyl)phenyl]amino}phenyl)-1-(hydroxymethyl)propylcarbamate;
Diethyl 6-[3-(2-{[3-chloro-4-(2-methylbenzoyl)phenyl] amino}phenylcarbamoyl)propionylamino]-hexyl phosphate;
Ethyl N-({[(2E)-3-(2-{[3-chloro-4-(2-methylbenzoyl)phenyl]amino}phenyl)prop-2-enyl]amino}carbonyl)glycinate;
tert-Butyl 2-(2-{[3-chloro-4-(2-methylbenzoyl)phenyl] amino}phenyl) ethyl(methyl)carbamate;
N-(5-Bromo-2-{[3-chloro-4-(2-methylbenzoyl)phenyl] amino}phenyl)-N'-(6-hydroxyhexyl)succinamide;
N-(5-Bromo-2-{[3-chloro-4-(2-methylbenzoyl)phenyl] amino}phenyl)-N'-(2,3-dihydroxyproyl)succinamide;
(2Z)-N-[(2E)-3-(2-{[3-chloro-4-(2-methylbenzoyl)phenyl] amino}phenyl)prop-2-enyl]-2-(2,5-dioxoimidazolidin-4-ylidene)acetamide;
(2-Chloro-4-{[2-(difluoromethyl)phenyl]amino}phenyl)(2-methylphenyl)methanone;
3-{[2-({3-Chloro-4-[(2-methylphenyl)carbonyl] phenyl}amino) phenyl]ethyl}-1-methylimidazolidine-2,4-dione;
3-{[2-({3-Chloro-4-[(2-methylphenyl)carbonyl] phenyl}amino) phenyl]ethyl}-5,5-dimethyloxazoline-2,4-dione;
4-{[2-({3-Chloro-4-[(2-methylphenyl)carbonyl] phenyl}amino) phenyl]ethyl}morpholine-3,5-dione;

1-{[2-({3-Chloro-4-[(2-methylphenyl)carbonyl]
   phenyl}amino) phenyl]ethyl}piperidine-2,6-dione;
4-(2-{[5-Bromo-2-({3-chloro-4-[(2-methylphenyl)carbonyl]phenyl}amino)benzyl]oxy}ethyl)morpholine-3,5-dione;
1-(2-{[5-Bromo-2-({3-chloro-4-[(2-methylphenyl)carbonyl]phenyl}amino)benzyl]oxy}ethyl)pyrrolidine-2,5-dione;
Ethyl 2-[3-(2-{5-bromo-[2-({3-chloro-4-[(2-methylphenyl)carbonyl]phenyl}amino)bezyloxy}ethyl)-2,4,5-trioxoimidazolidin-1-yl]acetate;
3-(2-{[5-Bromo-2-({3-chloro-4-[(2-methylphenyl)carbonyl]phenyl}amino)benzyl]oxy}ethyl)imidazolidine-2,4-dione;
1-(2-{[5-Bromo-2-({3-chloro-4-[(2-methylphenyl)carbonyl]phenyl} amino)benzyl]oxy}ethyl)-3,4-cis-diacetoxypyrrolidine-2,5-dione;
3-(2-{[5-Bromo-2-({3-chloro-4-[(2-methylphenyl)carbonyl]phenyl}amino) benzyl]oxy}ethyl)thiazoline-2,4-dione;
3-(2-{[5-Bromo-2-({3-chloro-4-[(2-methylphenyl)carbonyl]phenyl}amino)benzyl]oxy}ethyl)-1-methylimidazolidine-2,4-dione;
1-(2-{[5-Bromo-2-({3-chloro-4-[(2-methylphenyl)carbonyl]phenyl}amino)benzyl]oxy}ethyl)imidazolidine-2,4,5-trione;
(2-Chloro-4-{[(2-hydroxymethyl)phenyl]amino}phenyl)(2-methylphenyl)methanone;
2-{[3-Chloro-4-(2-methylbenzoyl)phenyl]amino}benzyl acetate; and pharmaceutically acceptable salts and solvates, e.g. hydrates thereof.

The compounds of formula I may contain double bonds, ring systems and asymmetric carbon atoms, which allow for isomeric forms. It is understood that the present invention relates to all such isomeric forms represented by the general formula I, in pure form or as mixtures thereof.

The term "pharmaceutically acceptable salt" is intended to indicate salts prepared by reacting a compound of formula I with a suitable inorganic or organic acid, e.g. hydrochloric, hydrobromic, hydroiodic, sulfuric, nitric, acetic, phosphoric, lactic, maleic, phthalic, citric, propionic, benzoic, glutaric, gluconic, methanesulfonic, salicylic, succinic, tartaric, toluenesulfonic, sulfamic or fumaric acid. Pharmaceutically acceptable salts of compounds of formula I may also be prepared by reaction with a suitable base such as sodium hydroxide, potassium hydroxide, ammonia or the like.

The term "solvate" is intended to indicate a species formed by interaction between a compound, e.g. a compound of formula I, and a solvent, e.g. alcohol, glycerol and water, wherein said species are in a solid form. When water is the solvent, said species is referred to as a hydrate.

The term "continuous linear sequence of atoms" is intended to indicate a string of atoms, not including any hydrogen atoms. Thus, diethyl ether and di-1-propyl ketone are continuous linear sequences of atoms with 5 and 7 atoms, respectively.

The term "halogen" is intended to indicate members of the seventh main group of the periodic table, i.e. fluoro, chloro, bromo and iodo.

The term "alkyl" is intended to indicate univalent groups derived from a straight or branched alkane by removal of a hydrogen atom from any carbon atom, and it includes the subclasses of primary, secondary and tertiary alkyl groups, including for example ($C_1$–$C_3$)alkyl, ($C_1$–$C_{10}$)alkyl, methyl, ethyl, n-propyl, isopropyl, n-butyl, isobutyl, sec-butyl, t-butyl, pentyl, hexyl, heptyl, decanyl, etc.

The term "olefinic group" is intended to indicate a straight or branched acyclic hydrocarbon having one or more carbon-carbon double bonds of either E or Z stereochemistry where applicable. The term includes, for example, ($C_2$–$C_{10}$) olefinic group, ($C_2$–$C_3$)olefinic group, vinyl, allyl, 1-butenyl, 2-butenyl, and 2-methyl-2-propenyl, 2,4-pentenedienyl, etc.

The term "alkoxy" is intended to indicate a radical of the formula —OR, where R is alkyl as defined above, for example ($C_1$–$C_{10}$)alkoxy, ($C_1$–$C_3$)alkoxy, methoxy, ethoxy, n-propoxy, tert-butoxy, etc.

The term "alkylthio" is intended to indicate a radical of the formula —SR, where R is alkyl as defined above, for example ($C_1$–$C_{10}$)alkylthio, ($C_1$–$C_3$)alkylthio, methylthio, ethylthio, n-propylthio, 2-propylthio, etc.

The term "alkylamino" is intended to indicate a radical of the formula —NHR or —$NR_2$, where R is alkyl as defined above and includes, for example, methylamino, dimethylamino, di-(n-propyl)amino, n-butyl(ethyl)amino, etc.

The term alkoxycarbonyl" is intended to indicate a radical of the formula —COOR, where R is alkyl as defined above and includes methoxycarbonyl, ethoxycarbonyl, n-propoxycarbonyl, i-propoxycarbonyl, etc.

The term "cyclic hydrocarbon group" includes saturated and unsaturated, optionally fused bicyclic, hydrocarbon rings, such as ($C_3$–$C_{12}$)cycloalkyl, cyclopropyl, cyclopentyl, cyclohexyl, and cyclooctyl, ($C_3$–$C_{12}$)cycloalkene group, such as cycloprop-2-enyl, cyclobut-2-enyl, cyclopent-2-enyl, cyclohex-3-enyl, cycloocta-4-enyl, cyclohex-3,5-dienyl, indanyl, indeneyl, 1,4-dihydronaphtyl, phenyl and naphtyl. The term "cyclic hydrocarbon group" also includes compounds as just defined wherein one or more ring —$CH_2$— fragments have been replaced by a —C(O)— fragment and/or an exo-cyclic carbon-carbon double bond, such as oxocyclohexyl, oxocyclopentyl, 4-oxo-1,2,3,4-tetrahydronaphtalen-1-yl, 1-oxo-1,2,3,4-tetrahydronaphtalen-1-yl, 2-oxocyclohex-3-en-1-yl and 2-oxocyclohex-1-en-1-yl, and

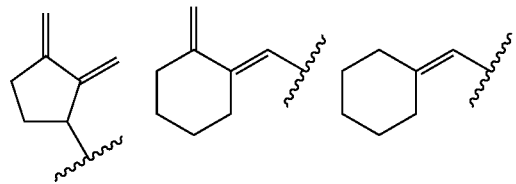

The term "alkynyl" is intended to indicate univalent group derived from a straight or branched alkyne by removal of a hydrogen atom from any carbon atom, and includes the subclasses of primary, secondary and tertiary alkyl groups respectively, and having the number of carbon atoms specified, including for example ($C_1$–$C_{10}$)alkynyl, ethynyl, propynyl, 1,1-dimethyl-3-butynyl, etc.

The term "heterocyclyl" is intended to indicate saturated or unsaturated, optionally fused carbocyclic rings comprising one or more heteroatoms selected from the group consisting of O, N and S, such as pyrrolyl, furanyl, thiophenyl, imidazolyl, oxazolyl, thiazolyl, pyrazolyl, pyrrolidinyl, pyridinyl, pyrimidinyl, tetrahydrotiophenyl, tetrahydrofuranyl, tetrahydropyranyl, piperidinyl, putinyl, quinolinyl, isoquinolinyl, 1,2-dihydroquinolinyl, etc. The term "heterocyclyl" also includes compounds as just defined wherein one or more ring —$CH_2$— fragments have been replaced by a —C(O)— fragment and/or an exo-cyclic carbon-carbon double bond, such as dioxopiperidinyl, 1-oxo-3,4-dihydroisoquinolin-2(1H)-yl and

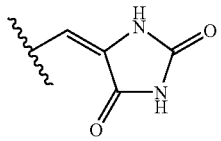

The compounds of the present invention are useful in the human and veterinary practice as systemic or topical therapeutic agents for the profylaxis, treatment and/or amelioration of disease severity, disease symptoms, and/or periodicity of reoccurrence of diseases associated with dysfunctions in the anti-inflammatory or cytokine regulatory system. These diseases or conditions include acne, asthma, allergy, arthritis, including rheumatic arthritis and spondyloarthritis, gout, atherosclerosis, chronic inflammatory bowel disease (Chron's disease), proliferative and inflammatory skindiseases, such as psoriasis, atopic dermatitis, uveitis, septic shock, AIDS and osteroporosis.

In another aspect, the invention relates to pharmaceutical formulations of a compound of formula I. The formulations of the present invention, both for veterinary and for human medical use, comprise active ingredients, optionally in association with a pharmaceutically acceptable carrier(s) and optionally other therapeutic ingredient(s). The carrier(s) must be "acceptable" in the sense of being compatible with the other ingredients of the formulations and not deleterious to the recipient thereof.

Conveniently, the active ingredient comprises from 0.1–100% by weight of the formulation. Conveniently, dosage unit of a formulation contain between 0.07 mg and 1 g of a compound of formula I.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations include e.g. those in a form suitable for oral (including sustained or timed release), rectal, parenteral (including subcutaneous, intraperitoneal, intramuscular, intraarticular and intravenous), transdermal, ophthalmic, topical, nasal or buccal administration.

The formulations may conveniently be presented in dosage unit form and may be prepared by any of the methods well known in the art of pharmacy, e.g. as disclosed in Remington, *The Science and Practice of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol.9, 1994, are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Tehcnology, vol.2, 1989, may also be used to present the active ingredient for ophthalmic administration. Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for nasal or buccal administration include powder, self-propelling and spray formulations, such as aerosols and atomisers.

Prodrugs of the present invention may also be delivered by use of monoclonale antibodies as individual carriers to which the compound molecules are coupled.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

In the systemic treatment using the present invention daily doses of from 0.001–500 mg per kilogram body weight, preferably from 0.002–100 mg/kg of mammal body weight, for example 0.003–20 mg/kg of a compound of formula I is administered, typically corresponding to a daily dose for an adult human of from 0.01 to 37000 mg. In the topical treatment of dermatological disorders, ointments, creams or lotions containing from 0.1–750 mg/g, and preferably from 0.1–500 mg/g, for example 0.1–200 mg/g of a compound of formula I is administered. For topical use in ophthalmology ointments, drops or gels containing from 0.1–750 mg/g, and preferably from 0.1–500 mg/g, for example 0.1–200 mg/g of a compound of formula I is administered. The oral compositions are formulated, preferably as tablets, capsules, or drops, containing from 0.07–1000 mg, preferably from 0.1–500 mg, of a compound of formula I per dosage unit.

The invention also includes incorporating other pharmaceutically active ingredients, normally used in the treatment of the disease states mentioned above, into the formulation of the present invention. Without limitations, such other pharmaceutically active ingredients may be glucocorticoids, vitamin D analogues, anti-histamines, platelet activating factor (PAF) antagonists, anticolergenic agents, methyl xanthines, β-adregenic agents, COX-2 inhibitors, salicylates, indomethacin, flufenamate, naproxen, timegadine, gold salts, peniciliamine, serum cholesterol reducing agents, retinoids, zinc salts and salicylazosulfapyridin.

The inventors have also found that a particular set of compounds are well suited for the preparation of compounds of formula I. Accordingly, the invention also provides compounds selected from the list consisting of 2-(2-bromophenyl)-1-methylethyl acetate (Compound 402);
(3E)-2-methyl-4-(tributylstannyl)but-3-en-2-ol (Compound 403);
Tributyl{(1E)-3-[(2,2-dimethyl-1,3-dioxolan-4-yl)methoxy]prop-1-enyl}stannane (Compound 404);
Dimethyl [(2E)-3-(tributylstannyl)prop-1-enyl]malonate (Compound 405);
4-[(2E)-3-(tributylstannyl)prop-2-enyl]morpholine (Compound 406);
1,2:3,4-di-O-(2-methylethylidene)-6-O-[(2E)-3-(tributylstannyl)prop-2-enyl]-α-D-galactopyranose (Compound 407);
Methyl 2,3-O-(1-methylethylidene)-5-O-[(2E)-3-(tributylstannyl)prop-2-enyl]-β-D-ribofuranoside (Compound 408);
Methyl (4E)-2-(methylsulfonyl)-5-(tributylstannyl)pent-4-enoate (Compound 409);
Ethyl {[(2E)-3-(tributylstannyl)prop-2-enyl]thio}acetate (Compound 410);
Tributyl{(1E)-3-[bis(2-hydroxyethyl)amino]prop-1-enyl}stannane (Compound 411); Tributyl((1E)-3-{bis[2-(acetyloxy)ethyl]amino}prop-1-enyl)stannane (Compound 412);
Tributyl{(1E)-3-[4-(2-hydroxyethyl)piperidin-1-yl]prop-1-enyl}stannane (Compound 413);
Tributyl((1E)-3-{4-[2-(acetyloxy)ethyl]piperidin-1-yl}prop-1-enyl)stannane (Compound 414);
2-(2-{(2-Bromobenzyl)oxy}ethoxy)ethanol (Compound 415);
2-(2-{2-[(2-Bromobenzyl)oxy]ethoxy}ethoxy)ethanol (Compound 416);
2-Bromobenzyl 3,3,3-trifluoropropyl ether (Compound 419);
2-(2-{2-[(2-Bromobenzyl)oxy]ethoxy}ethoxy)tetrahydro-2H-pyran (Compound 420);
2-[2-(2-{2-[(2-Bromobenzyl)oxy]ethoxy}ethoxy)ethoxy]tetrahydro-2H-pyran (Compound 421);
2-{2-[(2-Bromobenzyl)oxy]ethoxy}tetrahydro-2H-pyran (Compound 422);
2-{3-[(2-Bromobenzyl)oxy]propoxy}tetrahydro-2H-pyran (Compound 425);
3-[(2-Bromobenzyl)oxy]propyl 4-methylbenzenesulfonate (Compound 426);
1-Bromo-2-(3-iodo-propoxymethyl)benzene (Compound 427);
Diethyl 3-[(2-bromobenzyl)oxy]propylphosphonate (Compound 428);
Diethyl 2-(2-bromophenyl)ethylphosphonate (Compound 431);
(2-Chloro-4-iodophenyl)(2-methylphenyl)methanone (Compound 432);
tert-Butyl (4R)-4-[2-(2-aminophenyl)ethyl]-2,2-dimethyl-1,3-oxazolidine-3-carboxylate (Compound 433);
tert-Butyl (4R)-4-[2-(2-{[3-chloro-4-(2-methylbenzoyl)phenyl]amino}phenyl)ethyl]-2,2-dimethyl-oxazolidine-3-carboxylate (Compound 434);
tert-Butyl [2-(2-bromophenyl)ethyl](methyl)carbamate (Compound 435);
3-[2-(2-Bromophenyl)ethyl]-1-methylimidazolidine-2,4-dione (Compound 436);
3-[2-(2-Bromophenyl)ethyl]-5,5-dimethyloxazolidine-2,4-dione (Compound 437);
4-[2-(2-Bromophenyl)ethyl]morpholine-3,5-dione (Compound 438);
1-[2-(2-Bromophenyl)ethyl]piperidine-2,6-dione (Compound 439);
2-Bromobenzyl (triisopropyl)silyl ether (Compound 440);
{2-Chloro-4-[(2-{[(triisopropyl)siloxy]methyl}phenyl)amino]phenyl}(2-methylphenyl)methanone (Compound 441);

Methods of Preparation

The compounds of the present invention can be prepared in a number of ways well known to those skilled in the art of organic synthesis. The compounds of the present invention can be synthesised using the methods outlined below, together with methods known in the art of synthetic organic chemistry, or variations thereof as appreciated by those skilled in the art. Preferred methods include, but are not limited to, those described below.

The compounds of formula I may be prepared using the reactions and techniques described in this section. The reactions are performed in solvents that are appropriate with respect to the reagents and materials employed and that are suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionality present on various portions of the educt molecule must be compatible with the reagents and reactions proposed. Not all compounds of formula I falling into a given class may be compatible with some of the reaction conditions required in some of the methods described. Such restrictions to the substituents which are compatible with the reaction conditions will be readily apparent to one skilled in the art and alternative methods can be used.

Compounds according to the present invention may be prepared by a process comprising coupling of an amine of the formula III with a bromide, iodide, fluoride, chloride or triflate with the formula II, as shown in scheme 1, or alternatively by a process comprising coupling of an amine of the formula IIa with e.g. an iodide with the formula IIIa, as shown in scheme 1, where $R_1$, $R_2$, $R_3$, $R_4$, $R_5$, $R_6$ and X are as defined above, except that any substituents or functional groups which are potentially reactive in the coupling reaction may themselves be protected before the coupling reaction is performed and removed subsequently.

non-racemic 2,2'-bis(diphenylphosphino)-1,1'-binaphthyl (hereinafter refered to as BINAP), tri-o-tolylphosphine, tri-tert-butylphosphine, 1,1'-bis(diphenylphosphino)-ferrocene, bis[(2-diphenylphosphino)phenyl]ether (DPEphos), 2-dicyclohexylphosphanyl-2'-dimethylaminobiphenyl, 2-(di-tert-butylphosphino)biphenyl and 9,9-dimethyl-4,6-bis(diphenylphosphino)xanthene (Xantphos). The amount of palladium and ligand used in this process is typically in the range 0.1 to 10% by mole relative to the amount of the aromatic halide (or triflate) used. Especially sodium-tert-butoxide (NaOt-Bu) and caesium carbonate ($Cs_2CO_3$) have proven to be the preferred bases in this process, but other bases may be used as well. The reaction is typically performed at elevated temperatures (80–120° C.) in inert solvents like 1,4-dioxane, toluene, benzene and tetrahydrofurane under an inert atmosphere, e.g. argon or nitrogen.

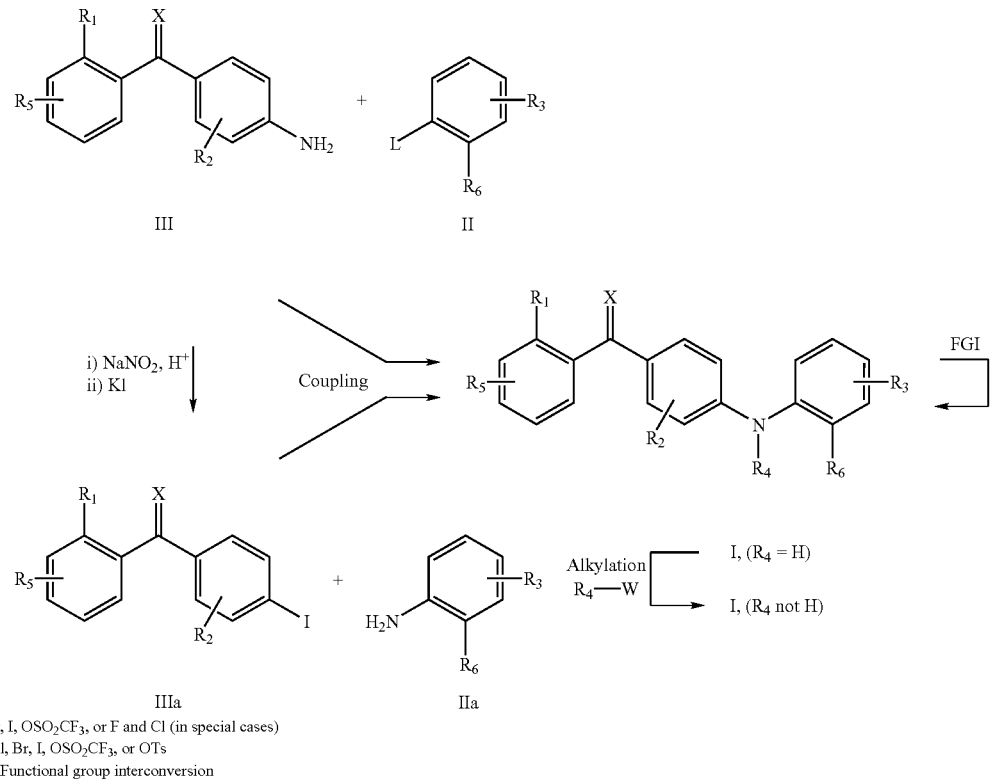

Scheme 1

L: Br, I, $OSO_2CF_3$, or F and Cl (in special cases)
W: Cl, Br, I, $OSO_2CF_3$, or OTs
FGI: Functional group interconversion The coupling reaction is carried out using any of the methods for the formation of diphenylamines known to one skilled in the art of organic synthesis. The preferred method is the palladium catalysed amination method which comprises coupling of an amine with an arylhalogenide (or aryltriflate) in the presence of a base, a suitable Pd source and a suitable phosphine ligand in an inert solvent. Different palladium compounds may be used in the process, non-limiting examples of which are palladium(II) acetate, palladium(II) chloride, palladium(II) bromide, dichlorobis(triphenylphosphine)palladium(II), tetrakis(triphenylphosphine)palladium(0), tris(dibenzylideneacetone)dipalladium(0). The preferred phosphine ligands include, but are not limited to, racemic or Compounds according to the present invention in which $R_4$ is not hydrogen may be prepared by a process comprising coupling of an amine of the formula I ($R_4$=H) with an alkylating agent, as shown in scheme 1, where $R_1$, $R_2$, $R_3$, $R_5$, $R_6$ and X are as defined in general formula I, except that any substituents or functional group which are potentially reactive in the coupling reaction may themselves be protected before the coupling reaction is performed and subsequently removed. Typically alkylating agents of the general formula $R_4$—W include, but are not limited to, iodides (W=I), bromides (W=Br), chlorides (W=Cl) and sulfonates (L=$OSO_2R'$, where R' represents methyl, trifluoromethyl or 4-methylphenyl).

Compounds according to the present invention may in special cases be prepared by a simple functional group interconversion (FGI), meaning a standard process, known to those skilled in the art of organic synthesis, where a functional group in compounds with the general formula I is transformed into a different functional group in one or more synthetic steps, leading to a new compound with the general formula I. Examples of such processes include, but are not limited to, hydrolysis of an ester to give an acid under basic conditions, deprotection of a methylether to give a phenol by treatment with e.g. borontribromide (BBr$_3$), and catalytic hydrogenation of an olefin to give a saturated hydrocarbon.

Compounds according to the present invention with the general formula I where X=S may be prepared from the ketone (with the general formula I, X=O) by such an FGI process using one of the many thiocarbonylating reagents known to those skilled in the art of organic synthesis. Examples of such thiocarbonylating reagents include, but are not limited to, phosphorous pentasulfide (P$_4$S$_{10}$), Lawesson's reagent (2,4-bis(4-methoxyphenyl)-1,3,2,4-dithiaphosphetane-2,4-disulfide) or the like.

Compounds according to the present invention with the general formula I where X=N—ORC may be prepared from the ketone (with the general formula I, X=O) by treatment with H$_2$N—ORC, or a protected derivative thereof followed by deprotection, in an appropriate solvent like e.g. pyridine or methanol. Compounds according to the present invention with the general formula III may be prepared by several methods known to those skilled in the art of organic synthesis. One useful sequence is shown in scheme 2. The key step comprising coupling of a bromide (or iodide) with the general formula VI with an acid chloride with the general formula V to afford the benzophenone with the general formula IV. This compound IV may then be reduced to the corresponding amine with the general formula III by treatment with standard reducing agents. Examples of such reducing agents include, but are not limited to, stannous chloride dihydrate; hydrogen, ammonium formiate or hydrazine hydrate and a catalytic amount of palladium on carbon. The coupling reaction is done by transforming the bromide (VI) into a reactive organometallic intermediate, e.g. by treatment with butyllithium to afford the lithium derivative or by treatment with magnesium to afford the magnesium derivative.

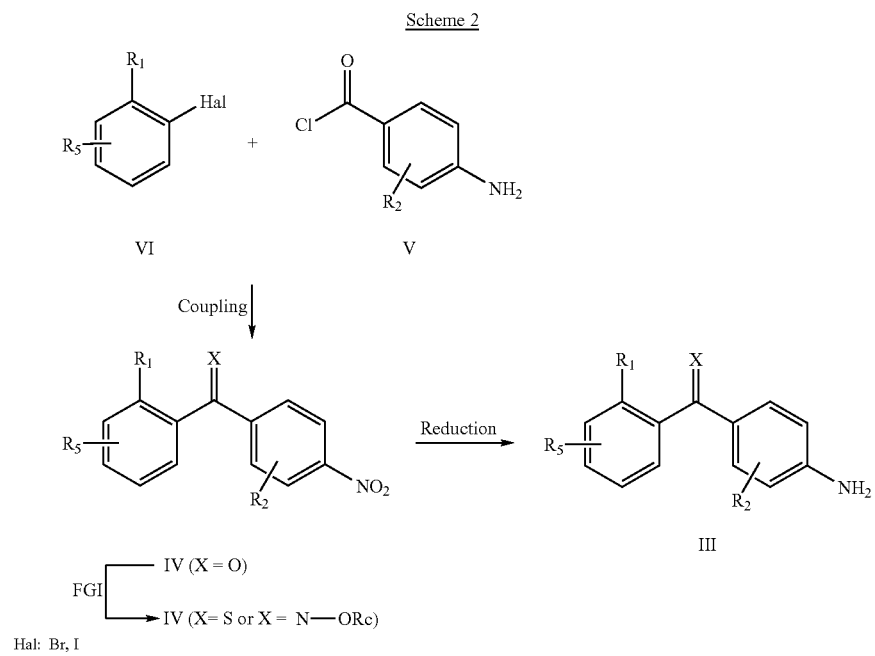

Scheme 2

The reactivity of this intermediate is then modulated by transmetalation to e.g. zinc, by treatment with ZnCl$_2$, ZnBr$_2$, or ZnI$_2$. This organozinc compound is then coupled with the acid chloride, with the general formula V, under the influence of a palladium(0) complex in catalytic amount. Examples of such catalyst include but are not limited to tetrakis(triphenylphosphine)palladium(0), tetrakis(triphenylarsine)palladium(0), dichlorobis(triphenylphosphine)palladium(II), or benzylchlorobis(triphenylphosphine)palladium (II).

As shown on scheme 2 compounds with the general formula IV (X=O) may be transformed by an FGI process to give compounds with the general formula IV (X=S or X=N—ORC) as described above. This is only to illustrate the flexibility in the synthesis, and in general the described sequence of processes is only one of many possible strategies for the synthesis of compounds of the present invention. That is, it may be more advantageous in some cases to alter the sequence of the processes described above. The described sequence of processes is not considered as being limited for the preparation of the compounds of the present invention with the general formula I and alteration of the reaction sequence may be an obvious alternative for those skilled in the art of organic synthesis. This aspect of the invention may be especially advantageous in the synthesis of compounds with different substituents in the R$_6$ group. Readily available intermediates may serve as starting point for the synthesis of various series of compounds covered by the general formula I. Examples of such compounds are shown on scheme 3 and 4 with examples of synthesis of compounds (Ia-Ie) covered by the general formula I. The readily available intermediates, e.g. VIIa, VIIb, and VIId may themselves be covered by the general formula I.

Scheme 3

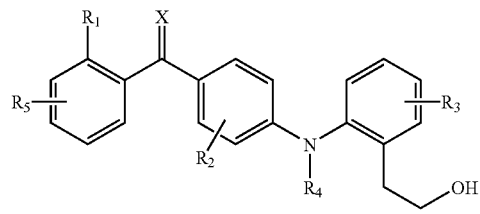

VIIa

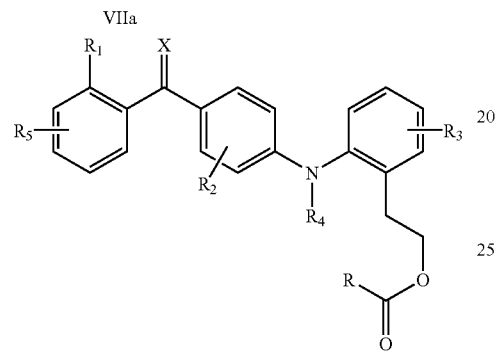

Ia

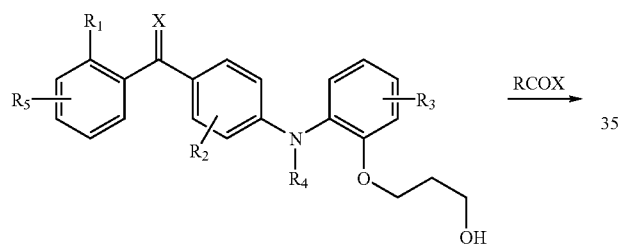

VIIb

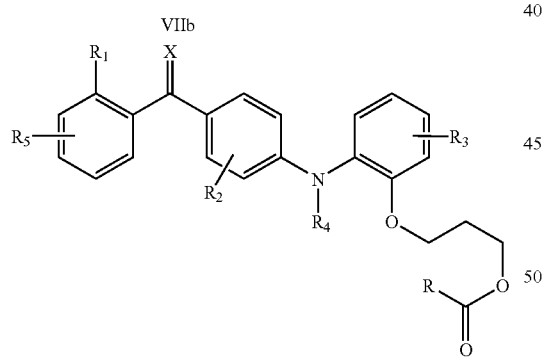

Ib

Compounds with a free hydroxy group (general formula VIIa, VIIb) may be coupled with a carboxylic acid (R—COOH) or an activated derivative thereof by a process well known to those skilled in the art of organic synthesis to give an ester with the general formula Ia and Ib.

Compounds with a free amino group (general formula VIc, VId) may be coupled with a carboxylic acid (R—COOH) or an activated derivative thereof by a process well known to those skilled in the art of organic synthesis to give an amide with the general formula Ic and Id.

Scheme 4

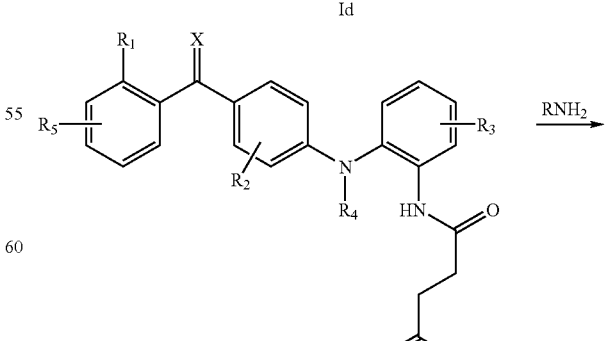

VIIe

-continued

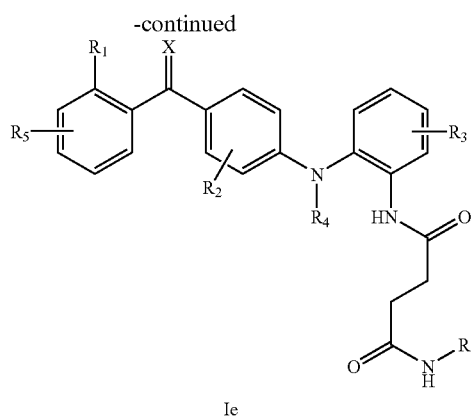

Ie

Compounds with a free carboxylic acid group (general formula VIIe) group may be coupled with an amine (R—$NH_2$) as described above by a process well known to those skilled in the art of organic synthesis to give an amide with the general formula Ie.

A suitable reactive derivative of a carboxylic acid is, for example, an acyl chloride, a mixed anhydride, or an active ester. The reactions are typically performed in an inert solvent like diethylether, tetrahydrofuran or dichloromethane in the presence of a suitable base like triethylamine, potassium carbonate or pyridine. Necessary starting materials like the compounds with the general formulas II, IIa, R—$NH_2$, and R—COOH may be prepared by methods known in the literature or by standard procedures of organic chemistry. The preparation of such starting materials is described in the accompanying Preparations.

General Procedures, Preprations and Examples

The exemplified compounds are listed in Table 1.

All melting points are uncorrected. For $^1H$ nuclear magnetic resonance (NMR) spectra (300 MHz) and $^{13}C$ NMR (75.6 MHz) chemical shift values (δ) (in ppm) are quoted, unless otherwise specified, for deuteriochloroform solutions relative to internal tetramethylsilane (δ=0.00) or chloroform (δ=7.25) or deuteriochloroform (δ=76.81 for $^{13}C$ NMR) standard. The value of a multiplet, either defined (doublet (d), triplet (t), quartet (q) or not (m) at the approximate mid point is given unless a range is quoted. The organic solvents used were anhydrous. Chromatography was performed on silica gel using the flash technique.

The following abbreviations have been used throughout:

| | |
|---|---|
| BOC | tert-Butyloxycarbonyl |
| dba | Dibenzylideneacetone |
| DCM | Dichloromethane |
| DMF | N,N-Dimethylformamide |
| DMTMM | 4-(4,6-Dimethoxy-1,3,5-triazin-2-yl)-4-methylmorpholinium chloride |
| MS | Mass spectroscopy |
| NMM | N-methylmorpholine |
| NMR | Nuclear magnetic resonance |
| rac-BINAP | Racemic 2,2'-bis(diphenylphosphino)-1,1'-binaphtyl |
| RT | Room temperature |
| TFA | Trifluoroacetic acid |
| THF | Tetrahydrofuran |
| THP | Tetrahydropyran |

The numbering in Table 1 refers to the numbering in the formula below

TABLE 1

Exemplified compounds with the general formula I. (X = 0; $R_1$ = methyl; $R_2$ = 2-Cl; $R_3$, $R_4$, and $R_5$ = H; unless otherwise noted).

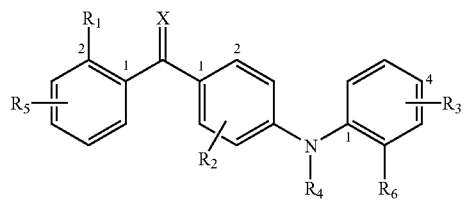

| Compound | Example no. | $R_6$ |
|---|---|---|
| 101 | 1 | —$CH_2CH_2OTHP$ |
| 102 | 2 | —$CH_2CH_2OH$ |
| 103 | 3 | —$CH_2CH_2OAc$ |
| 104 | 4 | —$CH_2CH_2O(CO)CH_2CH_2COOH$ |
| 105 | 5 | —$CH_2CH_2O(CO)CH_2CH_2CH_2CH_2CH_3$ |
| 106 | 6 | —$CH_2CH(CH_3)OAc$ |
| 107 | 7 | —$CH_2CH(CH_3)OH$ |
| 108 | 8 | ![structure]/\=\_OH |
| 109 | 9 | ![structure]/\_\_\_OH |

TABLE 1-continued
Exemplified compounds with the general formula I. (X = O; R$_1$ = methyl; R$_2$ = 2-Cl; R$_3$, R$_4$, and R$_5$ = H; unless otherwise noted).
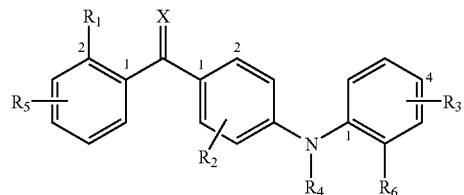
| Compound | Example no. | R$_6$ |
|---|---|---|
| 110 | 10 | /\=/\_OH |
| 111 | 11 | /\=/\_NH$_2$ |
| 112 | 12 | /\=/\_P(=O)(OEt)(OEt) |
| 113 | 13 | /\=/\_C(CH$_3$)$_2$OH |
| 114 | 14 | /\=/\_C(=O)OEt |
| 115 | 15 | /\=/\_C(=O)OH |
| 116 | 16 | /\=/\_O-CH$_2$-(2,2-dimethyl-1,3-dioxolan-4-yl) |
| 117 | 17 | /\=/\_O-CH$_2$-CH(OH)-CH$_2$OH |
| 118 | 18 | /\=/\_NH-C(=O)-CH(CH$_2$OH)-NH-C(=O)-O-C(CH$_3$)$_3$ |

TABLE 1-continued

Exemplified compounds with the general formula I. (X = O; R$_1$ = methyl; R$_2$ = 2-Cl; R$_3$, R$_4$, and R$_5$ = H; unless otherwise noted).

| Compound | Example no. | R$_6$ |
|---|---|---|
| 119 | 19 | –CH$_2$–CH=CH–CH$_2$–NH–C(=O)–NH–CH(CH$_2$–O–C(CH$_3$)$_3$)–C(=O)–O–CH$_3$ |
| 120 | 20 | –CH$_2$–CH=CH–CH$_2$–NH–C(=S)–NH–C(CH$_3$)$_3$ |
| 121 | 21 | –CH$_2$–CH=CH–CH$_2$–NH–C(=O)–CH$_2$–CH$_2$–C(=O)–CH$_3$ |
| 122 | 22 | –CH$_2$–CH=CH–CH$_2$–NH–C(=O)–NH–CH$_2$CH$_3$ |
| 123 | 23 | –CH$_2$–CH=CH–CH$_2$–NH–C(=O)–CH$_2$–CH$_2$–C(=O)–O–CH$_2$CH$_3$ |
| 124 | 24 | –CH$_2$–CH=CH–CH$_2$–NH–C(=O)–NH–cyclohexyl |
| 125 | 25 | –CH$_2$–CH=CH–CH$_2$–NH–C(=O)–CH$_2$–CH$_2$–C(=O)–N(CH$_3$)$_2$ |
| 126 | 26 | –CH$_2$–CH=CH–CH$_2$–CH(COOMe)–COOMe |
| 127 | 27 | –CH$_2$–CH=CH–CH$_2$–morpholinyl |

TABLE 1-continued

Exemplified compounds with the general formula I. (X = O; R$_1$ = methyl; R$_2$ = 2-Cl; R$_3$, R$_4$, and R$_5$ = H; unless otherwise noted).

| Compound | Example no. | R$_6$ |
|---|---|---|
| 128 | 28 | 3,4:5,6-di-O-isopropylidene sugar allyl ether |
| 129 | 29 | methyl 2,3-O-isopropylidene furanoside allyl ether |
| 130 | 30 | methyl furanoside diol allyl ether |
| 131 | 31 | methyl 2-(methylsulfonyl)pent-3-enoate |
| 132 | 32 | ethyl (allylthio)acetate |
| 133 | 33 | N,N-bis(2-acetoxyethyl)allylamine |
| 134 | 34 | N,N-bis(2-hydroxyethyl)allylamine |
| 135 | 35 | 2-(1-allylpiperidin-4-yl)ethyl acetate |

TABLE 1-continued
Exemplified compounds with the general formula I. (X = O; R₁ = methyl; R₂ = 2-Cl; R₃, R₄, and R₅ = H; unless otherwise noted).
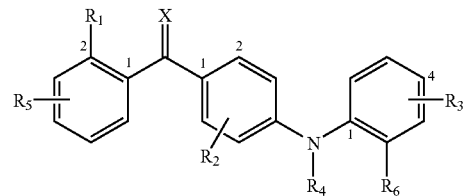
| Compound | Example no. | R₆ |
|---|---|---|
| 136 | 36 | |
| 137 | 37 | |
| 138 | 38 | |
| 139 | 39 | |
| 140 | 40 | |
| 141 | 41 | |
| 142 | 42 | |
| 143 | 43 | |
| 144 | 44 | |

TABLE 1-continued

Exemplified compounds with the general formula I. (X = O; $R_1$ = methyl; $R_2$ = 2-Cl; $R_3$, $R_4$, and $R_5$ = H; unless otherwise noted).

| Compound | Example no. | $R_6$ |
|---|---|---|
| 145 | 45 | -CH2CH2CH2-N(piperazine)-CH2CH2-OCH3 |
| 146 | 46 | -CH2CH2CH2-morpholine |
| 147 | 47 | -CH2CH2CH2-NH-CH2-CH(OH)-CH2OH |
| 148 | 48 | -CH2-NH2 |
| 149 | 49 | -CH2CH2-O-CH2CH2-O-CH2CH2-O-tetrahydropyran |
| 150 | 50 | -CH2CH2-O-CH2CH2-O-tetrahydropyran |
| 151 | 51 | -CH2CH2-O-CH2CH2-O-CH2CH2-O-CH2CH2-O-tetrahydropyran |
| 152 | 52 | -CH2CH2-O-CH2CH2-CF3 |
| 153 | 53 | -CH2-P(=O)(OEt)(OEt) |

TABLE 1-continued

Exemplified compounds with the general formula I. (X = O; R₁ = methyl; R₂ = 2-Cl; R₃, R₄, and R₅ = H; unless otherwise noted).

| Compound | Example no. | R₆ | |
|---|---|---|---|
| 154 | 54 | (phthalimidomethyl group) | |
| 155 | 55 | -CH₂CH₂-O-CH₂CH₂-O-CH₂CH₂-OH | |
| 156 | 56 | -CH₂CH₂-O-CH₂CH₂-OH | |
| 157 | 57 | -CH₂CH₂-O-CH₂CH₂-O-CH₂CH₂-O-CH₂CH₂-OH | |
| 158 | 58 | -CH₂CH₂-O-CH₂CH₂-OH | R₃ = 4-Br |
| 159 | 59 | -CH₂CH₂-O-CH₂CH₂-O-CH₂CH₂-O-CH₂CH₂-OH | R₃ = 4-Br |
| 160 | 60 | -CH₂CH₂-O-CH₂CH₂-O-CH₂CH₂-OH | R₃ = 4-Br |
| 161 | 61 | -CH₂CH₂-P(=O)(OEt)₂ | R₃ = 4-Br |
| 162 | 62 | -CH₂CH₂-O-CH₂CH₂-CF₃ | R₃ = 4-Br |
| 163 | 63 | -CH₂CH₂-O-CH₂CH₂-O-S(=O)₂-C₆H₄-CH₃ (tosylate) | |

TABLE 1-continued

Exemplified compounds with the general formula I. (X = O; R₁ = methyl; R₂ = 2-Cl; R₃, R₄, and R₅ = H; unless otherwise noted).

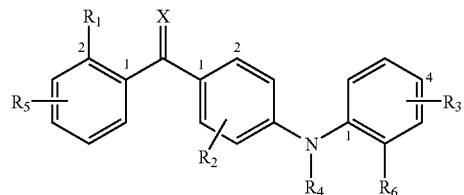

| Compound | Example no. | R₆ | |
|---|---|---|---|
| 164 | 64 | (CH₂CH₂O)₂-tosylate | R₃ = 4-Br |
| 165 | 65 | (CH₂CH₂O)₃-tosylate | R₃ = 4-Br |
| 166 | 66 | (CH₂CH₂O)₄-tosylate | R₃ = 4-Br |
| 167 | 67 | –CH₂CH₂OCH₂CH₂I | R₃ = 4-Br |
| 168 | 68 | –CH₂CH₂OCH₂CH₂OCH₂CH₂I | R₃ = 4-Br |
| 169 | 69 | –(CH₂CH₂O)₃CH₂CH₂I | R₃ = 4-Br |
| 170 | 70 | –CH₂CH₂OCH₂CH₂I | |
| 171 | 71 | –CH₂CH₂OCH₂CH₂P(O)(OEt)₂ | |
| 172 | 72 | –CH₂CH₂OCH₂CH₂P(O)(OEt)₂ | R₃ = 4-Br |

TABLE 1-continued
Exemplified compounds with the general formula I. (X = O; $R_1$ = methyl; $R_2$ = 2-Cl; $R_3$, $R_4$, and $R_5$ = H; unless otherwise noted).
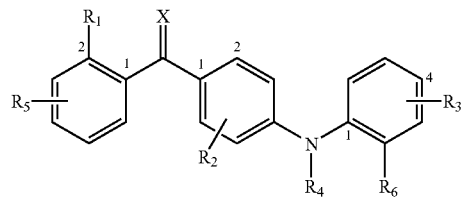
| Compound | Example no. | $R_6$ | |
|---|---|---|---|
| 173 | 73 | (structure) | $R_3$ = 4-Br |
| 174 | 74 | (structure) | $R_3$ = 4-Br |
| 175 | 75 | (structure) | |
| 176 | 76 | (structure) | |
| 177 | 77 | (structure) | $R_3$ = 4-Br |
| 178 | 78 | (structure) | |
| 179 | 79 | (structure) | |

TABLE 1-continued
Exemplified compounds with the general formula I. (X = O; $R_1$ = methyl; $R_2$ = 2-Cl; $R_3$, $R_4$, and $R_5$ = H; unless otherwise noted).
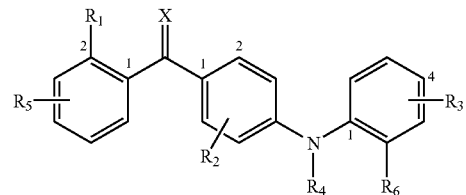
| Compound | Example no. | $R_6$ | |
|---|---|---|---|
| 180 | 80 | (HN-SO₂-CH₂-CF₃) | $R_3$ = 4-Br |
| 181 | 81 | (-CH₂-O-(CH₂)₃-O-THP) | |
| 182 | 82 | (-CH₂-O-(CH₂)₃-OH) | |
| 183 | 83 | (-CH₂-O-(CH₂)₃-P(O)(OEt)₂) | |
| 184 | 84 | (-(CH₂)₃-P(O)(OEt)₂) | |
| 185 | 85 | (-(CH₂)₃-P(O)(OEt)₂) | $R_3$ = 4-Br |
| 186 | 86 | (-CH₂CH₂-NH-C(O)-CH₂-P(O)(OH)₂) | |
| 187 | 87 | (HN-C(O)-O-CH₂CH₂-Ph) | |
| 188 | 88 | (HN-C(O)-CH₂-O-Ph) | |

TABLE 1-continued

Exemplified compounds with the general formula I. (X = O; R₁ = methyl; R₂ = 2-Cl; R₃, R₄, and R₅ = H; unless otherwise noted).

| Compound | Example no. | R₆ |
|---|---|---|
| 189 | 89 | -NHC(O)CH₂CH₂-O-phenyl |
| 190 | 90 | -NHC(O)CH₂-phthalimide |
| 191 | 91 | -NHC(O)CH₂CH₂C(O)OCH₂CH₂OCH₂CH₂OCH₃ |
| 192 | 92 | -N(CH₃)SO₂-phenyl |
| 193 | 93 | -NHC(O)CH₂OC(O)CH₃ |
| 194 | 94 | N-succinimidyl |
| 195 | 95 | -CH₂CH₂OC(O)CH₂CH₃ |

TABLE 1-continued
Exemplified compounds with the general formula I. (X = O; R₁ = methyl; R₂ = 2-Cl; R₃, R₄, and R₅ = H; unless otherwise noted).
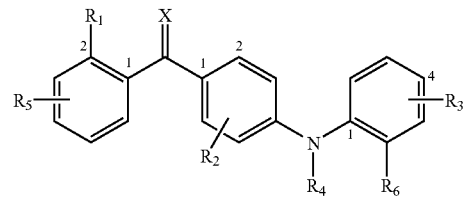
| Compound | Example no. | R₆ | |
|---|---|---|---|
| 196 | 96 | ![structure] | |
| 197 | 97 | ![structure] | |
| 198 | 98 | ![structure] | |
| 199 | 99 | ![structure] | |
| 200 | 100 | ![structure] | R₃ = 4-Br |
| 201 | 101 | ![structure] | R₃ = 4-Br |
| 202 | 102 | ![structure] | |
| 203 | 103 | ![structure] | |
| 204 | 104 | ![structure] | |

TABLE 1-continued

Exemplified compounds with the general formula I. (X = O; $R_1$ = methyl; $R_2$ = 2-Cl; $R_3$, $R_4$, and $R_5$ = H; unless otherwise noted).

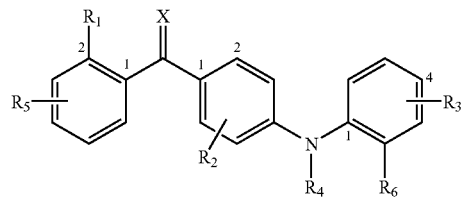

| Compound | Example no. | $R_6$ | |
|---|---|---|---|
| 205 | 105 | (structure: -NH-C(O)-CH2CH2-C(O)-NH-(CH2)6-OH) | |
| 206 | 106 | (structure: -NH-C(O)-CH2CH2-C(O)-NH-CH2-CH(OH)-CH2OH) | |
| 207 | 107 | (structure: -CH(NHBoc)-CH2OH with side chain) | |
| 208 | 108 | (structure: -NH-C(O)-CH2CH2-C(O)-NH-(CH2)6-O-P(O)(OEt)2) | |
| 209 | 109 | (structure: allyl-NH-C(O)-NH-CH2-C(O)-O-Et) | |
| 210 | 110 | (structure: -CH2CH2-N(CH3)-C(O)-O-tBu) | |
| 211 | 111 | (structure: -NH-C(O)-CH2CH2-C(O)-NH-(CH2)6-OH) | $R_3$ = 4-Br |

TABLE 1-continued

Exemplified compounds with the general formula I. (X = O; $R_1$ = methyl; $R_2$ = 2-Cl; $R_3$, $R_4$, and $R_5$ = H; unless otherwise noted).

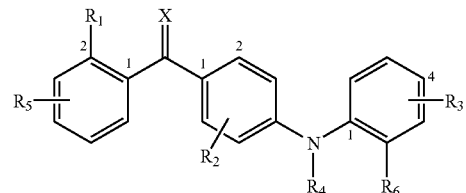

| Compound | Example no. | $R_6$ | |
|---|---|---|---|
| 212 | 112 | (HN-C(O)-CH2CH2-C(O)-NH-CH2-CH(OH)-CH2OH) | $R_3$ = 4-Br |
| 213 | 113 | (CH2-CH=CH-CH2-NH-C(O)-CH=hydantoin) | |
| 214 | 114 | (O-CHF2) | |
| 215 | 115 | (CH2CH2CH2-N-methylhydantoin) | |
| 216 | 116 | (CH2CH2CH2-N-dimethyloxazolidinedione) | |
| 217 | 117 | (CH2CH2CH2-N-morpholinedione) | |
| 218 | 118 | (CH2CH2CH2-N-glutarimide) | |
| 219 | 119 | (CH2CH2-O-CH2CH2-N-morpholinedione) | $R_3$ = 4-Br |

TABLE 1-continued

Exemplified compounds with the general formula I. (X = O; $R_1$ = methyl; $R_2$ = 2-Cl; $R_3$, $R_4$, and $R_5$ = H; unless otherwise noted).

| Compound | Example no. | $R_6$ | |
|---|---|---|---|
| 220 | 120 | –CH₂OCH₂CH₂–N(succinimide) | $R_3$ = 4-Br |
| 221 | 121 | –CH₂OCH₂CH₂–N(hydantoin-N'-CH₂CO₂Et) | $R_3$ = 4-Br |
| 222 | 122 | –CH₂OCH₂CH₂–N(hydantoin-NH) | $R_3$ = 4-Br |
| 223 | 123 | –CH₂OCH₂CH₂–N(3,4-diOAc-succinimide) | $R_3$ = 4-Br |
| 224 | 124 | –CH₂OCH₂CH₂–N(thiazolidine-2,4-dione) | $R_3$ = 4-Br |
| 225 | 125 | –CH₂OCH₂CH₂–N(N'-methyl-hydantoin) | $R_3$ = 4-Br |
| 226 | 126 | –CH₂OCH₂CH₂–N(parabanic acid) | $R_3$ = 4-Br |
| 227 | 127 | –CH₂CH₂OH | |

TABLE 1-continued

Exemplified compounds with the general formula I. (X = O; R$_1$ = methyl; R$_2$ = 2-Cl; R$_3$, R$_4$, and R$_5$ = H; unless otherwise noted).

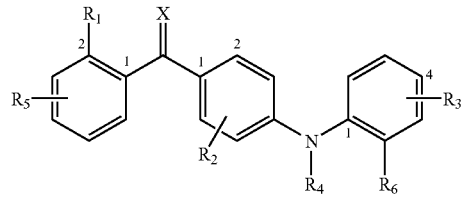

| Compound | Example no. | R$_6$ |
|---|---|---|
| 228 | 128 | 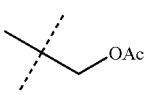 OAc |

Preparation 1:2-[2-(2-bromophenyl)ethoxy]tetrahydro-2H-pyran (Compound 401).

A solution of 2-bromophenethyl alcohol (9.88 g), 3,4-dihydro-2H-pyran (4.45 mL), and 4-toluenesulfonic acid (0.20 g) in THF (20 mL) was stirred for 2 hours at 50° C. and then at RT overnight. The reaction mixture was poured into a mixture of ice-water and EtOAc. The aqueous phase was extracted with more EtOAc (x 2). The combined organic phases were washed with saturated NaHCO$_3$, brine, dried (MgSO$_4$), filtered and concentrated in vacuo. The crude product was purified by chromatography eluting with petroleum ether/Et$_2$O 4:1 to afford the title compound as a colourless oil.

Preparation 2:2-(2-bromophenyl)-1-methylethyl acetate (Compound 402)

Acetic acid anhydride (1.2 mL) was added to a solution of 1-(2-bromophenyl)-2-propanol (529 mg) in pyridine (1.0 mL) at 20° C. under stirring. The reaction mixture was stirred overnight, then poured into a mixture of water and EtOAc. The aqueous phase was extracted with more EtOAc (×2). The combined organic phases were washed with water (×3), dried (MgSO$_4$), filtered and concentrated in vacuo to afford the title compound as a syrup.

Preparation 3: (3E)-2-methyl-4-(tributylstannyl)but-3-en-2-ol (Compound 403)

A mixture of 2-methylbut-3-yn-2-ol (2.00 g), tributyltinhydride (10.5 g) and αα'-azobisisobutyronitrile (190 mg) was heated (neat) to 80° C. under stirring. After 4 h the reaction mixture was cooled to room temperature. The crude product was purified by chromatography eluting with petroleum ether/Et$_2$O 7:1 to afford the title compound as a liquid.

Preparation 4: Tributyl{(1E)-3-[(2,2-dimethyl-1,3-dioxolan-4-yl)methoxy]prop-1-enyl}stannane (Compound 404)

Sodium hydride (215 mg) was added to a solution of (2,2-dimethyl-1,3-dioxolan-4-yl)methanol (644 mg) in dry DMF (25 mL) at 0° C. [(1E)-3-bromoprop-1-enyl](tributyl)stannane (1.00 g) was added to the reaction mixture after 10 min. The reaction mixture was stirred for 20 h at 20° C. and then quenched with saturated NH$_4$Cl (aq.). Extraction with EtOAc and drying (Na$_2$SO$_4$) of the organic phase gave, after concentration in vacuo, the crude product. Purification was done by chromatography eluting with petroleum ether/EtOAc 10:1 to afford the title compound as a liquid.

Preparation 5: Dimethyl [(2E)-3-(tributylstannyl)prop-1-enyl]malonate (Compound 405)

Sodium hydride (75 mg) was added to a solution of dimethyl malonate (387 mg) in dry DMF (5 mL) at 0° C. [(1E)-3-bromoprop-1-enyl](tributyl)stannane (600 mg) was added to the reaction mixture after 10 min. The reaction mixture was stirred for 3 h at 20° C. and then quenched with saturated NH$_4$Cl(aq.). Extraction with EtOAc and drying (MgSO$_4$) of the organic phase gave, after concentration in vacuo, the crude product. Purification was done by chromatography eluting with petroleum ether/Et$_2$O 12:1 to afford the title compound as a liquid.

Preparation 6:4-[(2E)-3-(tributylstannyl)prop-2-enyl]morpholine (Compound 406)

A solution of morpholine (637 mg) and [(1E)-3-bromoprop-1-enyl](tributyl)stannane (1.00 g) in dry DMF (8.0 mL) was stirred for 24 h at 20° C. The reaction mixture was quenched with saturated Na$_2$SO$_4$(aq.). Extraction with Et$_2$O and drying (MgSO$_4$) of the organic phase gave, after concentration in vacuo, the crude product. Purification was done by chromatography eluting with petroleum ether/EtOAc 10:1 to afford the title compound as a liquid.

Preparation 7: 1,2:3,4-di-O-(1-methylethylidene)-6-O-[(2E)-3-(tributylstannyl)prop-2-enyl]-α-D-galactopyranose (Compound 407)

Sodium hydride (62 mg) was added to a solution of 1,2:3,4-di-O-(1-methylethylidene)-α-D-galactopyranose (635 mg) in dry THF (8 mL) at 0° C. [(1E)-3-bromoprop-1-enyl](tributyl)stannane (500 mg) was added to the reaction after 10 min. The reaction mixture was stirred for 20 h at 20° C. and then quenched with saturated NaHCO$_3$ (aq.). Extraction with Et$_2$O and drying (Na$_2$SO$_4$) of the organic phase gave, after concentration in vacuo, the crude product. Purification was done by chromatography eluting with petroleum ether/Et$_2$O 9:1 to afford the title compound as a liquid.

Preparation 8: Methyl 2,3-O-(1-methylethylidene)-5-O-[(2E)-3-(tributylstannyl)prop-2-enyl]-β-D-ribofuranoside (Compound 408)

The reaction was carried out as described in the preparation of compound 407, using 2,3-O-(1-methylethylidene)-β-D-ribofuranose (598 mg) as the alcohol. Purification was done by flash chromatography eluting with a mixture of petroleum ether/EtOAc 30:1 to afford the title compound as a liquid.

Preparation 9: Methyl (4E)-2-(methylsulfonyl)-5-(tributylstannyl) pent-4-enoate (Compound 409)

The reaction was carried out as described in the preparation of compound 407, using methyl (methylsulfonyl)acetate (446 mg) as the nucleophilic component. Purification was done by flash chromatography eluting with a mixture of petroleum ether/Et$_2$O 5:1 to afford the title compound as a liquid.

Preparation 10: Ethyl {[(2E)-3-(tributylstannyl)prop-2-enyl]thio}acetate (Compound 410)

The reaction was carried out as described in the preparation of compound 407, using ethyl mercaptoacetate (550 mg) as the nucleophilic component. Purification was done by flash chromatography eluting with a mixture of petroleum ether/Et$_2$O 100:1 to afford the title compound as a liquid.

Preparation 11: Tributyl{(1E)-3-[bis(2-hydroxyethyl)amino]prop-1-enyl}stannane (Compound 411)

N-Ethyl-N,N-diisopropylamine (315 mg) was added to a solution of diethanolamine (256 mg) in dry DMF (5 mL) at 0° C. [(1E)-3-bromoprop-1-enyl](tributyl)stannane (600 mg) was added to the reaction after 10 min. The reaction mixture was stirred for 15 h at 20° C. and then quenched with saturated NH$_4$Cl (aq.). Extraction with Et$_2$O and drying (MgSO$_4$) of the organic phase gave, after concentration in vacuo, the crude product. Purification was done by chromatography eluting with Et$_2$O/MeOH 100:4 to afford the title compound as a liquid.

Preparation 12: Tributyl((1E)-3-{bis[2-(acetyloxy)ethyl]amino}prop-1-enyl)stannane (Compound 412)

The reaction was carried out as described in the preparation of compound 402, using compound 411 (575 mg) as the alcohol. Purification was done by flash chromatography eluting with a mixture of petroleum ether/Et$_2$O 4:1 to afford the title compound.

Preparation 13: Tributyl{(1E)-3-[4-(2-hydroxyethyl)piperidin-1-yl]prop-1-enyl}stannane (Compound 413)

The reaction was carried out as described in the preparation of compound 411, using compound 2-piperidin-4-ylethanol (504 mg) as the amine. Purification was done by flash chromatography eluting with a mixture of Et$_2$O/MeOH 92:8 to afford the title compound. Preparation 14: Tributyl((1E)-3-{4-[2-(acetyloxy)ethyl]piperidin-1-yl}prop-1-enyl)stannane (Compound 414)

The reaction was carried out as described in the preparation of compound 402, using compound 413 (510 mg) as the alcohol. Purification was done by flash chromatography eluting with a mixture of petroleum ether/Et$_2$O 1:2 to afford the title compound as a liquid.

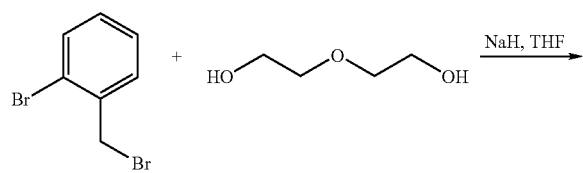

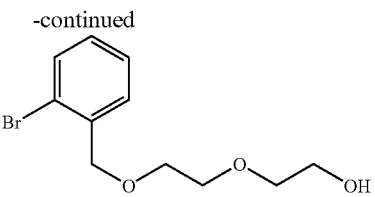

Preparation 15: 2-(2-{(2-Bromobenzyl)oxy}ethoxy)ethanol (Compound 415)

NaH (0.53 g, 60% in oil, 13 mmol) was suspended in dry THF (80 mL) in a dry schlenk tube under an argon atmosphere. Diethylenglycol (11.4 mL, 120 mmol) was added slowly under stirring. The suspension was stirred at RT for 30 min. 2-Bromo-benzylbromide (5.0 g, 20 mmol) dissolved in 5 mL dry THF was added followed by addition of tetrabutylammonium iodide (74 mg, 0.2 mmol). The reaction mixture was refluxed for 18 h after which H$_2$O (50 mL) was added. The water phase was extracted twice with EtOAc and the combined organic phases were washed with water and brine, dried (MgSO$_4$), filtered and evaporated in vacuo. The crude product was purified by flash chromatography eluting with DCM/acetone 3:1. This afforded the title compound as a yellow oil.

Preparation 16: 2-(2-{2-[(2-Bromobenzyl)oxy]ethoxy}ethoxy)ethanol (Compound 416)

The compound was prepared and worked up as described in the preparation of compound 415, using triethylenglycol (16.0 mL, 120 mmol) instead of diethylenglycol. The crude product was purified by flash chromatography using DCM/acetone 6:1–3:1 as the eluent to afford the title compound as a pale yellow oil.

Preparation 17: 2-((2-Bromobenzyl)oxy)ethanol (Compound 417)

The reaction and work up was conducted as described in the preparation of compound 415. Starting materials were NaH (60% in oil, 1.8 g, 44 mmol) in THF (160 mL), ethylenglycol (13.4 mL, 240 mmol), 2-bromo-benzyl bromide (10 g, 40 mmol) dissolved in 5 mL dry THF and tetrabutylammonium iodide (0.15 g, 0.4 mmol). The crude product was purified by flash chromatography using DCM/Acetone 30:1 as the eluent to afford the title compound as a pale yellow oil.

Preparation 18: Diethyl 2-bromobenzylphosphonate (Compound 418)

Diethyl phosphite (0.77 mL, 6.0 mmol) was dissolved in dry THF (10 mL) in a dry schlenk tube under an argon atmosphere. The solution was cooled on an ice bath and NaH (0.24 g, 60% in oil, 6.0 mmol) was added and stirred for 5 min. 2-bromo-benzylbromide (1.0 g, 4.0 mmol) dissolved in 2 mL dry THF was added and the reaction mixture was refluxed overnight. H$_2$O (20 mL) was added and the water phase was extracted with EtOAc (3×10 mL). The combined organic phases were washed with brine, dried (MgSO$_4$), filtered and evaporated in vacuo. The crude product was purified by flash chromatography using EtOAc as the eluent to afford the title compound as a colourless oil.

Preparation 19: 2-Bromobenzyl 3,3,3-trifluoropropyl ether (Compound 419)

The reaction and work up was conducted as described in the preparation of compound 415. Starting materials were NaH (60% in oil, 0.08 g, 2 mmol) in dry THF (10 mL), 3,3,3-trifluoropropan-1-ol (0.23 g, 2 mmol), 2-bromo-benzylbromide (0.50 g, 2 mmol) and tetrabutylammonium iodide (0.74 g, 0.2 mmol). The crude product was purified by flash chromatography using EtOAc/petroleum ether 1 : 35 as the eluent to afford the title compound as a pale yellow oil.

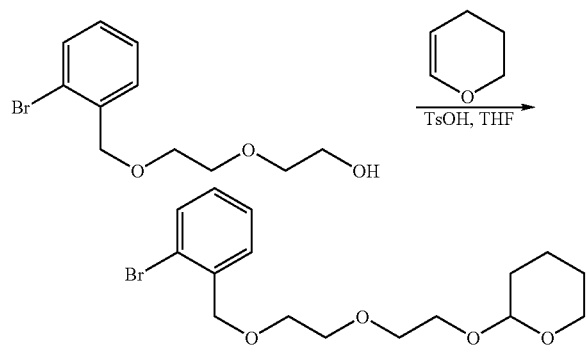

Preparation 20: 2-(2-{2-[(2-Bromobenzyl)oxy]ethoxy}ethoxy)tetrahydro-2H-pyran (Compound 420)

Compound 415 (2.78 g, 10.0 mmol) was dissolved in dry THF (6 mL) under an argon atmosphere. 3,4-Dihydro-2H-pyran (1.03 mL, 11.3 mmol) was added followed by addition of p-toluenesulfonic acid (43 mg, 0.23 mmol). The reaction mixture was heated at 50° C. for 2 h after which aqueous NaHCO$_3$ (5%, 30 mL) was added. The water phase was extracted with EtOAc (3×15 mL) and the combined organic phases were washed with water, dried (Na$_2$SO$_4$), filtered and evaporated in vacuo. The crude product was purified by flash chromatography eluting with EtOAc/petroleum ether 1:3. This afforded the title compound as a yellow oil.

Preparation 21: 2-[2-(2-{2-[(2-Bromobenzyl)oxy]ethoxy}ethoxy)ethoxy]tetra hydro-2H-pyran (Compound 421)

The compound was prepared and worked up as described in the preparation of compound 420. Starting compounds were compound 416 (2.82 g, 8.9 mmol) in 6 mL dry THF, 3,4-dihydro-2H-pyran (0.89 mL, 9.8 mmol) and p-toluenesulfonic acid (37 mg, 0.19 mmol). The crude product was purified by flash chromatography using EtOAc/petroleum ether 1:3 as the eluent to afford the title compound as a pale yellow oil.

Preparation 22: 2-{2-[(2-Bromobenzyl)oxy]ethoxy}tetrahydro-2H-pyran (Compound 422)

The reaction and work up was conducted as described in the preparation of compound 420. Starting materials were compound 417 (8.0 g, 34.9 mmol) in 20 mL dry THF, 3,4-dihydro-2H-pyran (3.2 mL, 34.9 mmol) and p-toluenesulfonic acid (0.14 g, 0.76 mmol) and the reaction time was 4 h. The crude product was purified by flash chromatography using EtOAc/petroleum ether 1:2 as the eluent to afford the title compound as a colourless oil.

Preparation 23: 2-(2-Bromobenzyl)-1H-isoindole-1,3(2H)-dione (Compound 423)

2-Bromobenzyl bromide (5.25 g, 21.0 mmol) was dissolved in dry DMF (200 mL) and potassium phthalimide (3.89 g, 21.0 mmol) was added. The suspension was stirred at 70° C. for 5 h. The mixture was cooled to room temperature and poured into ice water (200 mL). After 30 min the mixture was filtered and the crystalline compound was dried overnight. Recrystallisation from DCM/petroleum ether afforded the title compound as colourless crystals.

Preparation 24: 3-[(2-Bromobenzyl)oxy]propanol (Compound 424)

The reaction and work up was conducted as described in the preparation of compound 415. Starting materials were NaH (60% in oil, 0.86 g, 22 mmol) in THF (80 mL), 1,3-propanediol (8.67 mL, 120 mmol), 2-bromobenzylbromide (5.0 g, 20 mmol) dissolved in 4 mL dry THF and tetrabutylammonium iodide (0.07 g, 0.2 mmol). The crude product was purified by flash chromatography using EtOAc/petroleum ether 1:1->2:1 as the eluent to afford the title compound as a pale yellow oil.

Preparation 25: 2-{3-[(2-Bromobenzyl)oxy]propoxy}tetrahydro-2H-pyran (Compound 425)

The reaction and work up was conducted as described in the preparation of compound 420. Starting compounds were compound 424 (2.41 g, 9.8 mmol) in 7 mL dry THF, 3,4-dihydro-2H-pyran (0.99 mL, 10.8 mmol) and p-toluenesulfonic acid (37 mg, 0.19 mmol). The crude product was purified by flash chromatography using EtOAc/petroleum ether 1:4 as the eluent to afford the title compound as a pale yellow oil.

Preparation 26: 3-[(2-Bromobenzyl)oxy]propyl 4-methylbenzenesulfonate (Compound 426)

The reaction and work up was conducted as described in the preparation of compound 163 using compound 424 (2.50 g, 10.2 mmol) in pyridine (3 mL) and p-toluenesulfonyl chloride (2.14 g, 11.2 mmol). The crude product was purified by flash chromatography eluting with EtOAc/petroleum ether 1:3. This afforded the title compound as a colourless crystalline compound.

Preparation 27: 1-Bromo-2-(3-iodo-propoxymethyl)benzene (Compound 427)

The reaction and work up was conducted as described in the preparation of compound 167 using compound 426 (3.04 g, 7.6 mmol) in 8 mL acetone and NaI (2.28 g, 15.2 mmol). The crude product was purified by flash chromatography eluting with EtOAc/petroleum ether 1:2. This afforded the title compound as a colourless oil.

Preparation 28: Diethyl 3-[(2-bromobenzyl)oxy]propylphosphonate (Compound 428)

The reaction was conducted as described in the preparation of compound 171 using NaH (0.036 g, 60% in oil, 0.9 mmol) in dry THF (2 mL) and diethylphosphite (0.12 mL, 0.9 mmol). Addition of compound 427 (0.20 g, 0.6 mmol) dissolved in dry THF (1 mL), stirring at room temperature for 48 h and work up was carried out as described in the preparation of compound 171. The crude product was purified by flash chromatography using EtOAc as the eluent to afford the title compound as a colourless oil.

Preparation 29: 2-(2-Bromophenyl)ethyl 4-methylbenzenesulfonate (Compound 429)

The reaction and work up was conducted as described in the preparation of compound 163 using 2-bromophenethyl alcohol (5 g, 25 mmol) in pyridine (12 mL) and p-toluenesulfonyl chloride (5.2 g, 27.5 mmol). The crude product was purified by flash chromatography eluting with EtOAc/petroleum ether 1:4. This afforded the title compound as a colourless crystalline compound.

Preparation 30: 1-Bromo-2-(2-iodoethyl)benzene (Compound 430)

The reaction and work up was conducted as described in the preparation of compound 167 using compound 429 (7.98 g, 22.5 mmol) in 22 mL acetone and NaI (6.7 g, 44.9 mmol).

Flash chromatography of the crude product using petroleum ether as the eluent afforded the title compound as a colourless oil.

Preparation 31: Diethyl 2-(2-bromophenyl)ethylphosphonate (Compound 431)

The reaction was conducted as described in the preparation of compound 171 using NaH (0.19 g, 60% in oil, 4.8 mmol) in dry THF (10 mL) and diethylphosphite (0.62 mL, 4.8 mmol). Addition of compound 430 (1.0 g, 3.2 mmol) and stirring at room temperature for 18 h. Work up was carried out as described in the preparation of compound 171. The crude product was purified by flash chromatography using EtOAc/petroleum ether 0:1->1:0 as the eluent to afford the title compound as a colourless oil.

Preparation 32: (2-Chloro-4-iodophenyl)(2-methylphenyl)methanone (Compound 432)

To a stirred suspension of (4-amino-2-chlorophenyl)(2-methylphenyl)methanone (9.83 g, 40 mmol) (disclosed in WO 01/42189 A1) in HCl (37%, 150 mL) at 0° C. was added a solution of NaNO$_2$ (5.52 g, 80 mmol) in water (40 mL) over a period of 20 min. The reaction mixture was stirred for 15 min and a solution of KI (36 g, 240 mmol) in water (100 mL) was added under stirring. After 2 h at room temperature the aqueous phase was extracted twice with diethyl ether. The combined organic phases were washed with Na$_2$CO$_3$ (10%), NaHSO$_3$ (40%), dried over Na$_2$SO$_4$ and concentrated in vacuo. The residue was purified by flash chromatography using petroleum ether/EtOAc 40:1 as the eluent to afford the title compound as a solid.

Preparation 33: tert-Butyl (4R)-4-[2-(2-aminophenyl)ethyl]-2,2-dimethyl-1,3-oxazolidine-3-carboxylate (Compound 433)

Potassium tert-butoxide (498 mg, 4.44 mmol) was added to a solution of (2-nitrobenzyl)triphenylphosphonium chloride (2.04 g, 4.89 mmol) in 1,4-dioxane (10 mL) under an atmosphere of argon. The mixture was stirred for 30 min at room temperature and then at 80° C. for 40 min. A solution of tert-butyl (4S)-4-formyl-2,2-dimethyl-oxazolidine-3-carboxylate (510 mg, 2.22 mmol) in 1,4 dioxane (3.0 mL) was added with a syringe. The resulting mixture was refluxed for 4 h and then allowed to come to room temperature overnight. The reaction mixture was poured into water and extracted with EtOAc (×3). The organic phases were combined and washed with brine and dried with MgSO$_4$. The crude product was purified by flash chromatography eluting with petroleum ether/EtOAc 9:1 to afford a (Z)/(E) mixture of tert-Butyl (4R)-2,2-dimethyl-4-[2-(2-nitrophenyl)vinyl]-1,3-oxazolidine-3-carboxylate as a yellow oil. 288 mg of the obtained product was dissolved in EtOAc (10 ml), added Pd/C (40 mg, 10%) and then stirred under an atmosphere of hydrogen (1 atm) for 4 h. The reaction mixture was filtered through a pad of decalite and concentrated in vacuo. The crude product was purified by flash chromatography eluting with petroleum ether/EtOAc 2:1 to afford the title compound as a white solid.

Preparation 34: tert-Butyl (4R)-4-[2-(2-{[3-chloro-4-(2-methylbenzoyl)phenyl]amino}phenyl)ethyl]-2,2-dimethyl-oxazolidine-3-carboxylate (Compound 434)

The reaction and work up was conducted as described in the preparation of compound 101, using compound 432 (378 mg, 1.06 mmol) and compound 433 (340 mg, 1.06 mmol). Purification was done by flash chromatography eluting with petroleum ether/EtOAc 9:1 to afford the title compound as a foam.

Preparation 35: tert-Butyl [2-(2-bromophenyl)ethyl](methyl)carbamate (Compound 435)

A solution of tert-butyl [2-(2-bromophenyl)ethyl]carbamate (810 mg, 2.7 mmol) in dry THF (2.0 mL) was transferred to a flask with a suspension of sodium hydride (65 mg, 2.7 mmol) in dry THF (2.0 mL) under an atmosphere of argon. The mixture was stirred for 15 min at room temperature and 10 min at 60° C. Iodomethane (0.19 mL, 2.97 mmol) was added with a syringe. After 4 h the reaction mixture was poured into water and extracted with EtOAc (×3). The organic phases were combined and washed with brine and dried with MgSO$_4$. The crude product was purified by chromatography eluting with petroleum ether/EtOAc 10:1 to afford the title compound as a colourless oil.

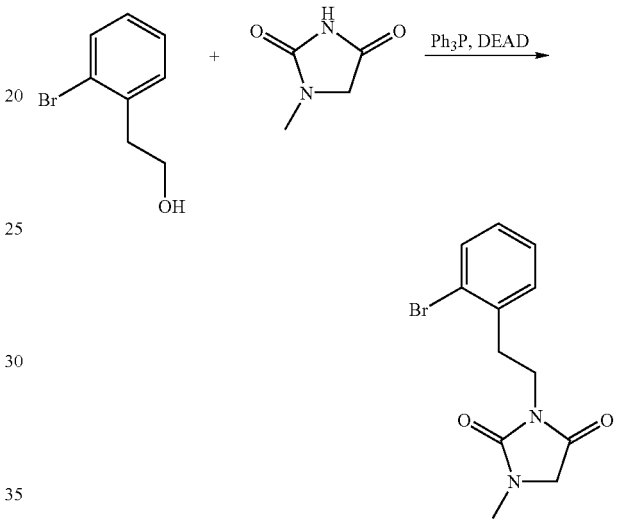

Preparation 36: 3-[2-(2-Bromophenyl)ethyl]-1-methylimidazolidine-2,4-dione (Compound 436)

To a solution of 2-bromophenethyl alcohol (402 mg, 2.0 mmol), 1-methylhydantoin (320 mg, 2.8 mmol) and triphenylphosphine (734 mg, 2.8 mmol) in THF (20 ml) was added diethyl azodicarboxylate solution (40% in toluene, 1.22 ml, 2.8 mmol) at RT. The reaction solution was stirred at the same temperature for 3 h and concentrated in vacuo. The residue was purified by chromatography (petroleum ether/ethyl acetate 1:1) to furnish the title compound as a colorless solid.

$^{13}$C NMR (CDCl$_3$): δ 169.6, 156.7, 137.6, 132.9, 130.9, 128.5, 127.6, 124.6, 51.6, 38.6, 34.4, 29.6

Preparation 37: 3-[2-(2-Bromophenyl)ethyl]-5,5-dimethyloxazolidine-2,4-dione (Compound 437)

2-Bromophenethyl alcohol (402 mg, 2 mmol) and 5,5-dimethyl-oxazolidine-2,4-dione (361 mg, 2.8 mmol) were treated as described in the preparation of compound 436. Purification was done by flash chromatography (petroleum ether/ethyl acetate 4:1) to provide the title compound as a colorless solid.

$^{13}$C NMR (CDCl$_3$): δ 175.7, 154.4, 136.6, 133.1, 131.1, 128.8, 127.5, 124.7, 83.6, 39.2, 33.7, 23.5

Preparation 38: 4-[2-(2-Bromophenyl)ethyl]morpholine-3,5-dione (Compound 438)

2-Bromophenethyl alcohol (402 mg, 2 mmol) and morpholine-3,5-dione (322 mg, 2.8 mmol) were treated as described in the preparation of compound 436. Purification was done by flash chromatography (petroleum ether/ethyl acetate 4:1) to provide the title compound as a colorless solid.

$^{13}$C NMR (CDCl$_3$): δ 168.9, 137.7, 132.9, 131.0, 128.5, 127.5, 124.7, 67.7, 38.2, 34.0

Preparation 39: 1-[2-(2-Bromophenyl)ethyl]piperidine-2,6-dione (Compound 439)

2-Bromophenethyl alcohol (402 mg, 2 mmol) and glutarimide (317 mg, 2.8 mmol) were treated as described in the preparation of compound 436. Purification was done by flash chromatography (petroleum ether/ethyl acetate 2:1) to provide the title compound as a colorless solid.

$^{13}$C NMR (CDCl$_3$): 172.3, 138.3, 132.7, 131.0, 128.2, 127.4, 124.7, 39.0, 34.1, 32.8, 17.1

Preparation 40: 2-Bromobenzyl (triisopropyl)silyl ether (Compound 440)

To a solution of o-bromobenzyl alcohol (2.55 g, 13.6 mmol) and imidazole (1.36 g, 20 mmol) in CH$_2$Cl$_2$ (20 ml) was added triisopropylsilyl chloride (2.6 ml, 12 mmol) at RT. The obtained mixture was stirred at the same temperature for 1 h and then taken up to H$_2$O. After phase separation, the aqueous phase was extracted twice with petroleum ether. The combined organic phases were dried over MgSO$_4$ and concentrated in vacuo. The residue was purified by filtration through a short column of silica gel to give the title compound as a colorless liquid.

$^{13}$C NMR (CDCl$_3$): δ 140.3, 131.7, 127.8, 127.2, 127.1, 120.6, 64.6, 17.9, 11.8

Preparation 41: {2-Chloro-4-[(2-{[(triisopropyl)siloxy]methyl}phenyl)amino]phenyl}(2-methylphenyl)methanone (Compound 441)

A mixture of (4-amino-2-chlorophenyl)(2-methylphenyl)methanone (2.15 g. 8.74 mmol) (disclosed in WO 01/42189 A1) and compound 440 (3.0 g, 8.74 mmol) were treated as described in the preparation of compound 215. Purification was done by flash chromatography (petroleum ether/ethyl acetate 20:1) to provide the title compound as reddish oil.

$^{13}$C NMR (CDCl$_3$): δ 196.2, 147.3, 140.3, 139.1, 137.6, 134.9, 133.4, 131.0, 130.6, 130.6, 129.4, 128.9, 128.7, 128.5, 125.2, 122.4, 119.1, 116.5, 113.2, 65.2, 20.2, 17.8, 17.5

EXAMPLE 1

[2-Chloro-4-({2-[2-(tetrahydro-2H-pyran-2-yloxy)ethyl]phenyl}amino)phenyl](2-methylphenyl)methanone (Compound 101).

A Schlenk tube was charged with (4-amino-2-chlorophenyl)(2-methylphenyl)methanone (9.42 g)(disclosed in WO 01/42189 A1) in 1,4-dioxane (60 mL), compound 401 (12.0 g), Cs$_2$CO$_3$ (17.5 g), Pd$_2$(dba)$_3$ (440 mg), and rac-BINAP (900 mg). The tube was capped with a rubber septum, flushed with argon for 5 min, and then stirred at 100° C. for 72 h. The reaction mixture was allowed to cool to room temperature, then poured into a mixture of water and EtOAc. The aqueous phase was extracted with more EtOAc (×2). The combined organic phases were washed with brine, dried (MgSO$_4$), filtered and concentrated in vacuo. The crude product was purified by chromatography eluting with petroleum ether/ether 2:1 to afford the title compound as an orange semi-solid.

$^{13}$C NMR (CDCl$_3$): δ 196.3, 149.0, 139.6, 139.5, 137.6, 135.3, 133.9, 133.5, 131.1, 130.6, 129.4, 127.8, 127.4, 125.3, 124.4, 122.3, 115.8, 112.1, 99.3, 70.2, 62.3, 32.8, 30.6, 25.2, 20.3, 19.6

EXAMPLE 2

(2-chloro-4-{[2-(2-hydroxyethyl)phenyl]amino}phenyl)(2-methylphenyl)methanone (Compound 102).

A solution of compound 101 (4.00 g) and 4-toluenesulfonic acid (2.54 g) in methanol (25 mL) was stirred for 2 hours at RT. The reaction mixture was poured into a mixture of 1N NaOH and EtOAc. The aqueous phase was extracted with more EtOAc (×2). The combined organic phases were washed with brine, dried (MgSO$_4$), filtered and concentrated in vacuo. The crude product was purified by chromatography eluting with petroleum ether/ether 2:1 followed by 4:1 to afford the title compound as a yellow syrup.

$^{13}$C NMR (CDCl$_3$): δ 196.6, 149.0, 139.5, 137.6, 135.3, 133.8, 133.4, 131.2, 131.2, 130.6, 129.5, 127.8, 127.5, 125.3, 124.6, 122.7, 115.9, 112.2, 65.0, 34.6, 20.3

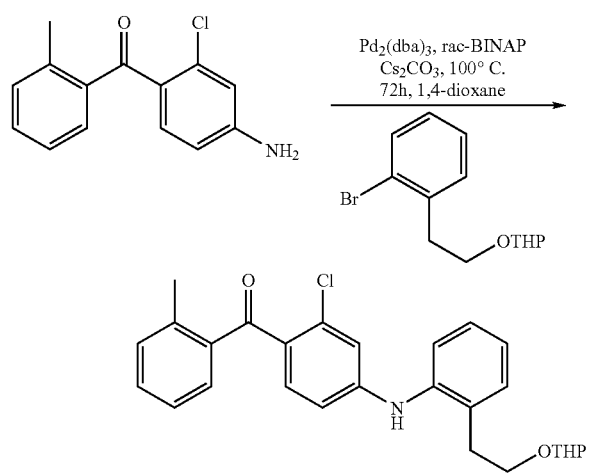

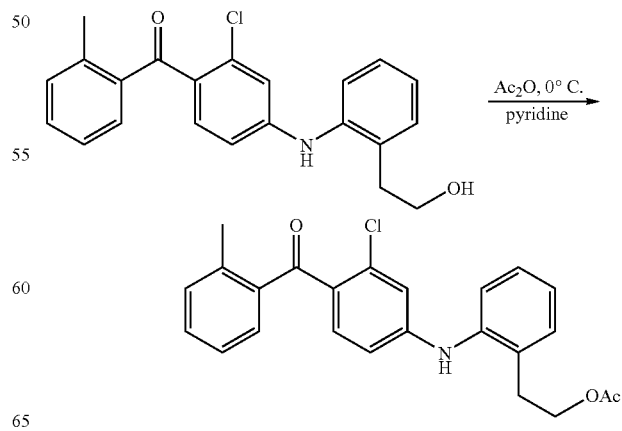

EXAMPLE 3

2-(2-{[3-chloro-4-(2-methylbenzoyl)phenyl]amino}phenyl)ethyl acetate (Compound 103)

Acetic acid anhydride (0.12 mL) was added to a solution of compound 102 (306 mg) in pyridine (3.0 mL) at 0° C. under stirring. The reaction mixture was allowed to come to RT overnight, then poured into a mixture of water and EtOAc. The aqueous phase was extracted with more EtOAc (×2). The combined organic phases were washed with brine, dried (MgSO$_4$), filtered and concentrated in vacuo. The crude product was purified by chromatography eluting with petroleum ether/Et$_2$O 1:1 to afford the title compound as a syrup.

$^{13}$C NMR (CDCl$_3$): δ 196.4, 171.4, 148.8, 139.3, 138.9, 137.8, 135.1, 133.6, 131.2, 131.1, 130.7, 129.6, 128.7, 128.1, 125.3, 124.8, 123.1, 116.1, 112.7, 64.6, 31.2, 21.0, 20.4

EXAMPLE 4

4-(2-{2-[(3-chloro-4-(2-methylbenzoyl)phenyl)amino]phenyl}ethoxy)-4-oxobutanoic acid (Compound 104)

The reaction was carried out as described in the preparation of compound 103, using compound 102 (1.37 g) as the alcohol and succinic anhydride (0.56 g). Purification was done by flash chromatography eluting with a mixture of petroleum ether/EtOAc 4:1 and 5% acetic acid to afford the title compound as a yellow syrup.

$^{13}$C NMR (CDCl$_3$): δ 196.6, 176.3, 172.7, 149.0, 148.6, 139.3, 138.8, 137.8, 135.1, 133.6, 131.2, 131.0, 130.7, 129.6, 128.4, 128.1, 125.3, 125.1, 123.8, 115.9, 112.5, 64.8, 31.0, 29.0, 28.8, 20.4

EXAMPLE 5

2-(2-{[3-chloro-4-(2-methylbenzoyl)phenyl]amino}phenyl)ethyl hexanoate (Compound 105)

The reaction was carried out as described in the preparation of compound 103, using compound 102 (0.42 g) as the alcohol and hexanoic anhydride (0.40 mL). The combined organic phases were also washed with 0.5 N NaOH. Purification was done by flash chromatography eluting successively with petroleum ether/EtOAc 9:1 and petroleum ether/EtOAc 4:1 to afford the title compound as a yellow syrup.

$^{13}$C NMR (CDCl$_3$): δ 196.4, 174.3, 148.8, 139.3, 138.9, 137.8, 135.2, 133.6, 131.2, 131.1, 130.8, 130.7, 129.6, 128.6, 128.0, 125.3, 124.8, 123.2, 116.1, 112.6, 64.4, 34.3, 31.3, 24.6, 24.4, 22.3, 20.4, 13.9

EXAMPLE 6

2-(2-{[3-chloro-4-(2-methylbenzoyl)phenyl]amino}phenyl)-1-methylethyl acetate (Compound 106)

The reaction was carried out as described in the preparation of compound 101, using compound 402 (304 mg) as the bromide. Purification was done by flash chromatography eluting with a mixture of petroleum ether/EtOAc 4:1 to afford the title compound as an orange syrup.

$^{13}$C NMR (CDCl$_3$): δ 196.5, 171.7, 148.5, 139.4, 139.3, 137.8, 135.1, 133.6, 131.7, 131.2, 130.7, 129.6, 129.0, 128.8, 127.9, 125.3, 123.7, 121.5, 116.4, 113.2, 71.6, 39.0, 21.4, 20.4, 19.1

EXAMPLE 7

(2-chloro-4-{[2-(2-hydroxypropyl)phenyl]amino}phenyl)(2-methylphenyl)methanone (Compound 107)

A solution of compound 106 (49 mg) in THF (1.0 mL) was added a solution of sodium methoxide in methanol (3.0 mL, 0.33 M) and then stirred for 45 min. at 20° C. The reaction mixture was poured into a mixture of water and EtOAc. The aqueous phase was extracted with more EtOAc (×2). The combined organic phases were washed with brine, dried (MgSO$_4$), filtered and concentrated in vacuo to afford the title compound as a yellow syrup.

$^{13}$C NMR (CDCl$_3$): δ 196.5, 148.9, 139.7, 139.6, 137.6, 135.3, 133.9, 132.0, 132.0, 131.1, 130.6, 129.4, 127.7, 127.5, 125.3, 124.1, 122.3, 116.0, 112.3, 70.6, 40.6, 23.8, 20.3

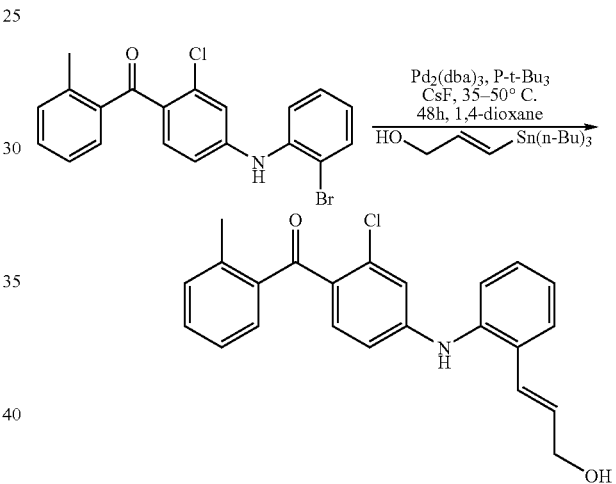

EXAMPLE 8

[2-chloro-4-({2-[(1E)-3-hydroxyprop-1-enyl]phenyl}amino)phenyl](2-methylphenyl)methanone (Compound 108)

Under an atmosphere of argon, a solution of {2-chloro-4-[(2-bromophenyl)amino]phenyl}(2-methylphenyl)methanone (300 mg) (disclosed in WO 01/42189) in dioxane (1.5 mL) and a solution of P-t-Bu$_3$ (18 mg) in dioxane (1.0 mL) were added in turn to a Schlenk tube charged with Pd$_2$(dba)$_3$ (21 mg) and CsF (152 mg). (2E)-3-(tributylstannyl)prop-2-en-1-ol (273 mg) was then added by syringe, and the Schlenk tube was sealed, placed in an 35–50° C. oil bath, and stirred for 48 h. The reaction mixture was then cooled to room temperature, diluted with acetonitrile, and filtered through a pad of celite. The celite was washed with acetonitrile, and the combined organic phase was then washed thoroughly with petroleum ether and concentrated in vacuo. The product was purified by flash chromatography eluting with a mixture of petroleum ether/EtOAc 4:1 to afford the title compound as a yellow syrup.

$^{13}$C NMR (CDCl$_3$): δ 196.8, 149.0, 139.2, 137.7, 137.2, 135.1, 133.6, 131.9, 131.5, 131.2, 130.8, 129.6, 128.6, 128.4, 127.4, 126.0, 125.4, 125.4, 124.0, 116.1, 112.5, 63.4, 20.4

EXAMPLE 9

(2-chloro-4-{[2-(3-hydroxypropyl)phenyl] amino}phenyl)(2-methylphenyl)methanone (Compound 109)

A mixture of compound 108 (50 mg) and 10% Pd/C (7 mg) in ethanol (1.0 mL) was stirred under an atmosphere of hydrogen at room temperature for 8 h. The Reaction mixture was concentrated in vacuo and purified by flash chromatography eluting with a mixture of DCM/MeOH 97:3 to afford the title compound as a yellow syrup.

$^{13}$C NMR (CDCl$_3$): δ 196.5, 149.4, 139.5, 138.7, 137.7, 135.2, 134.7, 133.8, 131.2, 130.7, 130.6, 129.5, 128.0, 127.1, 125.3, 124.9, 123.1, 115.8, 112.2, 60.9, 32.8, 26.6, 20.4

EXAMPLE 10

[2-chloro-4-({2-[(1E)-4-hydroxybut-1-enyl] phenyl}amino)phenyl](2-methylphenyl)methanone (Compound 110)

The reaction was carried out as described in the preparation of compound 108, using (2E)-4-(tributylstannyl)but-3-en-1-ol (304 mg) as the stannane. Purification was done by flash chromatography eluting with a mixture of petroleum ether/EtOAc 8:1 followed by 1:1 to afford the title compound as a yellow syrup.

$^{13}$C NMR (CDCl$_3$): δ 196.5, 149.0, 139.3, 137.8, 136.8, 135.1, 133.6, 131.2, 130.8, 129.8, 129.6, 128.3, 127.9, 127.3, 125.5, 125.3, 124.2, 116.0, 112.4, 61.9, 36.6, 20.4

EXAMPLE 11

[4-({2-[(1E)-3-aminoprop-1-enyl]phenyl}amino)-2-chlorophenyl](2-methylphenyl)methanone (Compound 111)

The reaction was carried out as described in the preparation of compound 108, using (2E)-3-(tributylstannyl)prop-2-en-1-amine (273 mg) as the stannane. Purification was done by flash chromatography eluting with a mixture of DCM/MeOH/Et$_3$N 90:5:5 to afford the title compound as a yellow foam.

$^{13}$C NMR (CDCl$_3$): δ 196.5, 149.0, 139.3, 137.8, 137.1, 135.1, 133.6, 132.2, 131.2, 130.8, 129.6, 128.5, 128.4, 127.4, 125.4, 125.3, 125.2, 123.9, 116.2, 112.5, 44.2, 20.4

EXAMPLE 12 diethyl (2E)-3-(2-{[3-chloro-4-(2-methylbenzoyl) phenyl]amino}phenyl)prop-2-enylphosphonate (Compound 112)

The reaction was carried out as described in the preparation of compound 108, using diethyl (2E)-3-(tributylstannyl) prop-2-enylphosphonate (219 mg) as the stannane. Purification was done by flash chromatography eluting with a mixture of petroleum ether/EtOAc 1:1 to afford the title compound.

$^{13}$C NMR (CDCl$_3$): δ 196.4, 148.9, 139.3, 137.8, 137.1, 135.1, 133.6, 132.0, 131.2, 130.8, 130.3, 130.1, 129.6, 128.7, 127.4, 125.3, 123.9, 122.2, 122.0, 116.1, 112.5, 62.1, 31.3, 20.4, 16.5

EXAMPLE 13

[2-chloro-4-({2-[(1E)-3-hydroxy-3-methylbut-1-enyl]phenyl}amino)phenyl](2-methylphenyl)methanone (Compound 113)

The reaction was carried out as described in the preparation of compound 108, using compound 403 (295 mg) as the stannane. Purification was done by flash chromatography eluting with a mixture of petroleum ether/EtOAc 2:1 to afford the title compound as a syrup.

$^{13}$C NMR (CDCl$_3$): δ 196.5, 148.8, 140.5, 139.3, 137.8, 137.2, 135.0, 133.5, 132.1, 131.2, 130.8, 129.6, 128.7, 128.5, 127.4, 125.5, 125.3, 124.1, 121.8, 116.2, 112.7, 71.2, 30.0, 20.4

EXAMPLE 14 ethyl (2E)-3-(2-{[3-chloro-4-(2-methylbenzoyl)phenyl]amino}phenyl)acrylate (Compound 114)

The reaction was carried out as described in the preparation of compound 108, using diethyl (2E)-3-(tributylstannyl) acrylate (295 mg) as the stannane. Purification was done by flash chromatography eluting with a mixture of petroleum ether/EtOAc 6:1 to afford the title compound as a yellow syrup.

$^{13}$C NMR (CDCl$_3$): δ 196.5, 167.2, 148.2, 139.7, 139.3, 139.0, 138.0, 135.0, 133.4, 131.3, 130.9, 129.8, 129.6, 129.0, 128.0, 125.4, 125.3, 123.9, 119.9, 116.8, 113.3, 51.8, 20.5

EXAMPLE 15

(2E)-3-(2-{[3-chloro-4-(2-methylbenzoyl)phenyl] amino}phenyl)acrylic acid (Compound 115)

A solution of compound 114 (190 mg) in THF (2.0 mL) was added a solution of lithium hydroxide (22 mg) in a mixture of MeOH/H$_2$O (3:4; 3.5 mL) and then stirred for 72 h at 20° C. The reaction mixture was poured into a mixture of 1N HCl (aq.) and DCM. The aqueous phase was extracted with more DCM (×3). The combined organic phases were washed with brine, dried (Na$_2$SO$_4$), filtered and concentrated in vacuo to afford the crude product as a solid. Crystallization from EtOAc afforded the title compound as yellow crystals.

$^{13}$C NMR (DMSO-d$_6$): δ 195.2, 167.5, 149.8, 139.3, 139.2, 139.1, 136.5, 133.5, 131.2, 131.0, 130.7, 128.9, 128.9, 127.7, 126.7, 125.6, 125.2, 124.8, 120.0, 115.1, 112.1, 19.7

EXAMPLE 16

{2-chloro-4-[(2-{(1E)-3-[(2,2-dimethyl-1,3-dioxolan-4-yl)methoxy]prop-1-enyl}phenyl)amino]phenyl}(2-methylphenyl)methanone (Compound 116)

The reaction was carried out as described in the preparation of compound 108, using compound 404 (351 mg) as the stannane. Purification was done by flash chromatography eluting with a mixture of petroleum ether/EtOAc 2:1 to afford the title compound as a yellow syrup.

$^{13}$C NMR (CDCl$_3$): δ 196.4, 148.8, 139.3, 137.9, 137.2, 135.1, 133.5, 131.9, 131.3, 130.8, 129.6, 128.9, 128.8, 127.5, 125.5, 125.4, 124.1, 116.2, 112.6, 109.5, 74.8, 72.1, 71.4, 66.7, 26.8, 25.4, 20.4

EXAMPLE 17

[2-chloro-4-({2-[(1E)-3-(2,3-dihydroxypropoxy)prop-1-enyl]phenyl}amino)phenyl](2-methylphenyl)methanone (Compound 117)

A solution of compound 116 (70 mg) in a mixture of THF (1.0 mL) and aq. HCl (1.0 mL, 1 N) was stirred at 20° C. for 24 h. The reaction mixture was poured into a mixture of water and EtOAc. The organic phase was dried (MgSO$_4$), filtered and concentrated in vacuo. The crude product was purified by chromatography eluting with a mixture of DCM/MeOH 95:5 to afford the title compound as a yellow syrup.

$^{13}$C NMR (CDCl$_3$): δ 196.9, 149.2, 139.1, 137.9, 137.3, 135.0, 133.5, 131.9, 131.3, 130.9, 129.7, 128.8, 128.4, 128.1, 127.9, 127.3, 125.6, 125.4, 124.5, 116.0, 112.4, 71.8, 71.7, 70.7, 63.9, 20.4

$^{13}$C NMR (CDCl$_3$): δ 196.8, 171.4, 156.2, 149.0, 139.2, 137.9, 137.3, 135.0, 133.5, 131.3, 131.2, 130.9, 129.7, 128.7, 128.4, 127.6, 127.2, 126.8, 125.4, 125.1, 123.7, 116.2, 112.6, 80.7, 62.8, 55.5, 41.5, 28.3, 20.4

EXAMPLE 19 methyl O-(tert-butyl)-N-({[(2E)-3-(2-{[3-chloro-4-(2-methylbenzoyl)phenyl]amino}phenyl)prop-2-enyl]amino}carbonyl)-L-serinate (Compound 119)

A mixture of methyl O-(t-butyl)-N-(oxomethylene)-L-serinate (40 mg) and compound 111 (50 mg) in DCM (3.0 mL) was stirred at 20° C. for 1 h. Ethylamine (20 mg) was added and the reaction mixture was stirred for 2 h. Concentration in vacuo followed by chromatography eluting with petroleum ether/EtOAc 2:1 afforded the title compound as a yellow foam.

$^{13}$C NMR (CDCl$_3$): δ 196.5, 172.9, 158.1, 149.3, 139.5, 137.7, 137.6, 134.9, 133.6, 131.2, 131.1, 130.6, 129.5, 129.0, 128.3, 127.9, 127.2, 126.3, 125.3, 124.5, 123.0, 116.6, 112.7, 73.5, 62.4, 54.0, 52.4, 46.1, 27.3, 20.4

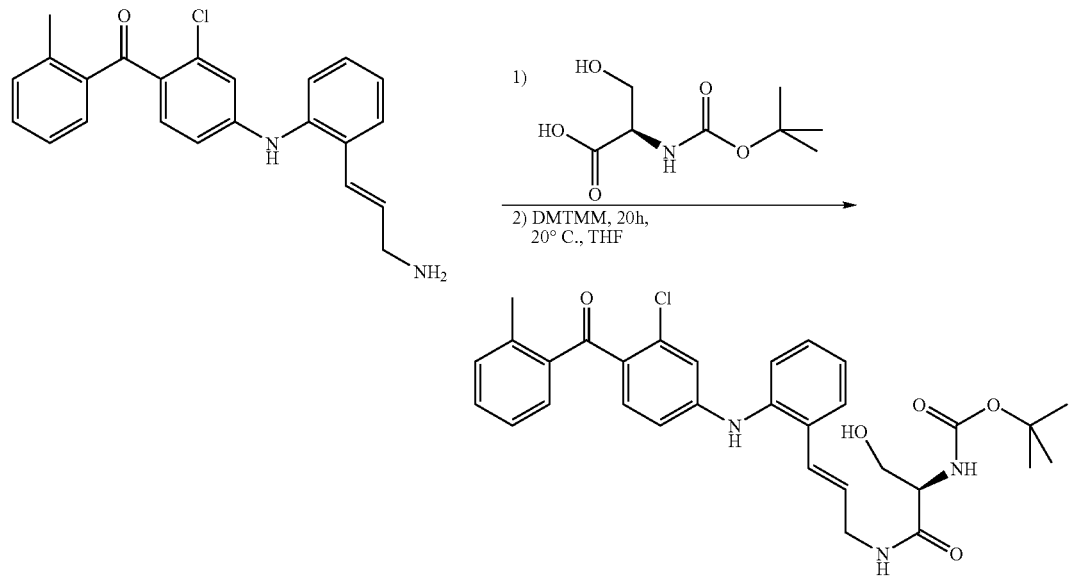

EXAMPLE 18 tert-butyl (1R)-2-{[(2E)-3-(2-{[3-chloro-4-(2-methylbenzoyl)phenyl]amino}phenyl)prop-2-enyl]amino}-1-(hydroxymethyl)-2-oxoethylcarbamate (Compound 118)

A mixture of N-(t-butoxycarbonyl)-L-serine (30 mg) and compound 111 (50 mg) in THF (1.0 mL) was stirred at 20° C. for 10 min. DMTMM (40 mg) was added to the mixture and stirred for 20 h at 20° C. The reaction mixture was poured into water and extracted with EtOAc (×3). The organic phase was combined and washed with brine and dried with MgSO$_4$. The crude product was purified by chromatography eluting with EtOAc/trifluoroacetic acid 99:1 to afford the title compound as a yellow foam.

EXAMPLE 20

N-(tert-butyl)-N'-[(2E)-3-(2-{[3-chloro-4-(2-methylbenzoyl)phenyl]amino}phenyl)prop-2-enyl]thiourea (Compound 120)

A mixture of t-butyl isothiocyanate (19 mg) and compound 111 (50 mg) in DCM (3.0 mL) was stirred at 20° C. for 1.5 h. Ethylamine (20 mg) was added and the reaction mixture was stirred for 24 h. Concentration in vacuo followed by chromatography eluting with petroleum ether/EtOAc 3:1 afforded the title compound.

$^{13}$C NMR (CDCl$_3$): δ 196.6, 181.4, 149.0, 139.2, 137.8, 137.2, 135.0, 133.6, 131.9, 131.3, 130.8, 129.6, 128.8, 128.5, 127.9, 127.8, 127.4, 125.5, 125.4, 124.0, 116.1, 112.5, 53.0, 47.5, 29.5, 20.4

EXAMPLE 21

N-[(2E)-3-(2-{[3-chloro-4-(2-methylbenzoyl)phenyl]amino}phenyl)prop-2-enyl]-4-oxopentanamide (Compound 121)

The reaction was carried out as described in the preparation of compound 118, using 4-oxopetanoic acid (25 mg) as the carboxylic acid. Purification was done by flash chromatography eluting with a mixture of petroleum ether/EtOAc 2:3 to afford the title compound.

$^{13}$C NMR (CDCl$_3$): δ 208.5, 196.5, 172.0, 149.1, 139.4, 137.8, 137.3, 135.0, 133.6, 131.2, 131.0, 130.7, 129.6, 128.4, 128.4, 128.2, 127.1, 125.7, 125.3, 124.9, 123.4, 116.5, 112.6, 41.3, 38.6, 29.9, 20.4

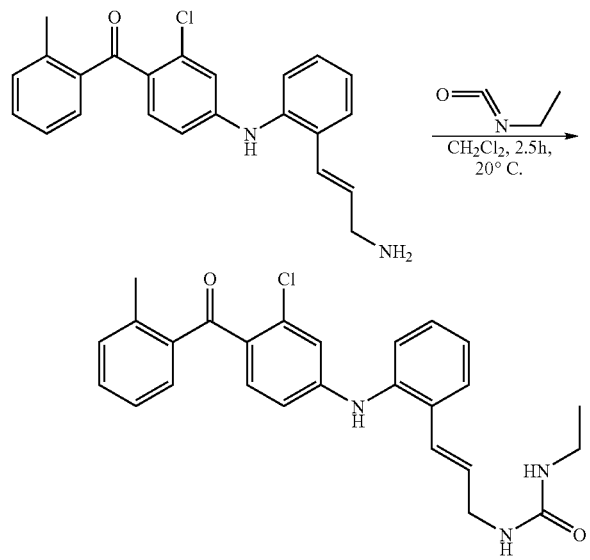

EXAMPLE 22

N-[(2E)-3-(2-{[3-chloro-4-(2-methylbenzoyl)phenyl]amino}phenyl)prop-2-enyl]-N'-ethylurea (Compound 122)

A mixture of ethyl isocyanate (28 mg) and compound 111 (100 mg) in DCM (1.0 mL) was stirred at 20° C. for 2.5 h. The reaction mixture was poured into water and extracted with DCM (×3). The organic phases were combined and washed with brine and dried with MgSO$_4$. The crude product was purified by chromatography eluting with petroleum ether/EtOAc 2:3 to afford the title compound as a yellow syrup.

$^{13}$C NMR (CDCl$_3$): δ 197.0, 158.7, 149.5, 139.2, 137.7, 137.1, 134.9, 133.6, 132.1, 131.3, 130.9, 129.9, 129.6, 128.4, 127.8, 127.3, 126.5, 125.4, 125.4, 124.2, 116.2, 112.3, 42.5, 35.2, 20.4, 15.5

EXAMPLE 23

Ethyl 4-{[(2E)-3-(2-{[3-chloro-4-(2-methylbenzoyl)phenyl]amino}phenyl)prop-2-enyl]amino}-4-oxobutanoate (Compound 123)

The reaction was carried out as described in the preparation of compound 118, using ethyl hydrogen succinate (32 mg) as the carboxylic acid. Purification was done by flash chromatography eluting with a mixture of DCM/MeOH 95:5 to afford the title compound as a syrup.

$^{13}$C NMR (CDCl$_3$): δ 196.6, 173.3, 171.7, 149.2, 139.3, 137.7, 137.3, 135.0, 133.6, 131.4, 131.2, 130.8, 129.6, 128.5, 128.3, 128.2, 127.2, 126.5, 125.4, 125.2, 123.8, 116.2, 112.5, 60.9, 41.6, 30.9, 29.5, 20.4, 14.1

EXAMPLE 24

N-[(2E)-3-(2-{[3-chloro-4-(2-methylbenzoyl)phenyl]amino}phenyl)prop-2-enyl]-N'-cyclohexylurea (Compound 124)

The reaction was carried out as described in the preparation of compound 122, using cyclohexyl isocyanate (40 mg). Purification was done by flash chromatography eluting with a mixture of petroleum ether/EtOAc 1:1 to afford the title compound as a syrup.

$^{13}$C NMR (CDCl$_3$): δ 196.8, 157.8, 149.2, 139.2, 137.8, 137.1, 134.9, 133.5, 132.0, 131.3, 130.9, 130.0, 129.7, 128.5, 128.1, 127.4, 126.7, 125.4, 125.3, 124.0, 116.3, 112.5, 49.1, 42.6, 33.9, 25.6, 25.0, 20.4

EXAMPLE 25

N'-[(2E)-3-(2-{[3-chloro-4-(2-methylbenzoyl)phenyl]amino}phenyl)prop-2-enyl]-N,N-dimethylsuccinamide (Compound 125)

The reaction was carried out as described in the preparation of compound 118, using N,N-dimethylsuccinamic acid (32 mg) as the carboxylic acid. Purification was done by flash chromatography eluting with a mixture of EtOAc/MeOH 95:5 to afford the title compound as a syrup.

$^{13}$C NMR (CDCl$_3$): δ 196.5, 172.7, 172.1, 149.6, 139.6, 137.6, 137.5, 135.1, 133.7, 131.1, 130.6, 129.4, 128.2, 127.8, 126.9, 125.6, 125.3, 124.7, 123.5, 116.1, 112.3, 41.4, 37.1, 35.7, 31.2, 28.6, 20.3

EXAMPLE 26

Dimethyl [(2E)-3-(2-{[3-chloro-4-(2-methylbenzoyl)phenyl]amino}phenyl)prop-2-enyl]malonate (Compound 126)

The reaction was carried out as described in the preparation of compound 108, using compound 405 (300 mg) as the stannane. Purification was done by flash chromatography eluting with a mixture of petroleum ether/EtOAc 6:1 to afford the title compound as a yellow syrup.

$^{13}$C NMR (CDCl$_3$): δ 196.4, 169.2, 148.6, 139.3, 137.8, 137.1, 135.1, 133.6, 131.8, 131.2, 130.8, 129.6, 129.0, 128.7, 128.5, 127.7, 125.3, 125.0, 123.1, 116.2, 112.6, 52.6, 51.6, 32.4, 20.4

EXAMPLE 27

[2-chloro-4-({2-[(1E)-3-morpholin-4-ylprop-1-enyl]phenyl}amino)phenyl](2-methylphenyl)methanone (Compound 127)

The reaction was carried out as described in the preparation of compound 108, using compound 406 (466 mg) as the stannane. Purification was done by flash chromatography eluting with EtOAc to afford the title compound as a yellow foam.

$^{13}$C NMR (CDCl$_3$): δ 196.4, 149.0, 139.3, 137.8, 136.9, 135.1, 133.5, 132.4, 131.3, 130.8, 129.6, 128.9, 128.7, 128.7, 127.3, 125.8, 125.4, 124.6, 115.9, 112.5, 66.9, 61.5, 53.7, 20.4

EXAMPLE 28

6-O-[(2E)-3-(2-{[3-chloro-4-(2-methylbenzoyl)phenyl]amino}phenyl)prop-2-enyl]-1,2:3,4-di-O-(1-methylethylidene)-a-D-galactopyranose (Compound 128)

The reaction was carried out as described in the preparation of compound 108, using compound 407 (400 mg) as the stannane. Purification was done by flash chromatography eluting with a mixture of petroleum ether/EtOAc 5:1 to afford the title compound as a yellow syrup.

$^{13}$C NMR (CDCl$_3$): δ 196.4, 148.7, 139.3, 137.8, 137.3, 135.1, 133.6, 131.6, 131.2, 130.7, 129.6, 129.3, 128.7, 128.6, 127.6, 127.3, 125.3, 125.1, 123.5, 116.3, 112.6, 109.4, 108.6, 96.4, 71.8, 71.3, 70.7, 70.5, 69.4, 67.1, 26.1, 26.0, 24.9, 24.5, 20.4

EXAMPLE 29

Methyl 5-O-[(2E)-3-(2-{[3-chloro-4-(2-methylbenzoyl)phenyl]amino}phenyl)prop-2-enyl]-2,3-O-(1-methylethylidene)-β-D-ribofuranoside (Compound 129)

The reaction was carried out as described in the preparation of compound 108, using compound 408 (427 mg) as the stannane. Purification was done by flash chromatography eluting with a mixture of petroleum ether/EtOAc 6:1 to afford the title compound as a yellow syrup.

$^{13}$C NMR (CDCl$_3$): δ 196.4, 148.8, 139.3, 137.8, 137.2, 135.1, 133.6, 131.7, 131.2, 130.8, 129.6, 129.0, 128.8, 127.5, 127.4, 125.4, 125.3, 123.9, 116.2, 112.6, 112.5, 109.4, 85.2, 82.1, 71.8, 71.5, 54.9, 26.5, 25.0, 20.4

EXAMPLE 30 methyl 5-O-[(2E)-3-(2-{[3-chloro-4-(2-methylbenzoyl)phenyl]amino}phenyl)prop-2-enyl]-β-D-ribofuranoside (Compound 130)

Compound 129 (50 mg) was dissolved in 80% aqueous acetic acid (1.0 mL) and the mixture was stirred for 7 days at 50° C. The reaction mixture was poured into saturated aqueous Na$_2$CO$_3$ (10 mL) and the aqueous phase was extracted with EtOAc (3×10 mL). The combined organic phases were dried (Na$_2$SO$_4$), filtered and evaporated in vacuo. Purification was done by flash chromatography eluting with a mixture of petroleum ether/EtOAc 1:4 to afford the title compound as a yellow foam.

$^{13}$C NMR (CDCl$_3$): δ 197.4, 149.2, 138.8, 138.2, 137.0, 134.9, 133.3, 132.4, 131.4, 131.1, 130.1, 128.8, 128.7, 127.4, 127.3, 125.9, 125.4, 124.8, 116.0, 112.4, 108.4, 81.7, 75.1, 72.4, 71.9, 71.7, 55.3, 20.6

EXAMPLE 31

Methyl (4E)-5-(2-{[3-chloro-4-(2-methylbenzoyl)phenyl]amino}phenyl)-2-(methylsulfonyl)pent-4-enoate (Compound 131)

The reaction was carried out as described in the preparation of compound 108, using compound 409 (250 mg) as the stannane. Purification was done by flash chromatography eluting with a mixture of petroleum ether/EtOAc 3:1 to afford the title compound as a syrup.

$^{13}$C NMR (CDCl$_3$): δ 196.4, 166.5, 148.6, 139.2, 137.9, 137.3, 135.0, 133.5, 131.5, 131.3, 130.8, 130.2, 129.7, 128.9, 128.9, 127.6, 126.1, 125.4, 125.3, 123.8, 116.1, 112.6, 68.8, 53.5, 39.4, 30.4, 20.4

EXAMPLE 32

Ethyl {[(2E)-3-(2-{[3-chloro-4-(2-methylbenzoyl)phenyl]amino}phenyl)prop-2-enyl]thio}acetate (Compound 132)

The reaction was carried out as described in the preparation of compound 108, using compound 410 (300 mg) as the stannane. Purification was done by flash chromatography eluting with a mixture of petroleum ether/EtOAc 10:1 to afford the title compound as a syrup.

$^{13}$C NMR (CDCl$_3$): δ 196.4, 171.0, 148.6, 139.3, 137.8, 137.5, 135.1, 133.6, 131.2, 131.0, 130.7, 129.6, 129.3, 128.7, 127.5, 127.0, 125.3, 124.8, 122.9, 116.4, 112.6, 61.6, 35.2, 32.4, 20.4, 14.1

EXAMPLE 33

[2-chloro-4-{[2-((1E)-3-{bis[2-(acetyloxy)ethyl]amino}prop-1-enyl)phenyl]amino}phenyl](2-methylphenyl)methanone (Compound 133)

The reaction was carried out as described in the preparation of compound 108, using compound 412 (454 mg) as the stannane. Purification was done by flash chromatography eluting with a mixture of petroleum ether/EtOAc 1:2 to afford the title compound as a foam.

$^{13}$C NMR (CDCl$_3$): δ 196.4, 171.2, 149.0, 139.4, 137.8, 137.4, 135.1, 133.6, 131.9, 131.2, 130.7, 129.7, 129.6, 128.5, 128.3, 127.5, 125.3, 125.1, 123.5, 116.4, 112.6, 62.4, 57.6, 52.8, 21.0, 20.4

EXAMPLE 34

[2-chloro-4-{[2-((1E)-3-{bis[2-(hydroxy)ethyl]amino}prop-1-enyl)phenyl]amino}phenyl](2-methylphenyl)methanone (Compound 134)

The reaction was carried out as described in the preparation of compound 107, using compound 133 (172 mg) as the ester. Purification was done by flash chromatography eluting with a mixture of DCM/MeOH 10:1 to afford the title compound as a yellow syrup.

$^{13}$C NMR (CDCl$_3$): δ 196.6, 149.1, 139.2, 137.9, 137.1, 135.0, 133.5, 132.0, 131.3, 130.8, 129.7, 129.2, 128.6, 128.6, 128.5, 127.4, 125.4, 125.3, 124.0, 116.1, 112.6, 59.6, 57.0, 56.0, 20.4

EXAMPLE 35

(2-Chloro-4-{[2-((1E)-3-{4-[2-(acetyloxy)ethyl]piperidin-1-yl}prop-1-enyl)phenyl]amino}phenyl)(2-methylphenyl)methanone (Compound 135)

The reaction was carried out as described in the preparation of compound 108, using compound 413 (280 mg) as the stannane. Purification was done by flash chromatography eluting with EtOAc to afford the title compound as a foam.

$^{13}$C NMR (CDCl$_3$): δ 196.5, 171.1, 149.0, 139.3, 137.8, 137.0, 135.1, 133.5, 132.3, 131.2, 130.8, 129.6, 129.1, 128.7, 128.6, 127.3, 125.6, 125.3, 124.4, 116.0, 112.5, 62.4, 61.3, 53.8, 35.1, 32.5, 31.9, 21.0, 20.4

EXAMPLE 36

{2-Chloro-4-[(2-{(1E)-3-[4-(2-hydroxyethyl)piperidin-1-yl]prop-1-enyl}phenyl)amino]phenyl}(2-methylphenyl)methanone (Compound 136)

The reaction was carried out as described in the preparation of compound 107, using compound 135 (170 mg) as the ester. Purification was done by flash chromatography eluting with a mixture of DCM/MeOH 17:3 to afford the title compound as a yellow solid.

$^{13}$C NMR (CDCl$_3$): δ 196.6, 149.0, 139.3, 137.8, 137.5, 135.0, 133.5, 131.4, 131.2, 130.8, 129.6, 128.9, 128.5, 127.3, 125.3, 125.2, 123.9, 116.1, 112.7, 60.6, 60.1, 53.5, 38.8, 31.7, 31.1, 20.4

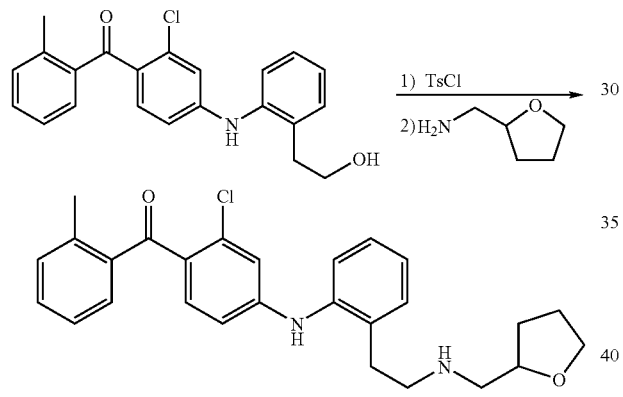

EXAMPLE 37

{2-Chloro-4-[(2-{2-[(tetrahydrofuran-2-ylmethyl)amino]ethyl}phenyl)amino]phenyl}(2-methylphenyl)methanone (Compound 137)

Compound 102 (0.15 g, 0.41 mmol) was dissolved in pyridine (0.2 mL) at 0° C., and p-toluenesulfonyl chloride (0.086 g, 0.45 mmol) was added. The suspension was stirred for 45 min at 0° C., after which the amine (tetrahydrofurfuryl amine, 0.127 mL, 1.23 mmol) was added. The reaction mixture was stirred at room temperature for 18 h. H$_2$O (10 mL) was added and the aqueous phase was extracted with EtOAc (5×10 mL). The combined organic phases were washed with brine, dried (MgSO$_4$), filtered and evaporated in vacuo. The crude product was purified by flash chromatography using EtOAc/MeOH/Et$_3$N 10:1:0.1 as the eluent to afford the title compound as a yellow oil.

$^{13}$C NMR (CDCl$_3$): δ 196.4, 149.3, 139.9, 137.5, 135.3, 134.4, 134.0, 131.2, 131.1, 130.4, 129.3, 127.3, 127.2, 125.3, 123.8, 121.8, 116.2, 112.1, 78.0, 68.0, 54.6, 51.7, 33.5, 29.4, 25.7, 20.3

EXAMPLE 38

[2-Chloro-4-({2-[2-(4-methylpiperazin-1-yl)ethyl]phenyl}amino)phenyl](2-methylphenyl)methanone (Compound 138)

The reaction was carried out as described in the preparation of compound 137, using 1-methylpiperazine (0.137 mL, 1.23 mmol) as the amine. Work up was conducted as described in the preparation of compound 137, and the crude product was purified by flash chromatography eluting with EtOAc/EtOH/Et$_3$N 7:1:0.5. This afforded the title compound as a yellow oil.

$^{13}$C NMR (CDCl$_3$): δ 196.3, 149.1, 139.8, 139.6, 137.7, 135.3, 134.7, 133.8, 131.2, 130.6, 129.4, 128.0, 127.2, 125.3, 123.8, 121.4, 116.8, 112.8, 60.8, 55.2, 54.0, 46.1, 30.9, 20.4

EXAMPLE 39

{2-Chloro-4-[(2-{2-[(3-morpholin-4-ylpropyl)amino]ethyl}phenyl)amino]phenyl}(2-methylphenyl)methanone (Compound 139)

The reaction was carried out as described in the preparation of compound 137, using 1-morpholino-3-aminopropane (0.18 mL, 1.23 mmol) as the amine. Work up was conducted as described in the preparation of compound 137, and the crude product was purified by flash chromatography eluting with EtOAc/EtOH/Et$_3$N 5:1:0.5. This afforded the title compound as an orange oil.

$^{13}$C NMR (CDCl$_3$): δ 196.7, 149.6, 140.2, 140.0, 137.9, 135.7, 134.3, 133.9, 131.5, 131.4, 130.9, 129.8, 127.9, 127.8, 125.7, 124.4, 122.6, 116.4, 112.6, 67.2, 57.9, 54.2, 51.4, 49.5, 33.0, 26.1, 20.7

EXAMPLE 40

(2-Chloro-4-{[2-(2-{[2-(dimethylamino)ethyl]amino}ethyl)phenyl]amino}phenyl)(2-methylphenyl)methanone (Compound 140)

The reaction was carried out as described in the preparation of compound 137, using 2-dimethylamino-ethylamine (0.13 mL, 1.23 mmol) as the amine. Work up was conducted as described in the preparation of compound 137, and the crude product was purified by flash chromatography eluting with EtOAc/EtOH/Et$_3$N 4 1:0.5. This afforded the title compound as a yellow oil.

$^{13}$C NMR (CDCl$_3$): δ 196.4, 149.4, 139.8, 139.8, 137.5, 135.3, 133.9, 131.1, 131.1, 130.5, 129.4, 127.4, 125.3, 123.9, 121.9, 116.2, 112.1, 58.2, 51.2, 47.0, 45.3, 33.0, 20.3

EXAMPLE 41

{2-Chloro-4-[(2-{2-[(2-methoxyethyl)amino]ethyl}phenyl)amino]phenyl}(2-methylphenyl)methanone (Compound 141)

The reaction was carried out as described in the preparation of compound 137, using 2-methoxy-ethylamine (0.11 mL, 1.23 mmol) as the amine. Work up was conducted as described in the preparation of compound 137, and the crude product was purified by flash chromatography eluting with EtOAc/MeOH/Et$_3$N 4:1:0.5. This afforded the title compound as a yellow oil.

$^{13}$C NMR (CDCl$_3$): δ 196.4, 149.2, 139.8, 139.8, 137.5, 135.3, 134.2, 133.9, 131.2, 131.1, 130.5, 129.4, 127.4, 127.3, 125.3, 123.8, 121.7, 116.2, 112.1, 71.5, 58.9, 51.4, 49.4, 33.3, 20.3

EXAMPLE 42

1-[3-({2-[2-({3-Chloro-4-[(2-methylphenyl)carbonyl]phenyl}amino)phenyl]ethyl}amino)propyl]pyrrolidin-2-one (Compound 142)

Compound 102 (0.15 g, 0.41 mmol) was dissolved in pyridine (0.2 mL) at 3° C., and p-toluenesulfonyl chloride (0.086 g, 0.45 mmol) was added. The suspension was stirred for 45 min at 3° C., after which the amine (1-(3-aminopropyl)-2-pyrrolidinon, 0.18 mL, 1.23 mmol) was added. The reaction mixture was stirred at 3° C. for 3 days. Work up was conducted as described in the preparation of compound 137, and the crude product was purified by flash chromatography eluting with EtOAc/EtOH/Et$_3$N 4:1:0.5. This afforded the title compound as a yellow oil.

$^{13}$C NMR (CDCl$_3$): δ 196.4, 175.5, 149.3, 139.7, 139.6, 137.5, 135.2, 134.0, 134.0, 131.2, 131.1, 130.5, 129.4, 127.4, 127.3, 125.3, 124.0, 122.0, 116.0, 112.2, 51.0, 47.2, 46.6, 39.9, 33.0, 30.9, 27.0, 20.3, 17.9

EXAMPLE 43

{2-Chloro-4-[(2-{2-[methyl(tetrahydrofuran-2-ylmethyl)amino]ethyl}phenyl)amino]phenyl}(2-methylphenyl)methanone (Compound 143)

The reaction was carried out as described in the preparation of compound 142 using N-methyl-tetrahydrofurfurylamine (0.14 g, 1.23 mmol) as the amine. Work up was conducted as described in the preparation of compound 137, and the crude product was purified by flash chromatography eluting with EtOAc/MeOH/Et$_3$N 20:1:0.1. This afforded the title compound as a yellow oil.

$^{13}$C NMR (CDCl$_3$): δ 196.4, 155.8, 149.5, 140.0, 139.9, 137.5, 135.3, 134.7, 134.0, 131.2, 131.1, 130.4, 129.3, 127.1, 125.3, 123.6, 121.4, 116.4, 112.3, 76.8, 67.9, 63.2, 60.9, 42.9, 31.5, 30.2, 25.3, 20.3

EXAMPLE 44

(2-Chloro-4-{[2-(2-{[(2,2-dimethyl-1,3-dioxolan-4-yl)methyl]amino}ethyl)phenyl]amino}phenyl)(2-methylphenyl)methanone (Compound 144)

The reaction was carried out as described in the preparation of compound 142 using 2,2-dimethyl-1,3-dioxolane-4-methanamine (0.16 mL, 1.23 mmol) as the amine. Work up was conducted as described in the preparation of compound 137, and the crude product was purified by flash chromatography eluting with EtOAc/EtOH/Et$_3$N 15:1:0.1. This afforded the title compound as a yellow oil.

$^{13}$C NMR (CDCl$_3$): δ 196.4, 149.2, 139.7, 137.6, 135.3, 134.4, 133.9, 131.2, 131.1, 130.5, 129.4, 127.5, 127.3, 125.3, 124.1, 122.1, 116.1, 112.1, 109.5, 75.0, 67.3, 53.1, 51.8, 33.6, 26.9, 25.2, 20.3

EXAMPLE 45

{2-Chloro-4-[(2-{2-[4-(2-methoxyethyl)piperazin-1-yl]ethyl}phenyl)amino]phenyl}(2-methylphenyl)methanone (Compound 145)

The reaction was carried out as described in the preparation of compound 142 using 1-(2-methoxyethyl)-piperazine (0.18 mL, 1.23 mmol) as the amine. Work up was conducted as described in the preparation of compound 137, and the crude product was purified by flash chromatography eluting with EtOAc/EtOH/Et$_3$N 15:1:0.1. This afforded the title compound as a yellow oil.

$^{13}$C NMR (CDCl$_3$): δ 196.3, 149.1, 139.8, 139.6, 137.6, 135.3, 134.7, 133.8, 131.2, 130.6, 129.4, 127.9, 127.2, 125.3, 123.7, 121.3, 116.8, 112.8, 70.0, 60.9, 58.9, 57.9, 54.0, 53.6, 30.9, 20.3

EXAMPLE 46

(2-Chloro-4-{[2-(2-morpholin-4-ylethyl)phenyl]amino}phenyl)(2-methylphenyl)methanone (Compound 146)

The reaction was carried out as described in the preparation of compound 142. Starting materials were compound 102 (2.0 g, 5.45 mmol) in pyridine (2.7 mL), p-toluenesulfonyl chloride (1.15 g, 6.0 mmol) and morpholine (1.43 mL, 16.4 mmol) as the amine. Work up was conducted as described in the preparation of compound 137, and the crude product was purified by flash chromatography eluting with EtOAc/petroleum ether 1:2–1:0. This afforded the title compound as a yellow crystalline compound.

$^{13}$C NMR (CDCl$_3$): δ 196.3, 149.1, 139.5, 139.5, 137.7, 135.3, 134.7, 133.8, 131.2, 131.1, 130.6, 129.5, 128.1, 127.4, 125.3, 124.1, 122.0, 116.3, 112.7, 67.1, 61.3, 54.4, 30.4, 20.4

EXAMPLE 47

{2-Chloro-4-[(2-{2-[(2,3-dihydroxypropyl)amino]ethyl}phenyl)amino]phenyl}(2-methylphenyl)methanone (Compound 147)

Compound 144 was dissolved in 1M HCl/THF 1:1 (1.2 mL) and the mixture was stirred for 18 h at RT. The reaction mixture was poured into 10% aqueous NaHCO$_3$ (10 mL) and the aqueous phase was extracted with EtOAc (3×10 mL). The combined organic phases were dried (MgSO$_4$), filtered and evaporated in vacuo. This afforded the title compound as a yellow oil.

$^{13}$C NMR (CDCl$_3$): δ 196.7, 149.6, 139.4, 139.0, 137.7, 135.2, 134.2, 133.8, 131.2, 131.0, 130.7, 129.5, 127.8, 127.6, 125.3, 125.1, 123.8, 115.8, 112.1, 70.1, 65.3, 52.1, 50.7, 32.3, 20.4

EXAMPLE 48

(4-{[2-(Aminomethyl)phenyl]amino}-2-chlorophenyl)(2-methylphenyl)methanone (Compound 148)

Compound 154 (2.17 g, 4.51 mmol) was dissolved in DCM (50 mL) and EtOH (10 mL). Hydrazine hydrate (0.44 mL, 9.0 mmol) was added and the reaction mixture was stirred at room temperature for 4 days. The suspension was filtered and the filtrate was concentrated in vacuo. The crude product was purified by flash chromatography using EtOAc/MeOH/Et$_3$N 10:1:0.1 as the eluent. This afforded the title compound as a yellow oil.

$^{13}$C NMR (CDCl$_3$): δ 196.4, 147.8, 141.1, 139.5, 137.7, 135.1, 133.7, 131.2, 130.7, 130.0, 129.5, 128.4, 128.4, 125.3, 122.4, 119.2, 116.8, 113.1, 45.4, 20.4

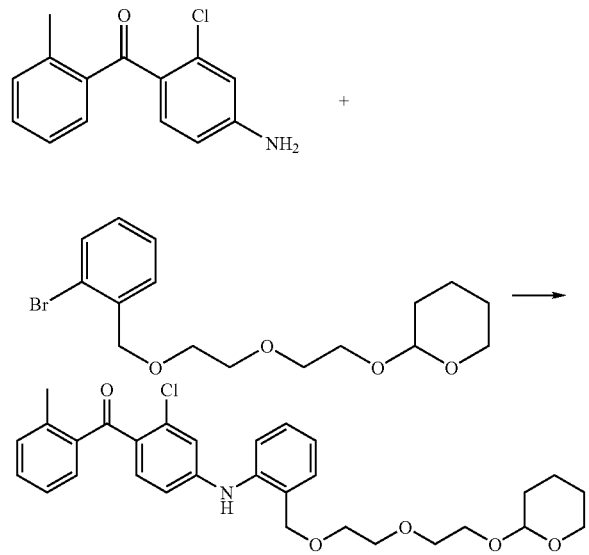

EXAMPLE 49

(2-Chloro-4-{[2-({2-[2-(tetrahydro-2H-pyran-2-yloxy)ethoxy]ethoxy}methyl)phenyl]amino}phenyl)(2-methylphenyl)methanone (Compound 149)

Compound 420 (3.39 g, 10.3 mmol) was dissolved in 15 mL dry 1,4-dioxane in a schlenk tube under an argon atmosphere. (4-Amino-2-chlorophenyl)(2-methylphenyl) methanone (disclosed in WO 01/42189) was added and dissolved in the solvent. R$_a$c-BINAP (0.26 g, 0.42 mmol), Pd$_2$(dba)$_3$ (0.19 g, 0.20 mmol) and Cs$_2$CO$_3$ (4.7 g, 14.4 mmol) were added, and the reaction mixture was stirred under an argon atmosphere at 100° C. for 18 h. The reaction mixture was diluted with H$_2$O and EtOAc, and the water phase was extracted twice with EtOAc. The combined organic phases were washed with brine, dried (MgSO$_4$) and evaporated in vacuo. The crude product was purified by flash chromatography using DCM/acetone 100:1 as the eluent to afford the title compound as an oil.

$^{13}$C NMR (CDCl$_3$): δ 196.4, 147.9, 140.9, 139.4, 137.8, 135.0, 133.6, 131.2, 130.7, 130.4, 129.6, 129.3, 128.7, 128.5, 125.3, 122.8, 120.1, 116.9, 113.3, 99.1, 72.3, 70.6, 70.3, 69.4, 66.6, 62.3, 30.6, 25.4, 20.4, 19.5

EXAMPLE 50

{2-Chloro-4-[(2-{[(tetrahydro-2H-pyran- 2-yloxy)ethoxy]methyl}phenyl)amino]phenyl}(2-methylphenyl)methanone (Compound 150)

The reaction and work up was conducted as described in the preparation of compound 149. Starting materials were compound 422 (8.3 g, 26.3 mmol) in 38 mL dry 1,4-dioxan, (4-amino-2-chlorophenyl)(2-methylphenyl)methanone (6.47 g, 26.3 mmol) (disclosed in WO 01/42189), rac-BINAP (0.67 g, 1.07 mmol), Pd$_2$(dba)$_3$ (0.48 g, 0.52 mmol) and Cs$_2$CO$_3$ (11.98 g, 36.8 mmol). The crude product was purified by flash chromatography using EtOAc/Petroleum ether 1:2 a the eluent to afford the title compound as an oil.

$^{13}$C NMR (CDCl$_3$): δ 196.4, 147.7, 140.9, 139.3, 137.8, 135.0, 133.5, 131.2, 130.7, 130.5, 129.6, 129.2, 128.9, 128.3, 125.3, 122.7, 119.8, 117.1, 113.2, 99.4, 72.3, 69.4, 66.6, 62.7, 30.7, 25.3, 20.4, 19.8

EXAMPLE 51

[2-Chloro-4-({2-[(2-{2-[2-(tetrahydro-2H-pyran-2-yloxy)ethoxy]ethoxy}ethoxy)methyl]phenyl}amino)phenyl](2-methylphenyl)methanone (Compound 151)

The reaction and work up was conducted as described in the preparation of compound 149. Starting materials were compound 421 (3.12 g, 7.74 mmol) in 15 ml dry 1,4-dioxane, (4-amino-2-chlorophenyl)(2-methylphenyl)methanone (2.06 g, 8.37 mmol) (disclosed in WO 01/42189), rac-BINAP (0.21 g, 0.34 mmol), Pd$_2$(dba)$_3$ (0.15 g, 0.17 mmol) and Cs$_2$CO$_3$ (3.8 g, 11.7 mmol). The crude product was purified by flash chromatography using EtOAc/Petroleum ether 1:2–1:1–1:0 as the eluent to afford the title compound as an oil.

$^{13}$C NMR (CDCl$_3$): δ 196.4, 147.9, 140.8, 139.4, 137.8, 135.0, 133.6, 131.2, 130.7, 130.5, 129.6, 129.3, 128.7, 128.5, 125.3, 122.8, 120.1, 117.0, 113.2, 99.0, 72.2, 70.6, 70.6, 70.4, 69.4, 66.6, 62.2, 30.6, 25.4, 20.4, 19.5

EXAMPLE 52

[2-Chloro-4-({2-[(3,3,3-trifluoropropoxy)methyl]phenyl}amino)phenyl](2-methylphenyl)methanone (Compound 152)

The reaction and work up was conducted as described in the preparation of compound 149. Starting materials were compound 419 (0.22 g, 0.79 mmol) and (4-amino-2-chlorophenyl)(2-methylphenyl)methanone (0.19 g, 0.79 mmol) (disclosed in WO 01/42189 A1) in 4 mL dry 1,4-dioxane, rac-BINAP (20.0 mg, 0.03 mmol), Pd$_2$(dba)$_3$ (14 mg, 0.016 mmol) and Cs$_2$CO$_3$ (0.36 g, 1.1 mmol). The crude product was purified by flash chromatography using EtOAc/Petroleum ether 1:2 as the eluent to afford the title compound as an oil.

$^{13}$C NMR (CDCl$_3$): δ 196.4, 147.3, 140.6, 139.2, 137.9, 135.0, 133.5, 131.3, 130.8, 130.6, 129.7, 129.6, 129.4, 127.6, 126.3, 125.4, 122.9, 120.0, 117.0, 113.6, 72.3, 63.0, 34.4, 20.5

EXAMPLE 53

Diethyl 2-({3-chloro-4-[(2-methylphenyl)carbonyl]phenyl}amino)benzylphosphonate (Compound 153)

The reaction was conducted as described in the preparation of compound 149. Starting materials were compound 418 (0.55 g, 1.79 mmol) and (4-amino-2-chlorophenyl)(2-methylphenyl)methanone (0.44 g, 1.79 mmol) (disclosed in WO 01/42189 A1) in 15 mL dry 1,4-dioxane, rac-BINAP (44 mg, 0.07 mmol), Pd$_2$(dba)$_3$ (33 mg, 0.04 mmol) and Cs$_2$CO$_3$ (0.82 g, 2.51 mmol). After 16 h at 100° C. more rac-BINAP (44 mg, 0.07 mmol) and Pd$_2$(dba)$_3$ (33 mg, 0.04 mmol) was added, and stirring was continued at 100° C. for another 7 h. The work up was conducted as described in the preparation of compound 149. The crude product was purified by flash chromatography using EtOAc/Petroleum ether 1:1 as the eluent to afford the title compound as a brown oil.

$^{13}$C NMR (CDCl$_3$): δ 195.7, 148.0, 139.4, 138.8, 137.0, 134.5, 133.0, 131.4, 130.5, 129.9, 128.8, 127.6, 127.4, 124.6, 124.0, 123.7, 122.3, 115.6, 112.1, 62.1, 30.4, 19.7, 15.7

EXAMPLE 54

2-[2-({3-Chloro-4-[(2-methylphenyl)carbonyl] phenyl}amino)benzyl]-1H-isoindole-1,3(2H)-dione (Compound 154)

The reaction was conducted as described in the preparation of compound 149. Starting materials were compound 423 (4.0 g, 12.65 mmol) and (4-amino-2-chlorophenyl)(2-methylphenyl)methanone (3.1 g, 12.7 mmol) (disclosed in WO 01/42189 A1) in 125 mL dry toluene, rac-BINAP (0.47 g, 0.76 mmol), Pd$_2$(dba)$_3$ (0.35 g, 0.38 mmol) and Cs$_2$CO$_3$ (5.77 g, 17.7 mmol). After stirring at 100° C. for 18 h more rac-BINAP (0.24 g, 0.38 mmol) and Pd$_2$(dba)$_3$ (0.17 g, 0.19 mmol) was added, and the reaction mixture was stirred at 100° C. for another 8 h. More rac-BINAP (0.24 g, 0.38 mmol) and Pd$_2$(dba)$_3$ (0.17 g, 0.19 mmol) was added and the reaction stirred for 18 h at 100° C. Work up was carried out as described in the preparation of compound 149. The crude product was purified by flash chromatography using EtOAc/Petroleum ether 1:3 as the eluent to afford the title compound as a yellow crystalline compound.

$^{13}$C NMR (CDCl$_3$): δ 196.4, 168.9, 148.4, 139.4, 137.8, 135.2, 134.4, 133.6, 132.7, 131.9, 131.2, 130.7, 129.6, 129.5, 128.7, 128.2, 125.3, 124.2, 123.6, 122.2, 116.5, 112.9, 37.9, 20.4

EXAMPLE 55

{2-Chloro-4-[(2-{[2-(2-hydroxyethoxy)ethoxy] methyl}phenyl)amino]phenyl}(2-methylphenyl) methanone (Compound 155)

Compound 149 (5.68 g, 10.8 mmol) was dissolved in MeOH (100 mL) and p-toluenesulfonic acid (3.09 g, 16.3 mmol) was added. The solution was stirred at room temperature for 2 h. Aqueous NaHCO$_3$ (5%, 100 mL) was added and the water phase was extracted with EtOAc (3×50 mL). The combined organic phases were washed with brine (50 mL), dried (MgSO$_4$) and evaporated in vacuo. The crude product was purified by flash chromatography using EtOAc/Petroleum ether 1:1–3:2 as the eluent to afford the title compound as an orange oil.

$^{13}$C NMR (CDCl$_3$): δ 196.4, 147.7, 140.7, 139.3, 137.9, 135.0, 133.5, 131.2, 130.8, 130.5, 129.7, 129.4, 129.0, 128.3, 125.4, 122.9, 120.1, 117.0, 113.3, 72.5, 72.2, 70.3, 69.2, 61.8, 20.4

EXAMPLE 56

[2-Chloro-4-({2-[(hydroxyethoxy)methyl] phenyl}amino)phenyl](2-methylphenyl)methanone (Compound 156)

The reaction and work up was conducted as described in the preparation of compound 155. Starting compounds were compound 150 (13 g, 27 mmol) in 290 mL MeOH and p-toluenesulfonic acid (7.6 g, 40.4 mmol). The crude product was purified by flash chromatography using EtOAc/Petroleum ether 1:2–1:1 as the eluent to afford the title compound as a yellow oil.

$^{13}$C NMR (CDCl$_3$): δ 196.6, 147.7, 140.7, 139.3, 137.8, 135.0, 133.5, 131.2, 130.8, 130.5, 129.6, 129.4, 128.9, 128.3, 125.4, 122.9, 120.0, 117.0, 113.4, 72.1, 71.3, 61.7, 20.4

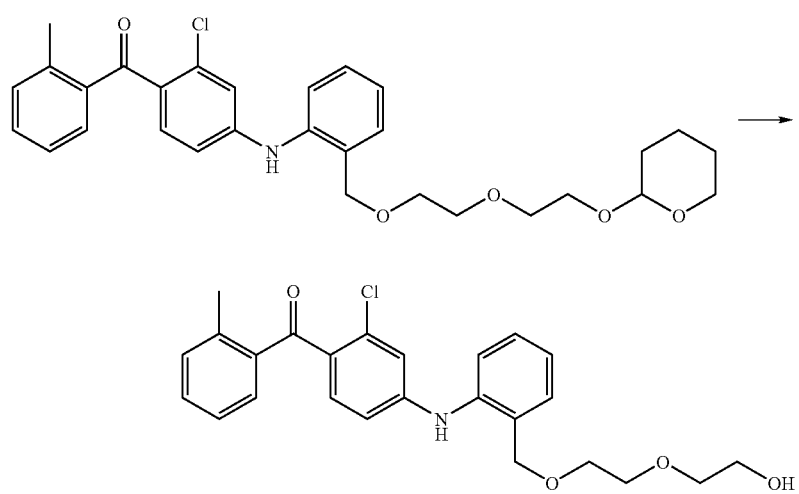

EXAMPLE 57

(2-Chloro-4-{[2-({2-[2-(2-hydroxyethoxy)ethoxy]ethoxy}methyl)phenyl]amino}phenyl)(2-methylphenyl)methanone (Compound 157)

The reaction and work up was conducted as described in the preparation of compound 155. Starting compounds were compound 151 (4.4 g, 7.75 mmol) in 100 mL MeOH and p-toluenesulfonic acid (2.2 g, 11.6 mmol). The crude product was purified by flash chromatography using EtOAc/Petroleum ether 3:1 as the eluent to afford the title compound as an orange oil.

$^{13}$C NMR (CDCl$_3$): δ 196.4, 148.1, 140.7, 139.4, 137.8, 135.0, 133.6, 131.2, 130.7, 130.7, 129.6, 129.4, 128.8, 128.6, 125.3, 123.1, 120.7, 116.9, 113.0, 72.5, 72.1, 70.5, 70.3, 70.3, 69.3, 61.7, 20.4

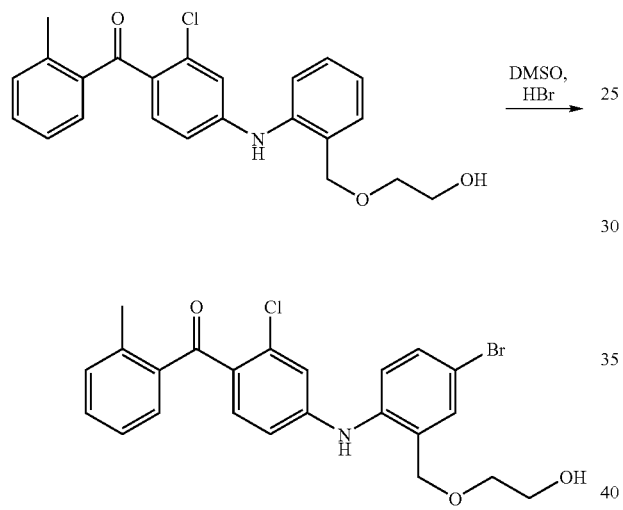

EXAMPLE 58

[4-({4-Bromo-2-[(2-hydroxyethoxy)methyl]phenyl}amino)-2-chlorophenyl](2-methylphenyl)methanone (Compound 158)

Compound 156 (3.8 g, 9.6 mmol) was dissolved in DMSO (115 mL). The solution was cooled on an ice bath and 48% aqueous HBr (32 mL, 285 mmol) was added slowly. The solution was stirred in a closed vessel at room temperature for 5 days. The reaction mixture was cooled on an ice bath and 27% aqueous NaOH (30 mL) was added to give a basic solution. The water phase was extracted three times with EtOAc, the combined organic phases were washed with brine, dried (MgSO$_4$), filtered and evaporated in vacuo. The crude product was purified by flash chromatography using EtOAc/petroleum ether 1:1 as the eluent to afford the title compound as a slightly coloured crystalline compound.

$^{13}$C NMR (CDCl$_3$): δ 196.5, 147.0, 140.0, 139.0, 138.0, 134.9, 133.3, 133.1, 132.1, 131.3, 130.9, 130.1, 129.8, 129.6, 125.4, 121.1, 117.4, 114.8, 113.8, 71.5, 71.4, 61.7, 20.5

EXAMPLE 59

(4-{[4-Bromo-2-({2-[2-(2-hydroxyethoxy)ethoxy]ethoxy}methyl)phenyl]amino}-2-chlorophenyl)(2-methylphenyl)methanone (Compound 159)

The reaction and work up was conducted as described in the preparation of compound 158. Starting materials were compound 157 (2.14 g, 2.56 mmol) in 36 mL DMSO and 48% aqueous HBr (8.6 mL, 76.8 mmol). The reaction time was 8 days. The crude product was purified by flash chromatography eluting with EtOAc/petroleum ether 3:1 to afford the title compound as a yellow oil.

$^1$H NMR (CDCl$_3$): δ 7.48 (1H, bs), 7.24–7.45 (7H, m), 7.20 (1H, t), 7.04 (1H, d), 6.90 (1H, dd), 4.51 (2H, s), 3.55–3.75 (12H, m), 2.45 (3H, s)

EXAMPLE 60

{4-[(4-Bromo-2-{[2-(2-hydroxyethoxy)ethoxy]methyl}phenyl)amino]-2-chlorophenyl}(2-methylphenyl)methanone (Compound 160)

The reaction and work up was conducted as described in the preparation of compound 158. Starting materials were compound 155 (1.19 g, 2.70 mmol) in 36 mL DMSO and 48% aqueous HBr (9.1 mL, 81.1 mmol). The reaction time was 8 days. The crude product was purified by flash chromatography eluting with EtOAc/petroleum ether 3:1 to afford the title compound as an orange oil.

$^{13}$C NMR (CDCl$_3$): δ 196.4, 147.0, 140.0, 139.0, 138.0, 134.9, 133.4, 133.2, 132.2, 131.3, 130.9, 130.1, 129.8, 129.7, 125.4, 121.2, 117.4, 114.8, 113.6, 72.5, 71.6, 70.2, 69.3, 61.8, 20.5

EXAMPLE 61

Diethyl 5-bromo-2-({3-chloro-4-[(2-methylphenyl)carbonyl]phenyl}amino)benzylphosphonate (Compound 161)

The reaction was carried out as described in the preparation of compound 158 using compound 153 (0.11 g, 0.23 mmol) in DMSO (3 mL) and 48% aqueous HBr (0.77 mL, 6.9 mmol). The reaction time was 11 days. The reaction was quenched with aqueous NaHCO$_3$ (10%, 10 mL). The water phase was extracted with EtOAc and the combined organic phases were washed with H$_2$O and brine, dried (MgSO$_4$), filtered and concentrated in vacuo. The crude product was purified by flash chromatography eluting with EtOAc/petroleum ether 1:1 to afford the title compound as a slightly coloured oil $^{13}$C NMR (CDCl$_3$): δ 196.4, 148.0, 139.4, 139.3, 137.8, 135.1, 134.6, 133.5, 131.2, 130.8, 129.6, 128.8, 126.7, 125.3, 124.0, 124.0, 116.6, 116.4, 113.1, 63.0, 30.9, 20.4, 16.4

EXAMPLE 62

[4-({4-Bromo-2-[(3,3,3-trifluoropropoxy)methyl]phenyl}amino)-2-chlorophenyl](2-methylphenyl)methanone (Compound 162)

The reaction and work up was conducted as described in the preparation of compound 158 using compound 152 (0.10 g, 0.22 mmol) in DMSO (2.65 mL) and 48% aqueous HBr (0.75 mL, 6.70 mmol). Reaction time was 6 days. The crude product was purified by flash chromatography using EtOAc/petroleum ether 1:4 as the eluent. This afforded the title compound as a yellow oil.

$^1$H NMR (CDCl$_3$): δ 7.5–7.25 (7H, m), 7.20 (1H, t), 7.00 (1H, d), 6.92 (1H, bs), 6.84 (1H, dd), 4.51 (2H, s), 3.71 (2H, t), 2.55–2.35 (2H, m), 2.46 (3H, s)

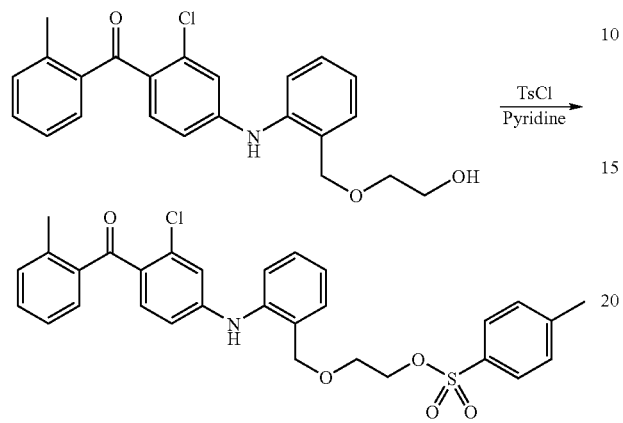

EXAMPLE 63

2-{[2-({3-Chloro-4-[(2-methylphenyl)carbonyl]phenyl}amino)benzyl]oxy}ethyl 4-methylbenzenesulfonate (Compound 163)

Compound 156 (1.0 g, 2.55 mmol) was dissolved in pyridine (1.3 mL) under an argon atmosphere. The solution was cooled on an ice bath and p-toluenesulfonyl chloride (0.56 g, 2.9 mmol) was added. The suspension was stirred for 3 h at room temperature. The reaction was quenched with water and the water phase was extracted twice with EtOAc. The combined organic phases were washed with brine, dried (Na$_2$SO$_4$), filtered and evaporated in vacuo. The crude product was purified by flash chromatography eluting with EtOAc/petroleum ether 1:2. This afforded the title compound as a yellow oil.

$^{13}$C NMR (CDCl$_3$): δ 196.5, 147.4, 145.1, 140.7, 139.2, 137.9, 134.9, 133.5, 132.9, 131.3, 130.8, 130.6, 129.9, 129.7, 129.6, 129.2, 127.9, 127.6, 125.4, 122.8, 120.0, 117.0, 113.8, 72.2, 68.9, 67.5, 21.6, 20.5

EXAMPLE 64

2-{[5-Bromo-2-({3-chloro-4-[(2-methylphenyl)carbonyl]phenyl}amino)benzyl]oxy}ethyl 4-methylbenzenesulfonate (Compound 164)

The reaction and work up was conducted as described in the preparation of compound 163 using compound 158 (1.99 g, 4.19 mmol) in pyridine (4 mL) and p-toluenesulfonyl chloride (0.92 g, 4.19 mmol). The crude product was purified by flash chromatography eluting with EtOAc/petroleum ether 1:2. This afforded the title compound as a yellow oil.

$^{13}$C NMR (CDCl$_3$): δ 196.5, 146.7, 145.2, 140.0, 139.0, 138.1, 134.8, 133.3, 133.2, 132.8, 132.3, 131.3, 131.0, 130.0, 129.8, 129.5, 127.9, 125.4, 121.3, 117.4, 114.8, 114.2, 71.5, 68.8, 67.6, 21.7, 20.5

EXAMPLE 65

2-(2-{[5-Bromo-2-({3-chloro-4-[(2-methylphenyl)carbonyl]phenyl}amino)benzyl]oxy}ethoxy)ethyl 4-methylbenzenesulfonate (Compound 165)

The reaction and work up was conducted as described in the preparation of compound 163 using compound 160 (1.10 g, 2.12 mmol) in pyridine (2 mL) and p-toluenesulfonyl chloride (0.47 g, 2.44 mmol). The crude product was purified by flash chromatography eluting with EtOAc/petroleum ether 1:2. This afforded the title compound as a yellow oil.

$^{13}$C NMR (CDCl$_3$): δ 196.4, 146.9, 144.9, 140.0, 139.0, 138.0, 134.8, 133.4, 133.1, 132.9, 132.1, 131.3, 130.9, 130.1, 129.9, 129.8, 129.6, 127.9, 125.4, 121.0, 117.3, 114.7, 113.7, 71.5, 70.5, 69.2, 69.0, 68.8, 21.6, 20.5

EXAMPLE 66

2-[2-(2-{[5-Bromo-2-({3-chloro-4-[(2-methylphenyl)carbonyl]phenyl}amino)benzyl]oxy}ethoxy)ethoxy]ethyl 4-methylbenzenesulfonate (Compound 166)

The reaction and work up was conducted as described in the preparation of compound 163 using compound 159 (1.15 g, 2.04 mmol) in pyridine (2 mL) and p-toluenesulfonyl chloride (0.45 g, 2.35 mmol). The crude product was purified by flash chromatography eluting with EtOAc/petroleum ether 2:3. This afforded the title compound as a yellow oil.

$^{13}$C NMR (CDCl$_3$): δ 196.4, 149.5, 147.1, 144.8, 140.0, 139.1, 138.0, 134.8, 133.4, 133.1, 132.0, 131.3, 130.9, 130.3, 129.8, 129.7, 129.5, 127.9, 125.4, 121.2, 117.4, 114.8, 113.4, 71.5, 70.8, 70.4, 70.4, 69.4, 69.2, 68.7, 21.6, 20.5

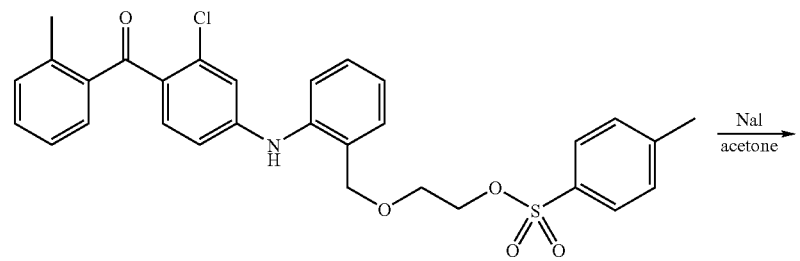

-continued

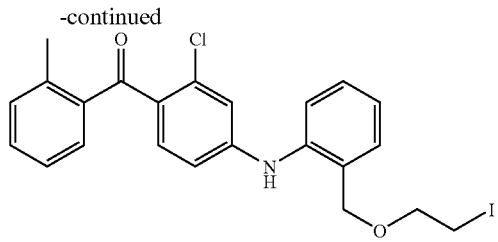

EXAMPLE 67

[4-({4-Bromo-2-[(2-iodoethoxy)methyl]phenyl}amino)-2-chlorophenyl](2-methylphenyl)methanone (Compound 167)

Compound 164 (1.72 g, 2.73 mmol) was dissolved in dry acetone (2.7 mL) and dry NaI (0.82 g, 5.47 mmol) was added. The suspension was stirred in a light protected flask at room temperature for 20 h after which the reaction mixture was diluted with water and the water phase was extracted three times with EtOAc. The combined organic phases were washed with brine, dried (MgSO$_4$), filtered and evaporated in vacuo. This afforded the title compound as a yellow oil.

$^{13}$C NMR (CDCl$_3$): δ 196.8, 147.1, 140.4, 139.3, 138.5, 135.2, 133.7, 132.8, 131.7, 131.4, 130.4, 130.2, 130.0, 125.8, 121.6, 118.0, 115.2, 114.6, 71.6, 70.8, 20.9, 4.1

EXAMPLE 68

{4-[(4-Bromo-2-{[2-(2-iodoethoxy)ethoxy]methyl}phenyl)amino]-2-chlorophenyl}(2-methylphenyl)methanone (Compound 168)

The reaction and work up was conducted as described in the preparation of compound 167 using compound 165 (0.87 g, 1.29 mmol) in 1.3 mL acetone and NaI (0.39 g, 2.59 mmol). Work up afforded the title compound as a yellow oil.

$^{13}$C NMR (CDCl$_3$): δ 196.4, 146.9, 140.1, 139.0, 138.0, 134.9, 133.4, 133.1, 132.1, 131.3, 130.9, 130.0, 129.8, 129.7, 125.4, 121.0, 117.5, 114.7, 113.7, 72.0, 71.7, 69.9, 69.3, 20.5, 2.4

EXAMPLE 69

(4-{[4-Bromo-2-({2-[2-(2-iodoethoxy)ethoxy]ethoxy}methyl)phenyl]amino}-2-chlorophenyl)(2-methylphenyl)methanone (Compound 169)

The reaction and work up was conducted as described in the preparation of compound 167 using compound 166 (1.07 g, 1.49 mmol) in 1.5 mL acetone and NaI (0.45 g, 2.98 mmol). Work up afforded the title compound as a yellow oil.

13C NMR (CDCl$_3$): δ 196.4, 147.1, 140.1, 139.1, 138.0, 134.9, 133.4, 133.1, 132.0, 131.3, 130.9, 130.2, 129.7, 129.5, 125.4, 121.1, 117.4, 114.7, 113.5, 71.9, 71.6, 70.5, 70.4, 70.2, 69.4, 20.5, 2.7

EXAMPLE 70

[2-Chloro-4-({2-[(2-iodoethoxy)methyl]phenyl}amino)phenyl](2-methylphenyl)methanone (Compound 170)

The reaction and work up was conducted as described in the preparation of compound 167 using compound 163 (0.26 g, 0.48 mmol) in 1.5 mL acetone and NaI (0.14 g, 0.96 mmol). The crude product was purified by flash chromatography eluting with EtOAc/petroleum ether 1:2 to afford the title compound as a pale yellow oil.

$^{13}$C NMR (CDCl$_3$): δ 196.4, 147.4, 140.7, 139.2, 137.9, 135.0, 133.4, 131.3, 130.8, 130.7, 129.7, 129.6, 129.3, 127.8, 125.4, 122.9, 120.0, 117.2, 113.8, 71.9, 70.3, 20.5, 3.9

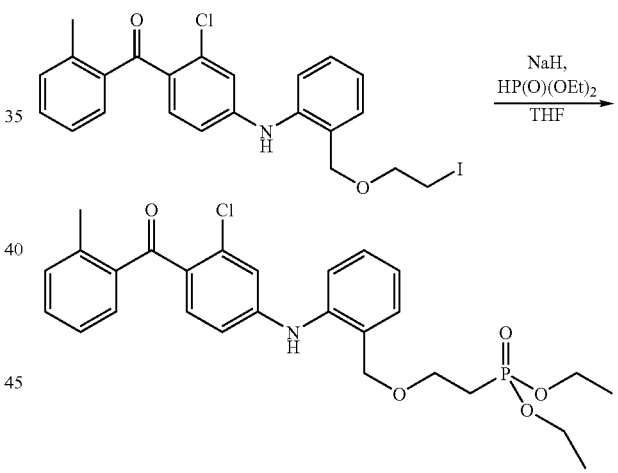

EXAMPLE 71

Diethyl 2-{[2-({3-chloro-4-[(2-methylphenyl)carbonyl]phenyl}amino)benzyl]oxy}ethylphosphonate (Compound 171)

In a dry schlenk tube under an argon atmosphere NaH (0.01 g, 60% in oil, 0.24 mmol) was suspended in dry THF (0.2 mL) and diethylphosphite (0.031 mL, 0.24 mmol) was added. After 10 min compound 170 (0.10 g, 0.20 mmol) dissolved in dry THF (0.3 mL) was added, and the reaction mixture was heated at reflux temperature for 15 h. The reaction mixture was diluted with H$_2$O and the water phase was extracted twice with EtOAc. The combined organic phases were washed with brine, dried (MgSO$_4$), filtered and concentrated in vacuo. The crude product was purified by flash chromatography using EtOAc/petroleum ether 1:2 as the eluent to afford the title compound as a slightly coloured oil.

$^{13}$C NMR (CDCl$_3$): δ 196.3, 148.7, 140.7, 139.4, 137.4, 134.8, 133.4, 130.9, 130.7, 130.3, 129.3, 129.2, 129.1, 127.9, 125.1, 123.1, 121.6, 116.5, 112.8, 71.6, 63.9, 61.6, 26.5, 20.1, 16.1

EXAMPLE 72

Diethyl 2-{[5-bromo-2-({3-chloro-4-[(2-methylphenyl)carbonyl]phenyl}amino)benzyl]oxy}ethylphosphonate (Compound 172)

The reaction was conducted as described in the preparation of compound 171 using NaH (0.036 g, 60% in oil, 0.9 mmol) in dry THF (0.5 mL) and diethylphosphite (0.13 mL, 1.0 mmol). Addition of compound 167 (0.48 g, 0.82 mmol) dissolved in dry THF (0.8 mL) and reflux for 18 h. Work up was carried out as described in the preparation of compound 171. The crude product was purified by flash chromatography using EtOAc/petroleum ether 1:2–4:1 as the eluent to afford the title compound as a yellow oil.

$^{13}$C NMR (CDCl$_3$): δ 196.5, 148.4, 140.2, 139.4, 137.8, 134.9, 133.6, 133.5, 132.2, 131.3, 131.2, 130.7, 129.6, 128.7, 125.3, 123.2, 117.1, 115.3, 113.3, 71.1, 64.3, 61.8, 26.6, 20.4, 16.4

EXAMPLE 73

Diethyl 2-({[5-bromo-2-({3-chloro-4-[(2-methylphenyl)carbonyl]phenyl}amino)benzyl]oxy}ethoxy)ethylphosphon ate (Compound 173)

The reaction was conducted as described in the preparation of compound 171 using NaH (0.023 g, 60% in oil, 0.6 mmol) in dry THF (0.3 mL) and diethylphosphite (0.078 mL, 0.6 mmol). Addition of compound 168 (0.34 g, 0.55 mmol) dissolved in dry THF (1.0 mL) and reflux for 18 h. Work up was carried out as described in the preparation of compound 171. The crude product was purified by flash chromatography using EtOAc/petroleum ether 1:2–1:0 as the eluent to afford the title compound as a yellow oil.

$^{13}$C NMR (CDCl$_3$): δ 196.3, 147.2, 139.8, 139.1, 137.9, 134.9, 133.4, 132.9, 131.9, 131.3, 130.9, 130.4, 129.7, 129.5, 125.4, 121.2, 117.4, 114.9, 113.4, 71.4, 70.0, 69.3, 65.3, 61.7, 27.0, 20.5, 16.4

EXAMPLE 74

Diethyl 2-[2-(2-{[5-bromo-2-({3-chloro-4-[(2-methylphenyl)carbonyl]phenyl}amino)benzyl]oxy}ethoxy)ethoxy]ethylphosphonate (Compound 174)

The reaction was conducted as described in the preparation of compound 171 using NaH (0.03 g, 60% in oil, 0.76 mmol) in dry THF (0.3 mL) and diethylphosphite (0.098 mL, 0.76 mmol). Addition of compound 169 (0.47 g, 0.69 mmol) dissolved in dry THF (1.0 mL) and reflux for 18 h. Work up was carried out as described in the preparation of compound 171. The crude product was purified by flash chromatography using EtOAc/petroleum ether 1:1—EtOAc/MeOH 20:1 as the eluent to afford the title compound as a yellow oil.

$^{13}$C NMR (CDCl$_3$): δ 196.3, 147.3, 139.9, 139.1, 137.9, 134.9, 133.4, 133.0, 132.0, 131.3, 130.9, 130.6, 129.7, 129.3, 125.4, 121.5, 117.3, 114.9, 113.4, 71.4, 70.4, 70.3, 70.1, 69.4, 65.1, 61.6, 27.0, 20.4, 16.4

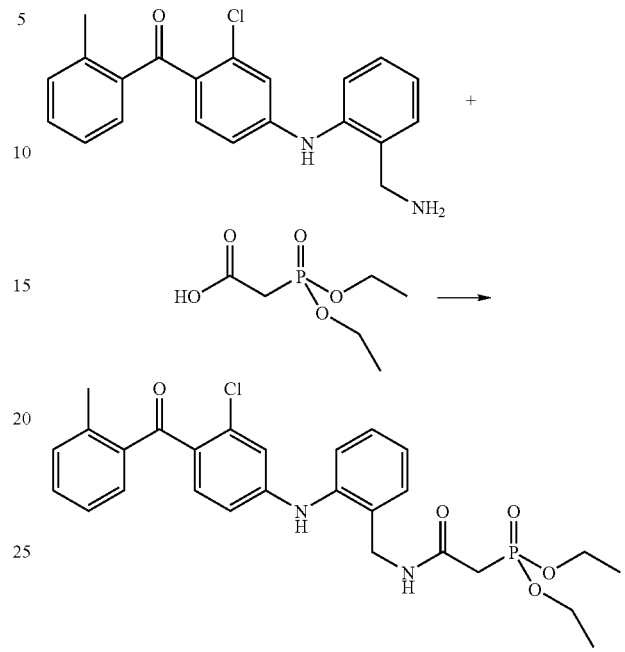

EXAMPLE 75

Diethyl 2-{[2-({3-chloro-4-[(2-methylphenyl)carbonyl]phenyl}amino)benzyl]amino}-2-oxoethylphosphonate (Compound 175)

Compound 148 (0.20 g, 0.56 mmol) was dissolved in dry DCM (1 mL) in oven dried glass ware under an argon atmosphere. Diethylphosphonoacetic acid (0.09 mL, 0.56 mmol) was added followed by dropwise addition of dicyclohexylcarbodiimide (0.13 g, 0.61 mmol dissolved in 1 mL dry DCM). The suspension was stirred at room temperature for 7 h after which it was filtered. The filtrate was diluted with 5 mL DCM and washed with 10% aqueous NaHCO$_3$, H$_2$O and brine. The organic phase was dried (MgSO$_4$), filtered and concentrated in vacuo. The crude product was purified by flash chromatography using EtOAc as the eluent to afford the title compound as a slightly coloured oil.

$^{13}$C NMR (DMSO-D6): δ 195.1, 164.5, 149.8, 139.3, 137.8, 136.4, 133.6, 132.8, 131.0, 130.6, 129.0, 128.7, 128.0, 126.3, 125.5, 124.6, 123.5, 114.9, 111.7, 61.6, 54.8, 34.5, 19.7, 16.1

EXAMPLE 76

Diethyl 2-{[5-bromo-2-({3-chloro-4-[(2-methylphenyl)carbonyl]phenyl}amino)phenyl]amino}-2-oxoethylphosphonate (Compound 176)

The reactions were conducted under an argon atmosphere using oven dried glass ware. Diethylphosphonoacetic acid (0.085 mL, 0.53 mmol) was dissolved in dry toluene (1 mL) and thionylchloride (0.044 mL, 0.61 mmol) was added. The reaction mixture was refluxed for 1 h and then concentrated in vacuo. {4-[(2-Amino-4-bromophenyl)amino]-2-chlorophenyl}(2-methylphenyl)methanone (0.28 g, 0.48 mmol)

(disclosed in WO 01/05744) was dissolved in dry DCM (1 mL) and N,N-diisopropylethyl amine (0.16 mL, 0.96 mmol) was added followed by drop wise addition of the above acid chloride dissolved in dry DCM (2.5 mL). The reaction mixture was stirred at room temperature for 22 h after which it was diluted with DCM. The organic phase was washed with 10% aqueous NaHCO$_3$, H$_2$O and brine, dried (MgSO$_4$), filtered and concentrated in vacuo. The crude product was purified by flash chromatography using EtOAc/petroleum ether 3:1 as the eluent to afford the title compound as an oil.

$^{13}$C NMR (CDCl$_3$): δ 196.5, 163.2, 148.0, 139.0, 138.0, 134.9, 133.3, 131.9, 131.8, 131.3, 130.9, 129.7, 129.4, 129.2, 126.9, 125.4, 124.5, 117.2, 116.6, 113.0, 63.4, 36.1, 20.5, 16.3

EXAMPLE 77

{[5-Bromo-2-({3-Chloro-4-[(2-methylphenyl)carbonyl]phenyl}amino)benzyl]oxy}ethyl (diethoxyphosphoryl)acetate (Compound 177)

The reactions were performed under an argon atmosphere using oven dried glass ware. Diethylphosphonoacetic acid (0.053 mL, 0.33 mmol) was dissolved in dry toluene (2 mL) and thionylchloride (0.065 mL, 0.9 mmol) was added. The reaction mixture was refluxed for 2 h and then concentrated in vacuo. Compound 158 (0.14 g, 0.3 mmol) was dissolved in dry THF (1.5 mL). 4-N,N-dimethylaminopyridine (0.073 g, 0.6 mmol) was added followed by addition of the above acid chloride dissolved in THF(1.5 mL). The reaction mixture was heated at reflux temperature for 20 h. The reaction mixture was diluted with EtOAc and aqueous NaHCO$_3$, and the organic phase was washed with H$_2$O and brine, and the combined water phases were extracted with EtOAc. The combined organic phases were dried (MgSO$_4$), filtered and concentrated in vacuo. The crude product was purified by flash chromatography using EtOAc/petroleum ether 2:1 as the eluent to afford the title compound as a slightly coloured oil.

$^{13}$C NMR (CDCl$_3$): δ 196.4, 165.7, 147.5, 139.4, 139.1, 138.0, 134.9, 133.4, 133.0, 132.0, 131.3, 130.9, 129.7, 129.5, 125.4, 122.1, 117.3, 115.5, 113.4, 70.9, 68.1, 64.8, 62.9, 34.4, 20.5, 16.3

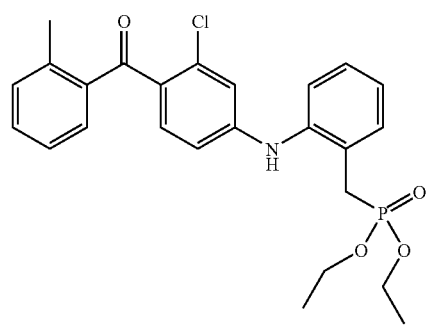

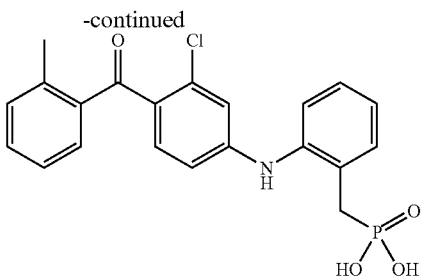

EXAMPLE 78

2-({3-Chloro-4-[(2-methylphenyl)carbonyl]phenyl}amino)benzylphosphonic acid (Compound 178)

Compound 153 (0.27 g, 0.56 mmol) was dissolved in dry DCM (5 mL) under an argon atmosphere. Trimethylsilyl bromide (0.37 mL, 2.8 mmol) was added and the solution was stirred at room temperature for 20 h. The solution was concentrated in vacuo and then co-concentrated with MeOH three times. The crude product was dissolved in MeOH and treated with activated charcoal, filtered and concentrated in vacuo to afford the title compound as an orange oil.

$^{13}$C NMR (DMSO-D6): δ 195.0, 149.2, 139.3, 138.9, 136.3, 133.8, 133.7, 132.0, 130.9, 130.6, 128.7, 127.8, 127.2, 126.2, 125.5, 124.3, 122.6, 114.7, 111.9, 32.3, 19.7

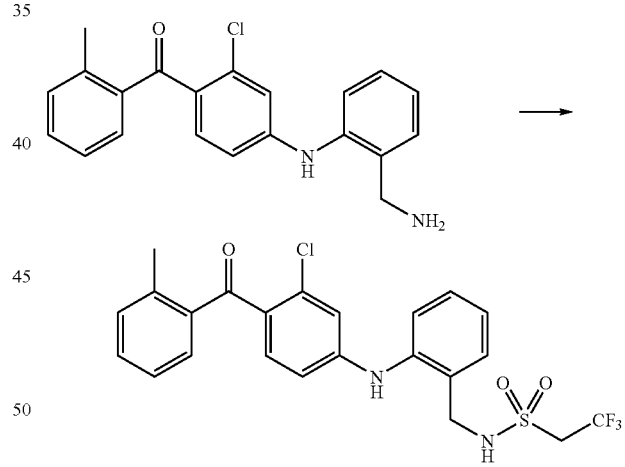

EXAMPLE 79

N-[2-({3-Chloro-4-[(2-methylphenyl)carbonyl]phenyl}amino)benzyl]-2,2,2-trifluoroethanesulfonamide (Compound 179)

Compound 148 (0.18 g, 0.71 mmol) was dissolved in dry pyridine (0.9 mL) and 2,2,2-trifluoroethanesulfonyl chloride (0.12 mL, 1.1 mmol) was added. The solution was stirred at room temperature for 1 h after which it was concentrated in vacuo. The oil was diluted with H$_2$O and the water phase was extracted three times with EtOAc. The combined organic phases were washed with 10% aqueous NaHCO$_3$, dried (MgSO$_4$), filtered and concentrated in vacuo. The crude product was purified by flash chromatography using EtOAc/petroleum ether 1:2 as the eluent to afford the title compound as a yellow oil.

$^{13}$C NMR (CDCl$_3$): δ 196.8, 148.1, 139.3, 139.0, 137.9, 135.0, 133.5, 131.3, 131.0, 130.1, 129.8, 129.3, 128.5, 125.4, 124.8, 123.2, 121.5, 116.5, 113.2, 54.6, 44.5, 20.4

EXAMPLE 80

N-[5-Bromo-2-({3-chloro-4-[(2-methylphenyl)carbonyl]phenyl}amino)phenyl]-2,2,2-trifluoroethanesulfonamide (Compound 180)

The reaction was conducted as described in the preparation of compound 179 using {4-[(2-amino-4-bromophenyl)amino]-2-chlorophenyl}(2-methylphenyl)methanone (0.15 g, 0.35 mmol)(disclosed in WO 01/05744) in pyridine (0.47 mL) and trifluoroethanesulfonyl chloride (0.059 mL, 0.53 mmol). The reaction time was 4 h. Work up as described in the preparation of compound 179 afforded the title compound as brown crystals.

$^{13}$C NMR (CDCl$_3$): δ 196.8, 149.2, 147.3, 138.5, 138.3, 134.9, 134.0, 133.2, 131.5, 131.3, 131.0, 130.2, 130.0, 127.1, 125.7, 125.5, 121.3, 118.0, 117.1, 113.7, 53.1, 20.6.

EXAMPLE 81

{2-Chloro-4-[(2-{[(tetrahydro-2H-pyran-2-yloxy)propoxy]methyl}phenyl)amino]phenyl}(2-methylphenyl)methanone (Compound 181)

The reaction and work up was conducted as described in the preparation of compound 149. Starting materials were compound 425 (2.6 g, 7.9 mmol) in 15 mL dry 1,4-dioxane, (4-amino-2-chlorophenyl)(2-methylphenyl)methanone (2.14 g, 8.7 mmol) (disclosed in WO 01/42189 A1), rac-BINAP (0.22 g, 0.35 mmol), Pd$_2$(dba)$_3$ (0.16 g, 0.17 mmol) and Cs$_2$CO$_3$ (3.9 g, 12.0 mmol). The crude product was purified by flash chromatography using EtOAc/petroleum ether 1:3 as the eluent to afford the title compound as a yellow oil.

$^{13}$C NMR (CDCl$_3$): δ 196.4, 147.5, 140.6, 139.3, 137.9, 135.0, 133.5, 131.3, 130.8, 130.5, 129.7, 129.2, 129.1, 128.5, 125.4, 122.8, 119.7, 117.0, 113.4, 99.1, 72.0, 67.4, 64.3, 62.6, 30.7, 30.0, 25.4, 20.4, 19.8

EXAMPLE 82

[2-Chloro-4-({2-[(hydroxypropoxy)methyl]phenyl}amino)phenyl](2-methylphenyl)methanone (Compound 182)

The reaction and work up was conducted as described in the preparation of compound 155. Starting compounds were compound 181 (3.89 g, 7.9 mmol) in 100 mL MeOH and p-toluenesulfonic acid (2.25 g, 11.82 mmol). The crude product was purified by flash chromatography using EtOAc/Petroleum ether 1:1 as the eluent to afford the title compound as a yellow oil.

$^{13}$C NMR (CDCl$_3$): δ 196.5, 147.6, 140.5, 139.2, 137.9, 135.0, 133.5, 131.3, 130.8, 130.6, 129.7, 129.3, 129.1, 128.4, 125.4, 123.0, 120.1, 116.9, 113.4, 72.0, 68.5, 61.1, 32.2, 20.4

EXAMPLE 83

Diethyl 3-{[2-({3-chloro-4-[(2-methylphenyl)carbonyl]phenyl}amino)benzyl]oxy}propylphosphonate (Compound 183)

The reaction and work up was conducted as described in the preparation of compound 149. Starting materials were compound 428 (0.14 g, 0.4 mmol) in 3 mL dry 1,4-dioxane, (4-amino-2-chlorophenyl)(2-methylphenyl)methanone (0.098 g, 0.4 mmol) (disclosed in WO 01/42189 A1), rac-BINAP (0.01 g, 0.016 mmol), Pd$_2$(dba)$_3$ (0.008 g, 0.009 mmol) and Cs$_2$CO$_3$ (0.18 g, 0.56 mmol). The crude product was purified by flash chromatography using EtOAc/petroleum ether 1:2->4:1 as the eluent to afford the title compound as a pale yellow oil.

$^{13}$C NMR (CDCl$_3$): δ 196.4, 147.6, 140.5, 139.3, 137.9, 135.0, 133.5, 131.3, 130.8, 130.7, 129.7, 129.3, 129.1, 128.4, 125.4, 122.9, 120.0, 117.1, 113.5, 71.8, 69.6, 61.6, 23.4, 23.0, 20.4, 16.5

EXAMPLE 84

Diethyl 2-[2-({3-chloro-4-[(2-methylphenyl)carbonyl]phenyl}amino)phenyl]ethylphosphonate (Compound 184)

The reaction and work up was conducted as described in the preparation of compound 149. Starting materials were compound 431 (0.73 g, 2.3 mmol) in 19 mL dry 1,4-dioxane, (4-amino-2-chlorophenyl)(2-methylphenyl)methanone (0.55 g, 2.3 mmol) (disclosed in WO 01/42189 A1), rac-BINAP (0.06 g, 0.08 mmol), Pd$_2$(dba)$_3$ (0.046 g, 0.05 mmol) and Cs$_2$CO$_3$ (1.04 g, 3.18 mmol). The crude product was purified by flash chromatography using EtOAc as the eluent to afford the title compound as a yellow oil.

$^{13}$C NMR (CDCl$_3$): δ 196.4, 149.7, 139.7, 138.5, 137.6, 135.3, 134.9, 134.7, 133.8, 131.1, 130.6, 130.5, 129.4, 127.6, 125.3, 125.2, 124.4, 115.6, 112.2, 61.7, 26.6, 23.9, 20.3, 16.3

EXAMPLE 85

Diethyl 2-[5-bromo-2-({3-chloro-4-[(2-methylphenyl)carbonyl]phenyl}amino)phenyl]ethylphosphonate (Compound 185)

The reaction and work up was conducted as described in the preparation of compound 158. Starting materials were compound 184 (0.37 g, 0.8 mmol) in 11 mL DMSO and 48% aqueous HBr (2.6 mL, 23 mmol). The reaction time was 5 days. The crude product was purified by flash chromatography eluting with EtOAc/petroleum ether 1:2->1:0 to afford the title compound as a colourless crystalline compound.

$^{13}$C NMR (CDCl$_3$): δ 196.4, 149.0, 139.4, 138.0, 137.8, 136.7, 136.6, 135.2, 133.7, 133.4, 131.2, 130.7, 129.5, 128.3, 125.5, 125.3, 117.4, 115.9, 112.5, 61.9, 26.4, 23.7, 20.4, 16.3

EXAMPLE 86

2-{[2-({3-Chloro-4-[(2-methylphenyl)carbonyl]phenyl}amino)benzyl]amino}-2-oxoethylphosphonic acid (Compound 186)

Compound 175 (0.04 g, 0.075 mmol) was dissolved in dry CH$_2$Cl$_2$ (0.5 mL) under an argon atmosphere. Trimethylsilyl bromide (0.1 mL, 0.75 mmol) was added and the solution was kept at room temperature for 45 h. The solution was concentrated in vacuo and then co-concentrated with MeOH three times. This afforded the title compound as an orange oil.

$^{13}$C NMR (DMSO d-6): δ 195.6, 166.3, 150.3, 139.7, 138.2, 136.7, 134.1, 133.9, 133.6, 131.4, 131.0, 129.6, 129.1, 128.3, 126.5, 126.0, 125.1, 124.0, 115.2, 112.1, 37.5, 20.1

EXAMPLE 87

(2-{[3-Chloro-4-(2-methylbenzoyl)phenyl] amino}phenyl)-carbamic acid phenethyl ester (Compound 187)

The reactions were conducted under an argon atmosphere. A solution of 2-phenylethanol (0.108 mL) in DCM (2.5 mL, 0.90 mmol) was cooled to 0° C. A mixture of bis(trichloromethyl)carbonate (0.097 g, 0.33 mmol) and pyridine (0.07 mL, 0.90 mmol) in DCM (2.5 mL) was added slowly under stirring. The reaction mixture was stirred for 2 h at room temperature and then filtered, and concentrated in vacuo. The residue was dissolved in DCM (2.5 mL) and {2-chloro-4-[(2-aminophenyl)amino]phenyl}(2-methylphenyl)methanone (0.150 g, 0.45 mmol)(disclosed in WO 98/32730) and potassium carbonate (0.25 g, 1.78 mmol) were added. The reaction mixture was stirred at room temperature for 48 h after which it was poured into a mixture of water and Et$_2$O. The aqueous phase was extracted with more Et$_2$O. The combined organic phases were washed with water, brine, dried (MgSO$_4$), filtered and concentrated in vacuo. The crude product was purified by flash chromatography using EtOAc/petroleum ether 1:3 as the eluent to afford the title compound.

$^{13}$C NMR (CDCl$_3$): δ 196.6, 154.0, 149.1, 139.1, 137.9, 137.5, 135.0, 133.5, 133.1, 131.3, 130.9, 130.6, 129.7, 129.0, 128.9, 128.6, 126.8, 126.7, 125.8, 125.4, 125.0, 121.9, 116.1, 112.4, 66.1, 35.3, 20.4

EXAMPLE 88

N-(2-{[3-Chloro-4-(2-methylbenzoyl)phenyl] amino}phenyl)-2-phenoxy-acetamide (Compound 188)

A solution of 2-phenoxyacetic acid (75 mg, 0.49 mmol), thionylchloride (72 μL, 1.0 mmol) and one drop of DMF in toluene (2.0 mL) was refluxed for 30 min. The reaction mixture was concentrated in vacuo and the resulting crude acid chloride was dissolved in dry DCM (2.0 ml). The solution was added slowly to a cooled (0° C.) solution of {2-chloro-4-[(2-aminophenyl)amino]phenyl}(2-methylphenyl)methanone (0.150 g, 0.45 mmol) (disclosed in WO 98/32730) and triethylamine (135 mg, 1.33 mmol) in dry DCM (5.0 ml). The solution was allowed to reach room temperature. The reaction mixture was stirred for 3 h and then poured into a mixture of NaHCO$_3$ (aq.) and EtOAc. The aqueous phase was extracted with more EtOAc (×2). The combined organic phases were washed with brine, dried (MgSO$_4$), filtered and concentrated in vacuo. The crude product was purified by flash chromatography using DCM as the eluent to afford the title compound as a yellow oil.

$^{13}$C NMR (CDCl$_3$): δ 196.5, 166.9, 156.7, 148.8, 139.0, 137.8, 135.1, 133.6, 131.8, 131.4, 131.2, 130.8, 129.9, 129.6, 128.9, 126.6, 126.3, 125.7, 125.3, 122.9, 122.4, 116.0, 114.5, 112.1, 67.3, 20.4

EXAMPLE 89

N-(2-{[3-Chloro-4-(2-methylbenzoyl)phenyl] amino}phenyl)-3-phenoxy-propionamide (Compound 189)

The reaction and work up was conducted as described in the preparation of compound 188 using 3-phenoxypropionic acid (81 mg, 0.49 mmol) as the carboxylic acid. Purification was done by flash chromatography eluting with petroleum ether/EtOAc 1:1 to afford the title compound as a yellow oil.

$^{13}$C NMR (CDCl$_3$): δ 196.7, 170.0, 157.9, 148.8, 139.2, 137.7, 134.9, 133.5, 132.4, 132.0, 131.2, 130.8, 129.6, 129.5, 128.5, 126.1, 125.9, 125.4, 124.9, 123.8, 121.5, 116.2, 114.5, 112.4, 63.9, 37.2, 20.4

EXAMPLE 90

N-(2-{[3-Chloro-4-(2-methylbenzoyl)phenyl] amino}phenyl)-2-(1,3-dioxo-1,3-dihydro-isoindole-2-yl)-acetamide (Compound 190)

The reaction and work up was conducted as described in the preparation of compound 188 using (1,3-dioxo-1,3-dihydro-isoindol-2-yl)acetyl chloride (219 mg, 0.98 mmol) as the acid chloride. Purification was done by flash chromatography eluting with DCM/EtOAc 10:1 to afford the title compound as a yellow oil.

$^{13}$C NMR (CDCl$_3$): δ 196.5, 167.8, 165.2, 148.9, 139.1, 137.9, 134.9, 134.6, 133.5, 132.1, 131.7, 131.3, 130.9, 129.7, 128.9, 126.4, 126.2, 125.4, 123.8, 123.0, 116.1, 112.3, 41.6, 20.5

EXAMPLE 91

N-(2-{[3-Chloro-4-(2-methylbenzoyl)phenyl] amino}phenyl)-succinamic acid 2-(2-methoxy-ethoxy)ethyl ester (Compound 191)

A solution of diethylazodicarboxylate (40% in toluene, 229 μL, 0.5 mmol) was slowly added to a mixture of N-(2-{[3-chloro-4-(2-methylbenzoyl)phenyl] amino}phenyl)-succinamic acid (200 mg, 0.46 mmol) (disclosed in WO 01/05746), triphenylphosphine (132 mg, 0.50 mmol), and 2-(2-methoxyethoxy)ethanol (55 mg, 0.46 mmol) in dry toluene (2.5 ml). The reaction mixture was stirred for 48 h and then poured into a mixture of water and EtOAc. The aqueous phase was extracted with more EtOAc (×2). The combined organic phases were washed with brine, dried (MgSO$_4$), filtered and concentrated in vacuo. The crude product was purified by flash chromatography using EtOAc as the eluent to afford the title compound as a yellow oil.

$^{13}$C NMR (CDCl$_3$): δ 196.6, 173.0, 171.1, 148.7, 139.3, 137.7, 135.0, 133.6, 133.4, 131.2, 130.9, 130.8, 129.5, 128.4, 126.4, 125.4, 125.1, 124.7, 123.7, 116.4, 112.5, 71.8, 70.4, 68.9, 63.9, 59.0, 31.7, 29.7, 20.4

EXAMPLE 92

N-(2-{[3-Chloro-4-(2-methylbenzoyl)phenyl] amino}phenyl)-benzenesulfonamide (Compound 192)

To a cold (ice/water) solution of {2-chloro-4-[(2-aminophenyl)amino]phenyl}(2-methylphenyl)methanone (0.67 g, 2.0 mmol)(disclosed in WO 98/32730) in pyridine (10 mL) was added benzenesulfonyl chloride (0.32 mL, 2.5 mmol). The reaction mixture was warmed to room temperature. After stirring for 48 h, the reaction mixture was poured into ice water. The precipitate was filtered off, washed with water, and diethyl ether to afford the crude product. Crystallization from acetic acid afforded the title compound as a solid.

M.p: 211–215° C.

$^{13}$C NMR (DMSO-$d_6$): δ 195.2, 148.6, 139.4, 139.2, 136.4, 134.0, 133.2, 133.2, 132.3, 131.0, 130.6, 129.7, 128.7, 126.7, 126.6, 126.4, 126.2, 125.6, 124.6, 123.8, 114.6, 112.1, 19.7

EXAMPLE 93

Acetic acid (2-{[3-chloro-4-(2-methylbenzoyl)phenyl]amino}phenylcarbamoyl)-methyl ester (Compound 193)

The reaction and work up was conducted as described in the preparation of compound 188 using acetoxyacetyl chloride (62 μL, 0.58 mmol) as the acid chloride. Purification was done by flash chromatography eluting with petroleum ether/EtOAc 1:1 to afford the title compound as a yellow oil.

$^{13}$C NMR (CDCl$_3$): δ 196.5, 169.3, 165.8, 148.6, 138.9, 138.0, 135.0, 133.5, 131.7, 131.6, 131.4, 131.0, 129.7, 129.3, 126.6, 125.6, 125.4, 123.2, 116.0, 112.4, 63.2, 20.5

EXAMPLE 94

1-(2-{[3-Chloro-4-(2-methylbenzoyl)phenyl]amino}phenyl)pyrrolidine-2,5-dione (Compound 194)

Iso-butylchloroformate (60 μL, 0.46 mmol) was added to a stirred solution of N-(2-{[3-chloro-4-(2-methylbenzoyl)phenyl]amino}phenyl)-succinamic acid (200 mg, 0.46 mmol) (disclosed in WO 01/05746) and 4-methylmorpholine (51 μL, 0.46 mmol) in THF (5.0 mL) at −15° C. After 5 min at 0° C. the reaction mixture was cooled to −15° C. and a solution of ethyl diisopropyl amine (65 μL, 0.46 mmol) in THF (5.0 mL) was added. The resulting reaction mixture was kept at 0° C. for 1 h. The reaction mixture was stirred for 16 h at RT and then poured into a mixture of 1 M HCl(aq) and EtOAc. The organic phase was washed with more HCl(aq)(×2). The organic phase was washed with brine, dried (MgSO$_4$), filtered and concentrated in vacuo. The crude product was purified by flash chromatography using petroleum ether/EtOAc 1:2 as the eluent to afford the title compound as an oil.

$^{13}$C NMR (CDCl$_3$): δ 196.5, 176.2, 147.8, 138.9, 138.0, 137.0, 134.8, 133.3, 131.3, 131.0, 130.3, 129.7, 129.5, 129.1, 126.3, 125.6, 125.4, 125.2, 116.9, 113.1, 28.6, 20.5

EXAMPLE 95

2-(2-{[3-Chloro-4-(2-methylbenzoyl)phenyl]amino}phenyl)ethyl propionate (Compound 195)

The reaction and work up was conducted as described in the preparation of compound 188 using propionyl chloride (63 mg, 0.68 mmol) as the acid chloride. Purification was done by flash chromatography eluting with DCM to afford the title compound as an oil.

$^{13}$C NMR (CDCl$_3$): δ 196.4, 174.8, 148.8, 139.3, 138.9, 137.8, 135.1, 133.7, 131.2, 131.1, 130.9, 130.7, 129.6, 128.6, 128.0, 125.3, 124.8, 123.2, 116.0, 112.7, 64.5, 31.2, 27.6, 20.4, 9.0

EXAMPLE 96

2,2-Dimethyl-propionic acid 2-(2-{[3-chloro-4-(2-methylbenzoyl)phenyl]amino}phenyl)ethyl ester (Compound 196)

The reaction and work up was conducted as described in the preparation of compound 188 using pivaloyl chloride (32 mg, 0.27 mmol) as the acid chloride. Purification was done by flash chromatography eluting with petroleum ether/EtOAc 10:1 to afford the title compound as a yellow oil.

$^{13}$C NMR (CDCl$_3$): δ 196.5, 179.2, 148.9, 139.4, 138.8, 137.8, 135.2, 133.6, 131.2, 131.1, 130.8, 130.7, 129.6, 128.6, 128.0, 125.3, 124.8, 123.3, 116.0, 112.6, 64.1, 38.8, 31.2, 27.2, 20.4

EXAMPLE 97

[2-Chloro-4-({2-[3-(tetrahydro-2H-pyran-2-yloxy)propoxy]phenyl}amino)phenyl](2-methylphenyl)methanone (Compound 197)

The reaction and work up was conducted as described in the preparation of compound 101, using 2-[3-(2-bromophenoxy)propoxy]tetrahydro-2H-pyran (4.10 g) as the bromide. Purification was done by flash chromatography eluting with petroleum ether/EtOAc 4:1 to afford the title compound as a yellow oil.

$^{13}$C NMR (CDCl$_3$): δ 196.4, 149.2, 147.4, 139.2, 137.9, 134.9, 133.4, 131.3, 130.8, 130.1, 129.7, 129.3, 125.4, 123.0, 120.9, 118.6, 117.1, 113.5, 112.4, 99.1, 65.8, 64.0, 62.6, 30.7, 29.6, 25.4, 20.4, 19.7

EXAMPLE 98

(2-Chloro-4-{[2-(3-hydroxypropoxy)phenyl]amino}phenyl)(2-methylphenyl)methanone (Compound 198)

The reaction and work up was conducted as described in the preparation of compound 102. Starting compounds were compound 197 (2.56 g) in MeOH (5.0 mL) and 4-toluenesulfonic acid (1.52 g). Purification was done by flash chromatography eluting with petroleum ether/EtOAc 4:1 to afford the title compound as a yellow oil.

$^{13}$C NMR (CDCl$_3$): δ 196.5, 149.5, 147.4, 139.2, 137.9, 134.9, 133.4, 131.3, 130.8, 130.1, 129.7, 129.3, 125.4, 123.3, 121.2, 119.1, 117.0, 113.5, 112.8, 66.4, 60.1, 32.0, 20.5

EXAMPLE 99 tert-Butyl 2-(2-{[3-chloro-4-(2-methylbenzoyl)phenyl]amino}phenyl)ethyl carbonate (Compound 199)

Compound 102 (200 mg) was dissolved in dry triethylamine (3.0 mL) and {[(tert-butoxycarbonyl)oxy]amino}(phenyl)acetonitrile (148 mg) was added. The solution was stirred at 70° C. for 5 h. The reaction mixture was cooled to room temperature and then poured into a mixture of water and EtOAc. The aqueous phase was extracted with more EtOAc (×2). The combined organic phases were washed with brine, dried (MgSO$_4$), filtered and concentrated in vacuo. The crude product was purified by flash chromatography using petroleum ether/diethyl ether 8:1 as the eluent to afford the title compound.

$^{13}$C NMR (CDCl$_3$): δ 196.5, 153.5, 148.8, 139.4, 139.2, 137.8, 135.2, 133.7, 131.3, 131.2, 130.8, 130.7, 129.6, 128.5, 128.0, 125.3, 124.6, 122.6, 116.4, 112.6, 82.9, 67.5, 31.7, 27.8, 20.4

EXAMPLE 100

2-({[([(5-Bromo-2-{[3-chloro-4-(2-methylbenzoyl)phenyl]amino}phenyl)amino]carbonyl}amino)ethyl 2-methylacrylate (Compound 200)

2-Isocyanatoethyl 2-methylacrylate (0.31 g, 2.2 mmol) was slowly added to a solution of {4-[(2-amino-4-bromophenyl)amino]-2-chlorophenyl}(2-methylphenyl)methanone (0.60 g, 1.44 mmol)(disclosed in WO 01/05744) in dry pyridine (3.00 mL). The solution was stirred at room temperature for 6 h after which it was poured into a mixture of water and EtOAc. The aqueous phase was extracted with more EtOAc (×2). The combined organic phases were washed with brine, dried (MgSO$_4$), filtered and concentrated in vacuo. The crude product was purified by flash chromatography using petroleum ether/EtOAc 4:1 as the eluent to afford the title compound as a light brown solid.

$^{13}$C NMR (CDCl$_3$): δ 197.4, 167.6, 155.7, 149.0, 138.8, 137.8, 135.8, 135.0, 134.8, 133.6, 131.4, 131.2, 130.1, 129.8, 128.5, 127.3, 126.3, 126.1, 125.5, 125.4, 118.7, 116.3, 112.5, 63.7, 39.6, 20.5, 18.3

EXAMPLE 101

(4-{[4-Bromo-2-(2-hydroxyethyl)phenyl]amino}-2-chloro-phenyl)(2-methylphenyl)methanone (Compound 201)

The reaction and work up was conducted as described in the preparation of compound 158 using compound 102 (0.10 g, 0.22 mmol) in DMSO (3.0 mL) and 48% aqueous HBr (0.4 mL, 6.70 mmol). Reaction time was 2 days. The crude product was purified by flash chromatography using EtOAc/petroleum ether 1:4 as the eluent. This afforded the title compound as a yellow oil.

$^{13}$C NMR (CDCl$_3$): δ 196.6, 148.3, 139.3, 139.0, 137.8, 135.5, 135.2, 133.9, 133.7, 131.2, 130.8, 130.4, 129.6, 128.4, 125.3, 123.7, 116.7, 116.2, 112.5, 64.9, 34.4, 20.4

EXAMPLE 102

3-(2-{[3-Chloro-4-(2-methylbenzoyl)phenyl]amino}phenoxy)propyl acetate (Compound 202)

Acetic acid anhydride (72 μL, 0.77 mmol) was added to a solution of compound 198 (121 mg, 0.31 mmol) in 100% acetic acid (1.0 mL) at 20° C. under stirring. The reaction mixture was stirred over night at 80° C. and then poured into a mixture of water and EtOAc. The aqueous phase was extracted with more EtOAc (×2). The combined organic phases were washed with water, dried (MgSO$_4$), filtered and concentrated in vacuo. The crude product was purified by flash chromatography using petroleum ether/EtOAc 4:1 as the eluent to afford the title compound.

$^{13}$C NMR (CDCl$_3$): δ 196.8, 171.5, 149.5, 147.8, 139.6, 138.3, 135.3, 133.8, 131.7, 131.2, 130.5, 130.1, 129.6, 125.8, 123.5, 121.5, 119.3, 117.5, 114.0, 112.8, 65.4, 61.4, 29.0, 21.4, 20.8

EXAMPLE 103

[2-Chloro-4-({2-[3-(morpholin-4-yl)propoxy]phenyl}amino)phenyl](2-methylphenyl)methanone (Compound 203)

Compound 198 (100 mg, 0.25 mmol) was dissolved in dry pyridine (130 μL) under an argon atmosphere. The solution was cooled on an ice bath and 4-toluenesulfonyl chloride (48 mg, 0.25 mmol) was added. The reaction mixture was quenched with water after 45 min at room temperature. The aqueous phase was extracted twice with EtOAc. The combined organic phases were washed with brine, dried (MgSO$_4$), filtered and concentrated in vacuo. The crude product was purified by flash chromatography using petroleum ether/EtOAc 4:1 as the eluent. The tosylate was dissolved in dry DMF (2.0 mL) and morpholine (17 μL, 0.19 mmol) was added. The reaction mixture was stirred for 48 h at room temperature and then poured into a mixture of water and EtOAc. The aqueous phase was extracted with more EtOAc (×2). The combined organic phases were washed with water, dried (MgSO$_4$), filtered and concentrated in vacuo. The crude product was purified by flash chromatography using DCM/MeOH 100:4 as the eluent to afford the title compound as a yellow oil.

$^{13}$C NMR (CDCl$_3$): δ 196.4, 149.4, 147.4, 139.2, 137.9, 134.9, 133.4, 131.3, 130.8, 129.9, 129.7, 129.3, 125.4, 123.2, 120.9, 119.0, 117.1, 113.6, 112.3, 66.9, 66.9, 55.5, 53.8, 26.4, 20.5

EXAMPLE 104

N-(2-{[3-Chloro-4-(2-methylbenzoyl)phenyl]amino}phenyl)-N'-(4-phenoxybutyl)succinamide (Compound 204)

4-(4,6-Dimethoxy-1,3,5-triazin-2-yl)-4-methylmorpholin-4-ium chloride (DMT-MM) (69 mg, 0.25 mmol) was added to a solution of N-(2-{[3-chloro-4-(2-methylbenzoyl)phenyl]amino}phenyl)-succinamic acid (100 mg, 0.23 mmol) (disclosed in WO 01/05746) and 4-phenoxybutylamine (30 mg, 0.25 mmol) in methanol (2.0 mL). The reaction mixture was stirred at room temperature for 18 h. The reaction mixture was poured into 1 N HCl (aq.) and was extracted with EtOAc (×2). The combined organic phases were washed with water, dried (MgSO$_4$), filtered and concentrated in vacuo. The crude product was purified by flash chromatography using DCM/MeOH/NH$_3$(aq.) 95:5:0.5 as the eluent to afford the title compound as a yellow solid.

$^{13}$C NMR (CDCl$_3$): 6196.6, 172.4, 171.8, 158.8, 148.6, 139.2, 137.8, 134.9, 133.5, 133.4, 131.2, 130.8, 130.6, 129.7, 129.5, 128.6, 126.3, 125.4, 124.9, 124.7, 123.2, 120.8, 116.6, 114.5, 112.4, 67.2, 39.5, 32.4, 31.5, 26.7, 26.3, 20.4

EXAMPLE 105

N-(2-{[3-Chloro-4-(2-methylbenzoyl)phenyl]amino}phenyl)-N'-(6-hydroxyhexyl)succinamide (Compound 205)

4-(4,6-Dimethoxy-1,3,5-triazin-2-yl)-4-methylmorpholin-4-ium chloride (DMT-MM) (138 mg, 0.50 mmol) was added to a solution of N-(2-{[3-chloro-4-(2-methylbenzoyl)phenyl]amino}phenyl)-succinamic acid (200 mg, 0.46 mmol) (disclosed in WO 01/05746) and 6-aminohexanol (60 mg, 0.51 mmol) in THF (4.0 mL). The reaction mixture was stirred at room temperature for 18 h. The reaction mixture was poured into 1 N HCl (aq.) and was extracted with EtOAc (×2). The combined organic phases were washed with water, dried (MgSO$_4$), filtered and concentrated in vacuo. The crude product was purified by flash chromatography using DCM/MeOH/NH$_3$(aq.) 95:5:0.5 as the eluent to afford the title compound as a yellow solid.

$^{13}$C NMR (CDCl$_3$): δ 196.7, 172.5, 171.8, 148.6, 139.2, 137.8, 134.9, 133.5, 133.4, 131.3, 130.8, 130.5, 129.7, 128.6, 126.2, 125.4, 124.9, 124.7, 123.0, 116.6, 112.5, 62.4, 39.6, 32.5, 32.3, 31.5, 29.4, 26.2, 25.1, 20.4

EXAMPLE 106

N-(2-{[3-Chloro-4-(2-methylbenzoyl)phenyl]amino}phenyl)-N'-(2,3-dihydroxypropyl)succinamide (Compound 206)

The reaction and work up was conducted as described in the preparation of compound 204. Starting compounds were N-(2-{[3-chloro-4-(2-methylbenzoyl)phenyl]amino}phenyl)-succinamic acid (100 mg, 0.46 mmol) (disclosed in WO 01/05746) and 3-aminopropane-1,2-diol (23 mg, 0.25 mmol). The crude product was purified by flash chromatography using DCM/MeOH/NH$_3$(aq.) 90:10:0.5 as the eluent to afford the title compound as a yellow solid.

$^{13}$C NMR (CDCl$_3$): δ 197.1, 173.8, 172.2, 148.8, 138.9, 137.9, 134.7, 133.4, 133.3, 131.3, 131.1, 130.7, 129.8, 128.4, 126.4, 125.4, 124.9, 123.5, 70.9, 63.9, 42.3, 32.0, 31.0, 20.5

EXAMPLE 107 tert-Butyl (1R)-3-(2-{[3-chloro-4-(2-methylbenz6yl)phenyl]amino}phenyl)- 1-(hydroxymethyl)propylcarbamate (Compound 207)

Trifluoroacetic acid (78 µL, 0.78 mmol) was added to a solution of compound 434 (213 mg, 0.39 mmol) in wet MeOH (2.50 mL). The reaction mixture was refluxed for 10 h and then poured into mixture of saturated NaHCO$_3$ and EtOAc. The organic phase was washed with brine, dried (MgSO$_4$), filtered and concentrated in vacuo. The crude product was purified by flash chromatography using petroleum ether/EtOAc 2:1 as the eluent to afford the title compound as a yellow oil.

$^{13}$C NMR (CDCl$_3$): δ 196.5, 156.7, 149.8, 139.5, 138.2, 137.7, 136.0, 135.2, 133.8, 131.2, 130.6, 130.5, 129.5, 127.9, 127.3, 125.5, 125.3, 124.6, 115.9, 112.1, 80.1, 65.4, 52.2, 32.6, 28.4, 27.5, 20.4

EXAMPLE 108

Diethyl 6-[3-(2-{[3-chloro-4-(2-methylbenzoyl)phenyl]amino}phenylcarbamoyl)propionylamino]-hexyl phosphate (Compound 208)

A quantity of iodine (53 mg, 0.21 mmol) was added at 0° C. to a solution of triethylphosphite (36 µL, 0.21 mmol) in anhydrous DCM (0.50 mL). After stirring for 15 min at 0° C. and for 5 min at room temperature, this solution was added, via a cannula, to a solution of compound 205 (101 mg, 0.19 mmol) in anhydrous pyridine (61 µL, 0.75 mmol). After stirring for 90 min at 0° C. and for further 90 min at room temperature the reaction mixture was poured into water and DCM. The organic phase was washed with water, dried (MgSO$_4$), filtered and concentrated in vacuo. The crude product was purified by flash chromatography using DCM/MeOH 97:3 as the eluent to afford the title compound as a yellow oil.

$^{13}$C NMR (CDCl$_3$): δ 196.6, 172.5, 171.9, 148.7, 139.3, 137.8, 134.9, 133.5, 133.4, 131.2, 130.8, 129.6, 128.5, 126.1, 125.4, 124.9, 124.6, 123.1, 116.6, 112.4, 67.3, 63.8, 39.3, 32.7, 31.6, 29.9, 29.2, 25.9, 24.7, 20.4, 16.1

EXAMPLE 109

Ethyl N-({[(2E)-3-(2-{[3-chloro-4-(2-methylbenzoyl)phenyl]amino}phenyl)prop-2-enyl]amino}carbonyl)glycinate (Compound 209)

Ethyl isocyanatoacetate (45 mg, 0.35 mmol) was added to a solution of compound 111 (100 mg, 0.27 mmol) in dry DCM (1.0 mL). The solution was stirred at room temperature for 5 h after which it was poured into a mixture of water and DCM. The aqueous phase was extracted with more DCM (×2). The combined organic phases were washed with brine, dried (MgSO$_4$), filtered and concentrated in vacuo. The crude product was purified by flash chromatography using petroleum ether/EtOAc 4:1 as the eluent to afford the title compound.

$^{13}$C NMR (CDCl$_3$): δ 196.8, 172.0, 158.6, 149.4, 139.4, 137.6, 137.5, 135.0, 133.6, 131.3, 131.2, 130.8, 129.5, 129.2, 128.4, 127.8, 127.2, 126.1, 125.4, 124.9, 123.4, 116.5, 112.5, 61.5, 42.6, 42.2, 20.4, 14.1

EXAMPLE 110 tert-Butyl 2-(2-{[3-chloro-4-(2-methylbenzoyl)phenyl]amino}phenyl)ethyl(methyl)carbamate (Compound 210)

The reaction and work up was conducted as described in the preparation of compound 101. Starting compounds were (4-amino-2-chlorophenyl)(2-methylphenyl)methanone (211 mg, 0.86 mmol) (disclosed in WO 01/42189 A1) and compound 435 (324 mg, 1.03 mmol). The crude product was purified by flash chromatography using petroleum ether/EtOAc 6:1 as the eluent to afford the title compound as a yellow oil.

$^{13}$C NMR (CDCl$_3$): δ 196.5, 149.3, 139.7, 139.4, 137.7, 135.2, 133.7, 131.1, 130.5, 129.5, 127.5, 125.3, 123.5, 122.0, 116.4, 112.2, 80.4, 50.0, 35.1, 31.1, 28.5, 20.3

Example 111

N-(5-Bromo-2-{[3-chloro-4-(2-methylbenzoyl)phenyl]amino}phenyl)-N'-(6-hydroxyhexyl)succinamide (Compound 211)

The reaction and work up was conducted as described in the preparation of compound 205. Starting compounds were N-(5-bromo-2-{[3-chloro-4-(2-methylbenzoyl)phenyl]amino}phenyl)-succinamic acid (600 mg, 1.16 mmol) (prepared by a similar method as described in WO 01/05746) and 6-aminohexanol (151 mg, 1.28 mmol). The crude product was purified by flash chromatography using EtOAc as the eluent to afford the title compound as a yellow solid.

$^{13}$C NMR (CDCl$_3$): δ 196.7, 172.6, 171.8, 148.2, 139.0, 138.0, 134.9, 133.3, 132.1, 131.4, 131.0, 129.8, 129.2, 128.9, 127.2, 125.4, 124.3, 117.0, 116.8, 112.7, 62.4, 39.7, 32.5, 32.3, 31.4, 29.4, 26.3, 25.1, 20.5

EXAMPLE 112

N-(5-Bromo-2-{[3-chloro-4-(2-methylbenzoyl)phenyl]amino}phenyl)-N'-(2,3-dihydroxyproyl)succinamide (Compound 212)

The reaction and work up was conducted as described in the preparation of compound 211. Starting compounds were N-(5-bromo-2-{[3-chloro-4-(2-methylbenzoyl)phenyl]amino}phenyl)-succinamic acid (600 mg, 1.16 mmol) (prepared as described in WO 01/05746) and 3-amino-1,2-propane-diol (117 mg, 1.28 mmol). The crude product was purified by flash chromatography using EtOAc followed by EtOAC/MeOH 95:5 as the eluent to afford the title compound as a solid.

$^{13}$C NMR (CDCl$_3$): δ 197.2, 173.9, 172.2, 148.4, 138.7, 138.1, 134.6, 133.3, 132.3, 132.0, 131.4, 131.3, 130.0, 129.0, 127.2, 125.5, 124.9, 117.3, 116.8, 112.7, 70.9, 64.0, 42.4, 32.1, 31.6, 20.6

EXAMPLE 113

(2Z)-N-[(2E)-3-(2-{[3-chloro-4-(2-methylbenzoyl)phenyl]amino}phenyl)prop-2-enyl]-2-(2,5-dioxoimidazolidin-4-ylidene)acetamide (Compound 213)

A mixture of (2Z)-(2,5-dioxoimidazolidin-4-ylidene)acetic acid (35 mg, 0.22 mmol) and compound 111 (75 mg, 0.20) in THF (1.5 mL) was stirred at 20° C. for 10 min. DMTMM (40 mg) was added to the mixture and stirred for 20 h at 20° C. The reaction mixture was poured into water and extracted with EtOAc (×3). The organic phase was combined and washed with brine and dried with MgSO$_4$. The crude product was purified by chromatography eluting with petroleum ether/EtOAc 2:3 followed by EtOAc to afford the title compound as a yellow foam.

$^{13}$C NMR (DMSO-d$_6$): δ 195.1, 164.7, 164.4, 154.6, 150.4, 139.3, 137.3, 137.1, 136.3, 133.6, 131.8, 130.9, 130.5, 128.7, 128.5, 127.9, 126.5, 126.2, 125.9, 125.5, 125.4, 125.1, 114.7, 111.5, 97.6, 40.8, 19.7

EXAMPLE 114

(2-Chloro-4-{[2-(difluoromethyl1)phenyl]amino}phenyl)(2-methylphenyl)methanone (Compound 214)

The reaction and work up was conducted as described in the preparation of compound 101. Starting compounds were (4-amino-2-chlorophenyl)(2-methylphenyl)methanone (270 mg, 1.10 mmol) (disclosed in WO 01/42189 A1) and compound 1-bromo-2-(difluoromethoxy)benzene (324 mg, 1.03 mmol). The crude product was purified by flash chromatography using petroleum ether/EtOAc 9:1 as the eluent to afford the title compound as a yellow oil.

$^{13}$C NMR (CDCl$_3$): δ 196.4, 146.2, 141.6, 138.8, 138.2, 134.8, 133.1, 132.9, 131.4, 131.1, 130.7, 130.0, 126.3, 125.4, 123.1, 120.3, 119.7, 117.8, 116.3, 114.4, 20.6

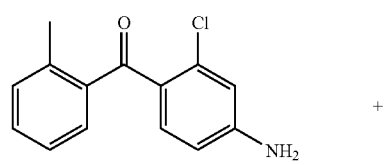

+

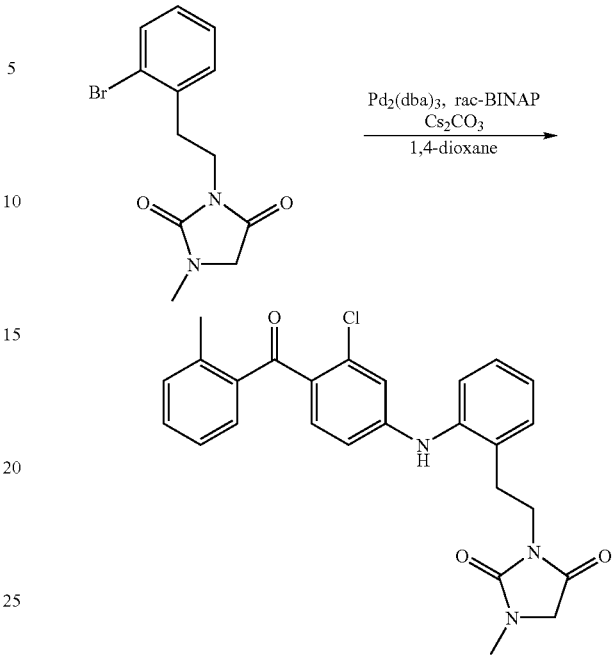

EXAMPLE 115

3-{[2-({3-Chloro-4-[(2-methylphenyl)carbonyl]phenyl}amino)phenyl]ethyl}-1-methylimidazolidine-2,4-dione (Compound 215)

A mixture of (4-amino-2-chlorophenyl)(2-methylphenyl)methanone (61 mg. 0.25 mmol) (disclosed in WO 01/42189 A1), compound 436 (89 mg, 0.30 mmol), BINAP (5 mg), Pd$_2$(dba)$_3$ (5 mg) and Cs$_2$CO$_3$ (114 mg, 0.35 mmol) in 1,4-dioxane (5 ml) was heated to 120° C. under stirring for 3 days. The reaction mixture was filtered. The obtained solution was concentrated in vacuo. The residue was purified by chromatography (petroleum ether/ethyl acetate 1:1) to provide the desired product, which was not pure. The impure product was further purified by preparative TLC (petroleum ether/ethyl acetate 2:1) to give the pure title compound as brownish oil.

$^1$H NMR (CDCl$_3$): δ 7.53 (d, 1H), 7.4–7.0 (m, 9H), 6.95 (bs, 1H), 6.89 (dd,1H), 3.80 (s, 2H), 3.79 (m, 2H), 3.08 (m, 2H), 2.91 (s, 3H), 2.44 (s, 3H)

EXAMPLE 116

3-{[2-({3-Chloro-4-[(2-methylphenyl)carbonyl]phenyl}amino)phenyl]ethyl}-5,5-dimethyloxazoline-2,4-dione (Compound 216)

A mixture of (4-amino-2-chlorophenyl)(2-methylphenyl)methanone (31 mg, 0.13 mmol) (disclosed in WO 01/42189 A1) and compound 437 (47 mg, 0.15 mmol) were treated as described in the preparation of compound 215). Purification was done by flash chromatography (petroleum ether/ethyl acetate 4:1) to provide the title compound as brownish oil.

$^{13}$C NMR (CDCl$_3$): δ 196.5, 176.1, 154.6, 149.0, 139.3, 139.0, 137.9, 135.1, 133.6, 131.4, 131.2, 131.0, 130.7, 129.6, 128.8, 128.6, 125.4, 125.3, 124.7, 116.0, 112.6, 84.0, 39.0, 29.8, 23.4, 20.4

EXAMPLE 117

4-{[2-({3-Chloro-4-[(2-methylphenyl)carbonyl]phenyl}amino)phenyl]ethyl}morpholine-3,5-dione (Compound 217)

A mixture of (4-amino-2-chlorophenyl)(2-methylphenyl)methanone (61 mg. 0.25 mmol) (disclosed in WO 01/42189 A1) and compound 438 (89 mg, 0.30 mmol) were treated as described in the preparation of compound 215. Purification was done by flash chromatography (petroleum ether/ethyl acetate 4:1) to provide the title compound as brownish oil.

$^{13}$C NMR (CDCl$_3$): δ 196.5, 169.5, 148.5, 139.3, 139.0, 137.8, 135.1, 133.6, 131.2, 131.2, 130.7, 129.8, 129.6, 128.8, 128.2, 125.3, 124.1, 122.2, 116.3, 113.0, 77.2, 67.6, 38.6, 30.3, 20.4

EXAMPLE 118

1-{[2-({3-Chloro-4-[(2-methylphenyl)carbonyl]phenyl}amino)phenyl]ethyl}piperidine-2,6-dione (Compound 218)

A mixture of (4-amino-2-chlorophenyl)(2-methylphenyl)methanone (61 mg, 0.25 mmol) (disclosed in WO 01/42189 A1) and compound 439 (89 mg, 0.30 mmol) were treated as described in the preparation of compound 215. Purification was done by flash chromatography (petroleum ether/ethyl acetate 2:1) to provide the title compound as brownish oil.

$^{13}$C NMR (CDCl$_3$): δ 196.5, 172.9, 148.6, 139.4, 139.1, 137.8, 135.0, 133.6, 131.2, 130.7, 130.2, 129.7, 129.6, 128.5, 127.9, 125.3, 123.6, 121.4, 116.4, 113.1, 39.6, 32.7, 30.6, 20.4, 17.1

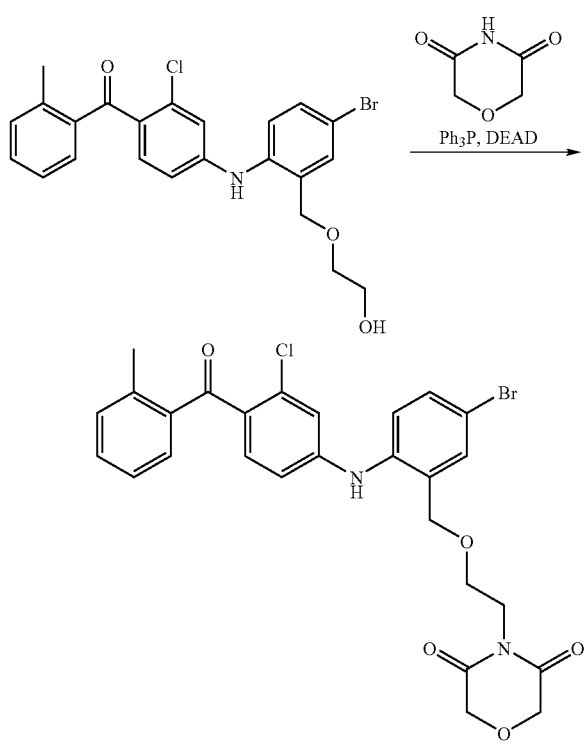

EXAMPLE 119

4-(2-{[5-Bromo-2-({3-chloro-4-[(2-methylphenyl)carbonyl]phenyl}amino)benzyl]oxy}ethyl)morpholine-3,5-dione (Compound 219)

To a solution of Compound 158 (47 mg, 0.1 mmol), morpholine-3,5-dione (16 mg, 0.14 mmol) and triphenylphosphine (37 mg, 0.14 mmol) in THF (5 ml) was added diethyl azodicarboxylate solution (40% in toluene, 0.1 ml, 0.23 mmol) at RT. The reaction solution was stirred at the same temperature for 18 h and concentrated in vacuo. The residue was purified by chromatography (petroleum ether/ethyl acetate 1:1) to furnish the title compound, which was impure. The product was further purified by preparative TLC (petroleum ether/ethyl acetate 1:1) to give the pure title compound as yellow oil.

$^{13}$C NMR (CDCl$_3$): δ 196.5, 169.4, 147.0, 140.0, 139.1, 138.0, 134.9, 133.4, 132.2, 131.3, 130.9, 129.9, 129.8, 125.4, 121.4, 117.4, 114.8, 113.9, 71.1, 67.7, 66.8, 38.1, 20.5

EXAMPLE 120

1-(2-{[5-Bromo-2-({3-chloro-4-[(2-methylphenyl)carbonyl]phenyl}amino)benzyl]oxy}ethyl)pyrrolidine-2,5-dione (Compound 220)

Compound 158 (47 mg, 0.1 mmol), succinimide (14 mg, 0.14 mmol) were treated as described in the preparation of compound 219. Purification was done by flash chromatography (petroleum ether/ethyl acetate 1:1) to provide the title compound as yellow oil.

$^{13}$C NMR (CDCl$_3$): δ 196.5, 177.4, 147.2, 139.9, 139.0, 138.0, 134.9, 133.5, 133.4, 132.2, 131.3, 130.9, 130.0, 129.8, 129.6, 125.4, 121.7, 117.3, 114.9, 113.8, 70.8, 66.6, 38.5, 28.2, 20.5

EXAMPLE 121

Ethyl 2-[3-(2-{5-bromo-[2-({3-chloro-4-[(2-methylphenyl)carbonyl]phenyl}amino)bezoyloxy}ethyl)-2,4,5-trioxoimidazolidin-1-yl]acetate (compound 221)

Compound 158 (47 mg, 0.1 mmol) and ethyl 2,4,5-trioxoimidazolidine-1-acetate (28 mg, 0.14 mmol) were treated as described in the preparation of compound 219. Purification was done by flash chromatography (petroleum ether/ether 1:1) to provide the title compound, which was impure. The product was further purified by chromatography (CH$_2$Cl$_2$/ethyl acetate 15:1) to furnish the title compound as yellow foam.

$^{13}$C NMR (CDCl$_3$): δ 165.8, 153.1, 146.9, 139.9, 139.0, 138.1, 134.8, 133.4, 133.3, 132.4, 131.4, 131.0, 130.0, 129.8, 129.7, 125.4, 121.7, 117.4, 115.0, 114.0, 71.1, 66.1, 62.6, 39.8, 39.3, 20.5, 14.0

EXAMPLE 122

3-(2-{[5-Bromo-2-({3-chloro-4-[(2-methylphenyl)carbonyl]phenyl}amino)benzyl]oxy}ethyl)imidazolidine-2,4-dione (Compound 222)

Compound 158 (47 mg, 0.1 mmol), hydantoin (14 mg, 0.14 mmol) were treate as described in the preparation of compound 219. Purification was done by flash chromatography (petroleum ether/ethyl acetate 1:1) to provide the title compound, which was impure. The product was further purified by preparative TLC (petroleum ether/ethyl acetate 1:1) to furnish the title compound as yellow oil.

$^{13}$C NMR (CDCl$_3$): δ 196.5, 171.3, 157.8, 147.4, 139.9, 139.1, 138.0, 134.9, 133.5, 133.4, 132.2, 131.3, 130.9, 130.2, 129.8, 129.5, 125.4, 121.9, 117.3, 115.0, 113.7, 70.9, 66.9, 46.4, 38.5, 20.5

EXAMPLE 123

1-(2-{[5-Bromo-2-({3-chloro-4-[(2-methylphenyl)carbonyl]phenyl}amino)benzyl]oxy}ethyl)-3,4-cis-diacetoxypyrrolidine-2,5-dione (Compound 223)

Compound 158 (67 mg, 0.1 mmol) and 2,3-cis-diacetoxysuccinimide (30 mg, 0.14 mmol) were treated as described in the preparation of compound 219. Purification was done by flash chromatography (CH$_2$Cl$_2$/ethyl acetate 1:20) to provide the title compound as yellow oil.

$^{13}$C NMR (CDCl$_3$): δ 196.5, 169.9, 169.5, 147.1, 139.9, 139.0, 138.0, 134.8, 133.5, 133.3, 132.3, 131.3, 130.9, 130.0, 129.8, 125.4, 121.7, 117.5, 115.0, 113.9, 72.7, 71.0, 66.1, 39.2, 20.5, 20.3

EXAMPLE 124

3-(2-{[5-Bromo-2-({3-chloro-4-[(2-methylphenyl)carbonyl]phenyl}amino)benzyl]oxy}ethyl)thiazoline-2,4-dione (Compound 224)

Compound 158 (47 mg, 0.1 mmol) and 2,4-thiazolidione (16 mg, 0.14 mmol) were treated as described in the preparation of compound 219. Purification was done by flash chromatography (petroleum ether/ethyl acetate 3:1) to provide the title compound, which was impure. The product was further purified by preparative TLC (petroleum ether/ethyl acetate 3:1) to furnish the title compound as yellow oil.

$^{13}$C NMR (CDCl$_3$): δ 196.5, 172.0, 171.6, 147.0, 139.9, 139.0, 138.0, 134.9, 133.4, 133.4, 132.3, 131.3, 130.9, 129.8, 125.4, 121.6, 117.4, 114.9, 114.0, 71.0, 66.3, 41.5, 33.8, 20.5

EXAMPLE 125

3-(2-{[5-Bromo-2-({3-chloro-4-[(2-methylphenyl)carbonyl]phenyl}amino)benzyl]oxy}ethyl)-1-methylimidazolidine-2,4-dione (Compound 225)

Compound 158 (47 mg, 0.1 mmol) and methylhydantoin (16 mg, 0.14 mmol) were treated as described in the preparation of compound 219. Purification was done by flash chromatography (petroleum ether/ethyl acetate 1:1) to provide the title compound, which was impure. The product was further purified by preparative TLC (petroleum ether/ethyl acetate 1:1) to furnish the pure title compound as yellow oil.

$^{13}$C NMR (CDCl$_3$): δ 196.5, 170.0, 156.7, 147.4, 140.0, 139.1, 137.9, 134.9, 133.6, 133.4, 132.2, 131.3, 130.9, 130.3, 129.7, 129.5, 125.4, 121.9, 117.4, 115.0, 113.7, 70.8, 67.2, 51.7, 38.7, 29.7, 20.5

EXAMPLE 126

1-(2-{[5-Bromo-2-({3-chloro-4-[(2-methylphenyl)carbonyl]phenyl}amino)benzyl]oxy}ethyl)imidazolidine-2,4,5-trione (Compound 226)

Compound 158 (47 mg, 0.1 mmol) and parabanic acid (16 mg, 0.14 mmol) were treated as described in the preparation of compound 219. Purification was done by flash chromatography (CH$_2$Cl$_2$/ethyl acetate 4:1) to provide the title compound, which was impure. The product was further purified by preparative TLC (CH$_2$Cl$_2$/ethyl acetate 20:1) to furnish the title compound as yellow oil.

$^{13}$C NMR (CDCl$_3$): δ 196.4, 156.4, 153.8, 146.8, 139.7, 138.9, 138.1, 134.8, 133.3, 132.4, 131.4, 131.0, 130.0, 129.9, 129.8, 125.4, 121.8, 117.4, 115.1, 113.9, 70.9, 66.1, 39.2, 20.5

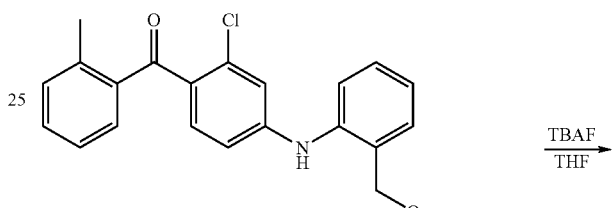

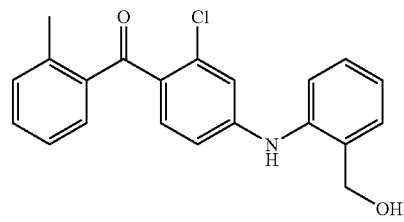

EXAMPLE 127

(2-Chloro-4-{[2-(hydroxymethyl)phenyl]amino}phenyl)(2-methylphenyl)methanone (Compound 227)

Compound 441 (3.21 g, 6.32 mmol) and TBAF.3H$_2$O (2.99 g, 6.32 mmol) were dissolved in THF (20 ml). The obtained reaction solution was stirred at RT for 0.5 h. After reaction the solution was concentrated in vacuo. The residue was redissolved in CH$_2$Cl$_2$ and washed with H$_2$O. The aqueous phase was extracted twice with CH$_2$Cl$_2$. The combined organic phases were dried over MgSO$_4$ and concentrated in vacuo. The crude product was purified by chromatography (petroleum ether/ethyl acetate 2:1) to give the title compound as reddish foam.

$^{13}$C NMR (CDCl$_3$): δ 196.7, 147.5, 140.4, 139.1, 137.9, 135.0, 133.5, 131.3, 130.9, 130.8, 129.7, 129.7, 129.2, 129.0, 125.4, 123.1, 120.1, 117.0, 113.4, 64.3, 20.4

EXAMPLE 128

2-{[3-chloro-4-(2-methylbenzoyl)phenyl]amino}benzyl acetate (Compound 228)

To a solution of compound 227 (50 mg, 0.14 mmol), $Et_3N$ (0.1 ml) and DMAP (3 mg) was added $Ac_2O$ (0.05 ml) at RT. The reaction solution was stirred at the same temperature for 1 h. After reaction the solution was concentrated in vacuo. The residue was redissolved in $CH_2Cl_2$ and washed with aqueous saturated solution of sodium bicarbonate. The aqueous phase was extracted twice with $CH_2Cl_2$. The combined organic phases were dried over $MgSO_4$ and concentrated in vacuo. The residue was filtered through a short column of silica gel (ethyl acetate/petroleum ether 1:2) to give the title compound as yellow oil.

$^{13}C$ NMR ($CDCl_3$): δ 196.4, 171.8, 148.1, 139.7, 139.2, 137.8, 135.1, 133.5, 132.3, 131.2, 130.8, 130.1, 129.6, 128.9, 128.0, 125.3, 124.2, 122.1, 116.5, 113.0, 63.6, 21.0, 20.4

The invention claimed is:

1. A compound of the general formula I

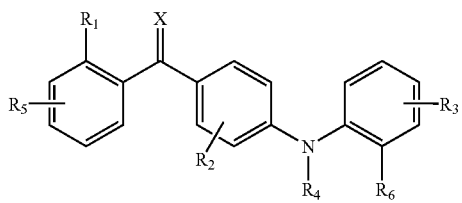

(I)

X represents oxygen;

$R_1$ represents a substituent selected from the group consisting of halogen, trifluoromethyl, ($C_1$–$C_3$)alkyl, ($C_2$–$C_3$)olefinic group, ($C_1$–$C_3$)alkoxy $R_2$ represents one or more, same or different substituents selected from the group consisting of hydrogen, halogen, amino, ($C_1$–$C_3$)alkyl, ($C_2$–$C_3$)olefinic group, ($C_1$–$C_3$)alkoxy;

$R_3$ represents one or more, same or different substituents selected from the group consisting of hydrogen, halogen, hydroxy, trifluoromethyl, cyano, carbamoyl ($C_1$–$C_6$)alkyl, ($C_2$–$C_6$)olefinic group, ($C_1$–$C_6$)alkoxy, and ($C_1$–$C_6$)alkoxycarbonyl;

$R_4$ represents hydrogen;

$R_5$ represents one or more, same or different substituents selected from the group consisting of hydrogen, halogen, trifluoromethyl, ($C_1$–$C_3$)alkyl, ($C_2$–$C_3$)olefinic group, ($C_1$–$C_3$)aloxy and ($C_1$–$C_3$)alkoxycarbonyl;

$R_6$ represents ($C_1$–$C_{10}$)alkyl-heterocyclyl, ($C_1$–$C_{10}$)alkyl-($C_3$–$C_{12}$)cyclic hydrocarbon group, ($C_1$–$C_{10}$)alkyl, ($C_2$–$C_{10}$)olefinic group, ($C_3$–$C_{12}$)cyclic hydrocarbon group, heterocyclyl, ($C_2$–$C_{10}$)alkynyl, $Y_1R_{21}$, $Y_2R_{22}$ or $Y_4R_{24}$;

wherein the ($C_1$–$C_{10}$)alkyl, ($C_2$–$C_{10}$)olefinic group and ($C_3$–$C_{12}$)cyclic hydrocarbon group are substituted by one or more, same or different substituents represented by $R_7$, and wherein the ($C_1$–$C_{10}$)alkyl-heterocyclyl, ($C_1$–$C_{10}$)alkyl-($C_3$–$C_{12}$)cyclic hydrocarbon group, heterocyclyl and ($C_2$–$C_{10}$)alkynyl, are optionally substituted by one or more, same or different substituents represented by $R_7$;

$R_7$ represents $R_{12}$ Y—H or Y—$R_{14}$; wherein the $R_{12}$ and Y—$R_{14}$ group are optionally substituted by one or more, same or different substituents represented by $R_8$;

$R_8$ represents $R_{12}$, Y—H, Y—$R_{14}$ or $R_{14}$; wherein the $R_{12}$, Y—$R_{14}$ and $R_{14}$ group are optionally substituted by one or more, same or different substituents represented by $R_9$;

$R_9$ represents $R_{12}$, Y—H, Y—$R_{14}$ or $R_{14}$; wherein the $R_{12}$, Y—$R_{14}$ and $R_{14}$ group are optionally substituted by one or more, same or different substituents represented by $R_{10}$;

$R_{10}$ represents $R_{12}$, Y—H, Y—$R_{14}$ or $R_{14}$; wherein the $R_{12}$, Y—$R_{14}$ and $R_{14}$ group are optionally substituted by one or more, same or different substituents represented by $R_{11}$;

$R_{11}$ represents $R_{12}$ or $R_{14}$; wherein the $R_{12}$ and $R_{14}$ group are optionally substituted by one or more, same or different substituents represented by $R_{12}$;

$R_{12}$ represents halogen, hydroxy, mercapto, trifluoromethyl, amino, ($C_1$–$C_3$)alkoxy, ($C_1$–$C_3$)alkylthio, ($C_1$–$C_6$)alkylamino, ($C_1$–$C_3$)alkoxycarbonyl, ($C_1$–$C_9$)trialkylammonium in association with an anion, ($C_2$–$C_{10}$)dialkylphosphinoyl, ($C_1$–$C_5$)alkyl(hydroxy)phosphinoyl, ($C_2$–$C_{10}$)dialkylphosphinoyloxy, ($C_1$–$C_5$)alkyl(hydroxy)phosphinoyloxy, dihydroxyphosphinoyl, dihydroxyphosphinoyloxy, cyano, azido, nitro, —CHO, —COOH, —CONH$_2$, —CONHR' or —CONRR', wherein R and R' represent ($C_1$–$C_3$)alkyl;

Y represents —O—, —S—, —S(O)—, —S(O)$_2$—, —NR$_a$—, —NR$_a$C(Z)—, —NR$_a$C(Z)NR$_b$—, —NR$_a$C(Z)—, —C(Z)NR$_a$—, —C(O)—, —C(S)—, —C(Z)O—, —C(O)Z—, —C(S)S— —OC(Z)—, —NR$_a$C(Z)O—, —OC(Z)NR$_a$—, —S(O)$_2$O—, —OS(O)$_2$—, —S(O)$_2$NR$_a$—, —NR$_a$S(O)$_2$—, —OC(Z)O—, —OC(Z)Z—, —OP(O)(OR$_a$)O—, —P(O)(OR$_a$)O—, —C(NR$_a$)—, —C(NOR$_a$)—, —N=C(R$_a$)—, —N=C(OR$_a$)—, —N(OR$_a$)—, —ON(R$_a$)—, —N(R$_a$)O—, —N(R$_a$)C(=NR$_b$)NR$_c$—, —C(=NR$_a$)NR$_b$— or —N(R$_a$)C(=NR$_b$)—;

Z represents oxygen or sulphur;

$R_{14}$ represents ($C_1$–$C_6$)alkyl, ($C_2$–$C_6$)olefinic group, ($C_3$–$C_{12}$)cyclic hydrocarbon group, heterocyclyl or ($C_2$–$C_6$)alkynyl;

$Y_1$ represents —NR$_a$C(S)NR$_b$—, —C(O)—, —C(S)—, —C(S)O—, —C(O)S—, —C(S)S—, —OC(S)—, —OC(O)—, —NR$_a$C(S)O—, —OC(Z)NR$_a$—, —S(O)$_2$O—, —OS(O)$_2$—, —S(O)$_2$NR$_a$—, —NR$_a$S(O)$_2$—, —OC(Z)O—, —OC(Z)Z—, —OP(O)(OR$_a$)O—, —P(O)(OR$_a$)O—, —C(NR$_a$)—, —C(NOR$_a$)—, —N=C(R$_a$)—, —N=C(OR$_a$)—, —N(OR$_a$)—, —ON(R$_a$)—, —N(R$_a$)O—, N(R$_a$)C(=NR$_b$)NR$_c$—, —C(=NR$_a$)NR$_b$— or —N(R$_a$)C(=NR$_b$)—;

$R_{21}$ represents ($C_1$–$C_{10}$)alkyl-heterocyclyl, ($C_1$–$C_{10}$)alkyl-($C_3$–$C_{12}$)cyclic hydrocarbon group, ($C_1$–$C_{10}$)alkyl, ($C_2$–$C_{10}$)olefinic group, ($C_3$–$C_{12}$)cyclic hydrocarbon group, heterocyclyl or ($C_2$–$C_{10}$)alkynyl; any of which are optionally substituted by one or more, same or different substituents represented by $R_7$;

$Y_2$ represents —O—, —S—, —C(O)O— or —C(O)NR$_a$—;

$R_{22}$ represents ($C_1$–$C_{10}$)alkyl-heterocyclyl, ($C_1$–$C_{10}$)alkyl-($C_3$–$C_{12}$)cyclic hydrocarbon group, heterocyclyl, ($C_2$–$C_{10}$)alkynyl, ($C_1$–$C_{10}$)alkyl, ($C_2$–$C_{10}$)olefinic group or ($C_3$–$C_8$)monocyclic hydrocarbon group; wherein the ($C_1$–$C_{10}$)alkyl is substituted by one or more, same or different substituents represented by $R_7$ and wherein the ($C_1$–$C_{10}$)alkyl-heterocyclyl, ($C_1$–$C_{10}$)

alkyl-$(C_3-C_{12})$cyclic hydrocarbon group, heterocyclyl, $(C_2-C_{10})$alkynyl, $(C_2-C_{10})$olefinic group and $(C_3-C_{12})$ monocyclic hydrocarbon group are optionally substituted by one or more, same or different substituents represented by $R_7$;

$Y_4$ represents $-NR_aC(O)NR_bCH(R_c)-$, $-NR_aC(O)NR_bS(O)_2-$, $-NR_a-$, $-NR_aC(Z)-$, $-NR_aC(O)OCH(R_c)-$, $-NR_aC(O)NR_bC(R_d)(R_e)-OC(O)-$ or $-NR_aC(O)OC(R_d)(R_e)-OC(O)-$;

$R_{24}$ represents $(C_1-C_{10})$alkyl-heterocyclyl, $(C_1-C_{10})$alkyl-$(C_3-C_{12})$cyclic hydrocarbon group, heterocyclyl, $(C_2-C_{10})$alkynyl, $(C_1-C_{10})$alkyl, $(C_2-C_{10})$olefinic group or $(C_3-C_{12})$cyclic hydrocarbon group; wherein the $(C_1-C_{10})$alkyl, $(C_2-C_{10})$olefinic group and $(C_3-C_{12})$cyclic hydrocarbon group are substituted by one or more, same or different substituents represented by $R_{15}$, and wherein the $(C_1-C_{10})$alkyl, $(C_2-C_{10})$olefinic group, $(C_3-C_{12})$cyclic hydrocarbon group, $(C_1-C_{10})$alkyl-heterocyclyl, $(C_1-C_{10})$alkyl-$(C_3-C_{12})$cyclic hydrocarbon group, heterocyclyl and $(C_2-C_{10})$ alkynyl are optionally substituted by one or more, same or different substituents represented by $R_7$;

$R_{15}$ represents $R_{12a}$, $R_{12b}$ or $R_{12c}$; wherein $R_{12a}$, $R_{12b}$ and $R_{12c}$ are optionally substituted by one or more, same or different substituents represented by $R_7$;

$R_{12a}$ represents $(C_1-C_3)$alkoxy, $(C_1-C_3)$alkylthio, $(C_1-C_6)$alkylamino, $(C_1-C_3)$alkoxycarbonyl, $-CONHR'$ or $-CONRR'$ wherein R and R' represent $(C_1-C_3)$alkyl; any of which are substituted by one or more, same or different substituents represented by $R_{42}$; with the proviso that when $R_{12a}$ or $R_{15}$, including further substitution by $R_{42}$, represent groups of the formulas $-(Q-O)_n-Q$ or $-CH_2(Q-O)_n-Q$, wherein Q is a $(C_1-C_3)$alkyl and n is an integer larger than 1, then said groups comprise a continuous linear sequence of atoms with at least 16 atoms;

$R_{12b}$ represents $(C_4-C_{10})$alkoxy, $(C_4-C_{10})$alkylthio, $(C_7-C_{12})$alkylamino, $(C_4-C_{10})$alkoxycarbonyl, $-CONHR'$ or $-CONRR'$ wherein R and R' represent $(C_4-C_{10})$alkyl; any of which are optionally substituted by one or more, same or different substituents represented by $R_7$;

$R_{12c}$ represents $-Y_5(C_1-C_{10})$alkyl, $-Y$-aryl, $-Y$-heterocyclyl, $-Y-(C_3-C_{12})$cyclic hydrocarbon group and $-Y-(C_2-C_{10})$olefinic group; any of which are optionally substituted by one or more, same or different substituents represented by $R_7$;

$Y_5$ represents $-S(O)-$, $-S(O)_2-$, $-NR_aC(Z)-$, $-NR_aC(Z)NR_b-$, $-C(S)NR_a-$, $-C(O)-$, $-C(S)-$, $-C(S)O-$, $-C(O)S-$, $-C(S)S-$, $-OC(Z)-$, $-NR_aC(Z)O-$, $-OC(Z)NR_a-$, $-S(O)_2O-$, $-OS(O)_2-$, $-S(O)_2NR_a-$, $-NR_aS(O)_2-$, $-OC(Z)O-$, $-OC(Z)Z-$, $-OP(O)(OR_a)O-$, $P(O)(OR_a)O-$, $C(NR_a)-$, $-C(NOR_a)-$, $-N=C(R_a)-$, $-N=C(OR_a)-$, $-N(OR_a)-$, $-ON(R_a)-$, $N(R_a)O-$, $N(R_a)C(=NR_b)NR_c-$, $-C(=NR_a)NR_b-$ or $-N(R_a)C(=NR_b)-$;

$R_{42}$ represents $-Y-H$, $Y-R_{14}$, $R_{52}$, halogen, trifluoromethyl, cyano, azido or nitro; wherein $R_{52}$ and $-Y-R_{14}$ are optionally substituted by one or more, same or different substituents represented by $R_7$;

$R_{52}$ represents $(C_6-C_{10})$alkyl, $(C_2-C_6)$olefinic group, $(C_3-C_{12})$cyclic hydrocarbon group, heterocyclyl, $(C_2-C_6)$alkynyl or heteroaryl;

$R_a$, $R_b$, and $R_c$ represent independently hydrogen, $(C_1-C_6)$alkyl, $(C_2-C_6)$olefinic group, $(C_3-C_{12})$cyclic hydrocarbon group, aryl, heterocyclyl or $(C_2-C_6)$alkynyl; any of which are optionally substituted by one or more, same or different substituents represented by $R_{12}$;

$R_d$ and $R_e$ independently represent hydrogen, $(C_1-C_6)$alkyl, $(C_2-C_6)$olefinic group or $(C_3-C_{12})$cyclic hydrocarbon group; any of which are optionally substituted by one or more, same or different substituents represented by $R_{12}$;

and pharmaceutically acceptable salt, solvates and hydrates thereof, with the proviso that if; $R_1$ is methyl; $R_2$ is chloro; and $R_3$, $R_4$ and hydrogen; then $R_6$ cannot be trifluoromethyl, and with the proviso that if $R_6$ is $Y_4R_{24}$ is $-NR_aC(Z)$ with $R_a$ being hydrogen andZ being oxygen, then $R_{24}$ cannot be $-CF_3$.

2. A compound according to claim 1 wherein $R_6$ represents $(C_1-C_6)$alkyl-heterocyclyl, $(C_1-C_6)$alkyl-$(C_3-C_9)$cyclic hydrocarbon group, $(C_1-C_6)$alkyl, $(C_2-C_6)$olefinic group, $(C_3-C_6)$cyclic hydrocarbon group, heterocyclyl, $(C_2-C_6)$alkynyl, $Y_1R_{21}$, $Y_2R_{22}$ or $Y_4R_{24}$; wherein the $(C_1-C_6)$alkyl, $(C_2-C_6)$olefinic group and $(C_3-C_6)$cyclic hydrocarbon group are substituted by one or more, same or different substituents represented by $R_7$ and wherein the $(C_1-C_6)$alkyl-heterocyclyl, $(C_1-C_6)$alkyl-$(C_3-C_9)$cyclic hydrocarbon group heterocyclyl and $(C_2-C_6)$alkynyl are optionally substituted by one or more, same or different substituents represented by $R_7$;

$R_7$ represents $R_{12}$, $Y-H$ or $Y-R_{14}$; wherein the $R_{12}$ and $Y-R_{14}$ group are optionally substituted by one or more, same or different substituents represented by $R_8$;

$R_8$ represents $R_{12}$, $Y-H$, $Y-R_{14}$ or $R_{14}$; wherein the $R_{12}$, $Y-R_{14}$ and $R_{14}$ group are optionally substituted by one or more, same or different substituents represented by $R_9$;

$R_9$ represents $R_{12}$, $Y-H$, $Y-R_{14}$ or $R_{14}$; wherein the $R_{12}$, $Y-R_{14}$ and $R_{14}$ group are optionally substituted by one or more, same or different substituents represented by $R_{10}$;

$R_{10}$ represents $R_{12}$ or $R_{14}$; wherein the $R_{12}$ and $R_{14}$ group are optionally substituted by one or more, same or different substituents represented by $R_{12}$;

$R_{12}$ represents halogen, hydroxy, mercapto, trifluoromethyl, amino, $(C_1-C_3)$alkoxy, $(C_1-C_3)$alkylthio, $(C_1-C_6)$alkylamino, $(C_1-C_3)$alkoxycarbonyl, $(C_1-C_6)$trialkylammonium in association with an anion, $(C_2-C_6)$dialkylphosphinoyl, $(C_1-C_3)$alkyl(hydroxy)phosphinoyl, $(C_2-C_6)$dialkylphosphinoyloxy, $(C_1-C_3)$alkyl(hydroxy)phosphinoyloxy, dihydroxyphosphinoyl, dihydroxyphosphinoyloxy, cyano, azido, nitro, $-CHO$, $-COOH$, $-CONH_2$, $-CONHR'$, or $-CONRR'$; wherein R and R' represent $(C_1-C_3)$alkyl;

Y represents $-O-$, $-S-$, $-S(O)-$, $-S(O)_2-$, $-NR_a-$, $-NR_aC(Z)NR_b-$, $-NR_aC(Z)-$, $-C(Z)NR_a-$, $-C(O)-$, $-C(Z)O-$, $-OC(Z)13$, $-NR_aC(Z)O-$, $-OC(Z)NR_a-$, $-S(O)_2O-$, $-OS(O)_2-$, $-S(O)_2NR_a-$, $-NR_aS(O)_2-$, $-OC(Z)Z-$, $-OP(O)(OR_a)O-$, $-P(O)(OR_a)O-$, $-C(NOR_a)-$, $-N(OR_a)-$, $-ON(R_a)-$, $-N(R_a)O-$, $-N(R_a)C(=NR_b)NR_c-$, $-C(=NR_a)NR_b-$ or $-N(R_a)C(=NR_b)-$;

Z represents oxygen;

$R_{14}$ represents $(C_1-C_6)$alkyl, $(C_2-C_6)$olefinic group, $(C_3-C_9)$cyclic hydrocarbon group, heterocyclyl or $(C_2-C_6)$alkynyl;

$Y_1$ represents $-NR_aC(S)NR_b-$, $-C(O)-$, $-OC(O)-$, $-NR_aC(S)O-$, $-OC(Z)NR_a-$, $-S(O)_2NR_a-$, $-NR_aS(O)_2-$, $-OC(Z)O-$, $-C(NR_a)-$, —C(NOR$_a$)—, —N(OR$_a$)—, —ON(R$_a$)—, —N(R$_a$)O—, —N(R$_a$)C(=NR$_b$)NR$_c$—, —C(=NR$_a$)NR$_b$— or —N(R$_a$)C(=NR$_b$)—;

R$_{21}$ represents (C$_1$–C$_6$)alkyl-heterocyclyl, (C$_1$–C$_6$)alkyl-(C$_3$–C$_9$)cyclic hydrocarbon group, (C$_1$–C$_6$)alkyl, (C$_2$–C$_6$)olefinic group, (C$_3$–C$_9$)cyclic hydrocarbon group, heterocyclyl or (C$_2$–C$_6$)alkynyl; any of which are optionally substituted by one or more, same or different substituents represented by R$_7$;

Y$_2$ represents —O—, —S—, —C(O)O— or —C(O)NR$_a$—;

R$_{22}$ represents (C$_1$–C$_6$)alkyl-heterocyclyl, (C$_1$–C$_6$)alkyl-(C$_3$–C$_9$)cyclic hydrocarbon group, heterocyclyl, (C$_2$–C$_6$)alkynyl, (C$_1$–C$_6$)alkyl, (C$_2$–C$_6$)olefinic group or (C$_3$–C$_9$)monocyclic hydrocarbon group; wherein the (C$_1$–C$_6$)alkyl is substituted by one or more, same or different substituents represented by R$_7$ and wherein the (C$_1$–C$_6$)alkyl-heterocyclyl, (C$_1$–C$_6$)alkyl-(C$_3$–C$_9$)cyclic hydrocarbon group, heterocyclyl, (C$_2$–C$_6$)alkynyl, (C$_2$–C$_6$)olefinic group, and (C$_3$–C$_9$)monocyclic hydrocarbon group are optionally substituted by one or more, same or different substituents represented by R$_7$;

Y$_4$ represents —NR$_a$C(O)NR$_b$CH(R$_c$)—, —NR$_a$C(O)NR$_b$S(O)$_2$—, —NR$_a$—, —NR$_a$C(Z)—, —NR$_a$C(O)OCH(R$_c$)—, —NR$_a$C(O)NR$_b$C(R$_d$)(R$_e$)—OC(O)— or —NR$_a$C(O)OC(R$_d$)(R$_e$)—OC(O)—;

R$_{24}$ represents (C$_1$–C$_6$)alkyl-heterocyclyl, (C$_1$–C$_6$)alkyl-(C$_3$–C$_9$)cyclic hydrocarbon group, heterocyclyl, (C$_2$–C$_6$)alkynyl, (C$_1$–C$_6$)alkyl, (C$_2$–C$_6$)olefinic group or (C$_3$–C$_9$)cyclic hydrocarbon group; wherein the (C$_1$–C$_6$)alkyl, (C$_2$–C$_6$)olefinic group, and (C$_3$–C$_9$)cyclic hydrocarbon group are substituted by one or more, same or different substituents represented by R$_{15}$, and wherein the (C$_1$–C$_6$)alkyl, (C$_2$–C$_6$)olefinic group, (C$_3$–C$_9$)cyclic hydrocarbon group, (C$_1$–C$_6$)alkyl-heterocyclyl, (C$_1$–C$_6$)alkyl-(C$_3$–C$_9$)cyclic hydrocarbon group, heterocyclyl and (C$_2$–C$_6$)alkynyl are optionally substituted by one or more, same or different substituents represented by R$_7$;

R$_{15}$ represents R$_{12a}$, R$_{12b}$ or R$_{12c}$; wherein R$_{12a}$, R$_{12b}$ and R$_{12c}$ may be substituted by one or more, same or different substituents represented by R$_7$;

R$_{12a}$ represents (C$_1$–C$_3$)alkoxy, (C$_1$–C$_3$)alkylthio, (C$_1$–C$_6$)alkylamino, (C$_1$–C$_3$)alkoxycarbonyl, —CONHR' or —CONRR' wherein R and R' represent (C$_1$–C$_3$)alkyl; any of which are substituted by one or more, same or different substituents represented by R$_{42}$; with the proviso that when R$_{12a}$ or R$_{15}$, including further substitution by R$_{42}$, represent groups of the formulas —(Q—O)$_n$—Q or —CH$_2$(Q—O)$_n$—Q, wherein Q is a (C$_1$–C$_3$)alkyl and n is an integer larger than 1, then said groups comprise a continuous linear sequence of atoms with at least 16 atoms;

R$_{12b}$ represents (C$_4$–C$_6$)alkoxy, (C$_4$–C$_6$)alkylthio, (C$_7$–C$_{12}$)alkylamino, (C$_4$–C$_8$)alkoxycarbonyl, —CONHR' or —CONRR'; wherein R and R' represent (C$_4$–C$_8$)alkyl; any of which are optionally substituted by one or more, same or different substituents represented by R$_7$;

R$_{12c}$ represents —Y$_5$(C$_1$–C$_6$)alkyl, —Y-aryl, —Y-heterocyclyl, —Y—(C$_3$–C$_9$)cyclic hydrocarbon group and —Y—(C$_2$–C$_6$)olefinic group; any of which are optionally substituted by one or more, same or different substituents represented by R$_7$;

Y$_5$ represents —S(O)—, —S(O)$_2$—, —NR$_a$C(Z)—, —NR$_a$C(Z)NR$_b$—, —C(O)—, —OC(Z)—, —NR$_a$C(Z)O—, —OC(Z)NR$_a$—, —S(O)$_2$NR$_a$—, —NR$_a$S(O)$_2$—, —OC(Z)O—, —OP(O)(OR$_a$)O—, —P(O)(OR$_a$)O—, —C(NR$_a$)—, —C(NOR$_a$)—, —N(OR$_a$)—, —ON(R$_a$)—, —N(R$_a$)O—, N(R$_a$)C(=NR$_b$)NR$_c$—, —C(=NR$_a$)NR$_b$— or —N(R$_a$)c(=NR$_b$)—;

R$_{42}$ represents —Y—H, Y—R$_{14}$, R$_{52}$, halogen, trifluoromethyl, cyano, azido or nitro; wherein R$_{52}$ and —Y—R$_{14}$ are optionally substituted by one or more, same or different substituents represented by R$_8$;

R$_{52}$ represents (C$_6$–C$_8$)alkyl, (C$_2$–C$_4$)olefinic group, (C$_3$–C$_6$)cyclic hydrocarbon group, heterocyclyl, (C$_2$–C$_4$)alkynyl or heteroaryl;

R$_a$, R$_b$, and R$_c$ represent independently hydrogen, (C$_1$–C$_4$)alkyl, (C$_2$–C$_4$)olefinic group, (C$_3$–C$_9$)cyclic hydrocarbon group, aryl, heterocyclyl or (C$_2$–C$_4$)alkynyl; any of which are optionally substituted by one or more, same or different substituents represented by R$_{12}$;

R$_d$ and R$_e$ represent independently hydrogen, (C$_1$–C$_4$) alkyl, (C$_2$–C$_4$)olefinic group, and (C$_3$–C$_9$)cyclic hydrocarbon group; any of which are optionally substituted by one or more, same or different substituents represented by R$_{12}$.

3. A compound according to claim 1 wherein R$_1$ represents substituents selected from the group consisting of halogen, cyano, methyl and methoxy.

4. A compound according to claim 1 wherein R$_2$ represents one or more substituents independently selected from the group consisting of hydrogen, halogen, cyano, methyl and methoxy.

5. A compound according to claim 1 wherein R$_3$ represents one or more substituents independently selected from the group consisting of hydrogen, halogen, hydroxy, methyl, methoxy and cyano.

6. A compound according to claim 1 wherein R$_5$ represents one or more substituents independently selected from the group consisting of hydrogen, halogen, trifluoromethyl, methyl, ethyl and methoxy.

7. A compound according to claim 1 wherein R$_6$ represents (C$_1$–C$_4$)alkyl-heterocyclyl, (C$_1$–C$_4$)alkyl-(C$_3$–C$_6$)cyclic hydrocarbon group, (C$_1$–C$_6$)alkyl, (C$_2$–C$_4$)olefinic group, heterocyclyl, (C$_2$–C$_4$)alkynyl, Y$_1$R$_{21}$, Y$_2$R$_{22}$ or Y$_4$R$_{24}$; wherein the (C$_1$–C$_6$)alkyl and (C$_2$–C$_4$)olefinic group are substituted by one or more, same or different substituents represented by R$_7$, and wherein the (C$_1$–C$_4$)alkyl-heterocyclyl, (C$_1$–C$_4$)alkyl-(C$_3$–C$_6$)cyclic hydrocarbon group heterocyclyl and (C$_2$–C$_4$)alkynyl are optionally substituted by one or more, same or different substituents represented by R$_7$;

R$_7$ represents R$_{12}$, Y—H or Y—R$_{14}$; wherein the R$_{12}$ and Y—R$_{14}$ group are optionally further substituted by one or more, same or different substituents represented by R$_8$;

R$_8$ represents R$_{12}$, Y—H, Y—R$_{14}$ or R$_{14}$; wherein the R$_{12}$, Y—R$_{14}$ and R$_{14}$ group are optionally substituted by one or more, same or different substituents represented by R$_9$;

R$_9$ represents R$_{12}$, Y—R$_{14}$ or R$_{14}$; wherein the R$_{12}$, Y—R$_{14}$, and R$_{14}$ group are optionally substituted by one or more, same or different substituents represented by R$_{12}$;

R$_{12}$ represents halogen, hydroxy, trifluoromethyl, amino, (C$_1$–C$_3$)alkoxy, (C$_1$–C$_3$)alkylthio, (C$_1$–C$_6$)alkylamino, (C$_1$–C$_3$)alkoxycarbonyl, (C$_1$–C$_6$)trialkylammonium in association with an anion, (C$_2$–C$_6$)dialkylphosphinoyl, (C$_2$–C$_6$)dialkylphosphinoyloxy, dihydroxyphosphinoyl, dihydroxyphosphinoyloxy, cyano, —COOH, —CONH$_2$, —CONHR' or —CONRR'; wherein R and R' represent (C$_1$–C$_3$)alkyl;

Y represents —O—, —S—, —S(O)—, —S(O)$_2$—, —NR$_a$—, —NR$_a$C(Z)NR$_b$—, —NR$_a$C(Z)—, —C(Z)NR$_a$—, —C(O)—, —C(Z)O—, —OC(Z)—, —NR$_a$C(Z)O—, —OC(Z)NR$_a$—, —S(O)$_2$O—, —OS(O)$_2$—, —S(O)$_2$NR$_a$—, —NR$_a$S(O)$_2$—, —OC(Z)Z—, —N(R$_a$)C(=NR$_b$)NR$_c$—, —C(=NR$_a$)NR$_b$— or —N(R$_a$)C(=NR$_b$)—;

Z represents oxygen;

R$_{14}$ represents (C$_1$–C$_4$)alkyl, (C$_2$–C$_4$)olefinic group, (C$_3$–C$_6$)cyclic hydrocarbon group, heterocyclyl or (C$_2$–C$_3$)alkynyl;

Y$_1$ represents —NR$_a$C(S)NR$_b$—, —C(O)—, —OC(O)—, —NR$_a$C(S)O—, —OC(Z)NR$_a$—, —S(O)$_2$NR$_a$—, —NR$_a$S(O)$_2$— or —OC(Z)O—;

R$_{21}$ represents (C$_1$–C$_4$)alkyl-heterocyclyl, (C$_1$–C$_4$)alkyl-(C$_3$–C$_6$)cyclic hydrocarbon group, (C$_1$–C$_6$)alkyl, (C$_2$–C$_4$)olefinic group, (C$_3$–C$_6$)cyclic hydrocarbon group, heterocyclyl or (C$_2$–C$_6$)alkynyl; any of which substituted by one or more, same or different substituents represented by R$_7$;

Y$_2$ represents —O—, —S—, —C(O)O— or C(O)NR$_a$—;

R$_{22}$ represents (C$_1$–C$_4$)alkyl-heterocyclyl, (C$_1$–C$_4$)alkyl-(C$_3$–C$_6$)cyclic hydrocarbon group, heterocyclyl, (C$_2$–C$_4$)alkynyl, (C$_1$–C$_6$)alkyl, (C$_2$–C$_4$)olefinic group or (C$_3$–C$_6$)monocyclic hydrocarbon group; wherein the (C$_1$–C$_6$)alkyl is substituted by one or more, same or different substituents represented by R$_7$ and wherein the (C$_1$–C$_4$)alkyl-heterocyclyl, (C$_1$–C$_4$)alkyl-(C$_3$–C$_6$)cyclic hydrocarbon group, heterocyclyl, (C$_2$–C$_4$)alkynyl, (C$_2$–C$_4$)olefinic group and (C$_3$–C$_6$)monocyclic hydrocarbon group are optionally substituted by one or more, same or different substituents represented by R$_7$;

Y$_4$ represents —NR$_a$C(O)NR$_b$CH(R$_c$)—, —NR$_a$C(O)NR$_b$S(O)$_2$—, —NR$_a$—, —NR$_a$C(Z)—, —NR$_a$C(O)OCH(R$_c$)—, —NR$_a$C(O)NR$_b$C(R$_d$)(R$_e$)—OC(O)— or —NR$_a$C(O)OC(R$_d$)(R$_e$)—OC(O)—;

R$_{24}$ represents (C$_1$–C$_4$)alkyl-heterocyclyl, (C$_1$–C$_4$)alkyl-(C$_3$–C$_6$)cyclic hydrocarbon group, heterocyclyl, (C$_2$–C$_4$)alkynyl, (C$_1$–C$_6$)alkyl, (C$_2$–C$_4$)olefinic group or (C$_3$–C$_9$)cyclic hydrocarbon group; wherein the (C$_1$–C$_6$)alkyl, (C$_2$–C$_4$)olefinic group, and (C$_3$–C$_9$)cyclic hydrocarbon group are substituted by one or more, same or different substituents represented by R$_{15}$ and wherein the (C$_1$–C$_6$)alkyl, (C$_2$–C$_4$)olefinic group, (C$_3$–C$_9$)cyclic hydrocarbon group, (C$_1$–C$_4$)alkyl-heterocyclyl, (C$_1$–C$_4$)alkyl-(C$_3$–C$_6$)cyclic hydrocarbon group, heterocyclyl and (C$_2$–C$_4$)alkynyl are optionally substituted by one or more, same or different substituents represented by R$_7$;

R$_{15}$ represents R$_{12a}$, R$_{12b}$ or R$_{12c}$; wherein R$_{12a}$, R$_{12b}$ and R$_{12c}$ are optionally substituted by one or more, same or different substituents represented by R$_7$;

R$_{12a}$ represents (C$_1$–C$_3$)alkoxy, (C$_1$–C$_3$)alkylthio, (C$_1$–C$_6$)alkylamino, (C$_1$–C$_3$)alkoxycarbonyl, —CONHR' or —CONRR' wherein R and R' represent (C$_1$–C$_3$)alkyl; any of which are substituted by one or more, same or different substituents represented by R$_{42}$; with the proviso that when R$_{12a}$ or R$_{15}$, including further substitution by R$_{42}$, represent groups of the formulas —(Q—O)$_n$—Q or —CH$_2$(Q—O)$_n$—Q, wherein Q is a (C$_1$–C$_3$)alkyl and n is an integer larger than 1, then said groups comprise a continuous linear sequence of atoms with at least 16 atoms;

R$_{12b}$ represents (C$_4$–C$_6$)alkoxy, (C$_4$–C$_6$)alkylthio, (C$_7$–C$_{12}$)alkylamino, (C$_4$–C$_8$)alkoxycarbonyl, —CONHR' or —CONRR' wherein R and R' represent (C$_4$–C$_8$)alkyl; any of which are optionally substituted by one or more, same or different substituents represented by R$_7$;

R$_{12c}$ represents —Y$_5$(C$_1$–C$_6$)alkyl, —Y-aryl, —Y-heterocyclyl, —Y—(C$_3$–C$_9$)cyclic hydrocarbon group and —Y—(C$_2$–C$_6$)olefinic group; any of which are optionally substituted by one or more, same or different substituents represented by R$_7$;

Y$_5$ represents —S(O)—, —S(O)$_2$—, —NR$_a$C(Z)—, —NR$_a$C(Z)NR$_b$—, —C(O)—, —OC(Z)—, —NR$_a$C(Z)O—, —OC(Z)NR$_a$—, —S(O)$_2$NR$_a$—, —NR$_a$S(O)$_2$ or —OC(Z)O—;

R$_{42}$ represents —Y—H, Y—R$_{14}$, R$_{52}$, halogen, trifluoromethyl, cyano, azido or nitro; wherein R$_{52}$ and —Y—R$_{14}$ are optionally substituted by one or more, same or different substituents represented by R$_8$;

R$_{52}$ represents (C$_6$–C$_6$)alkyl, (C$_2$–C$_4$)olefinic group, (C$_3$–C$_6$)cyclic hydrocarbon group, heterocyclyl, (C$_2$–C$_4$)alkynyl or heteroaryl; R$_a$, R$_b$ and R$_c$ represent independently hydrogen, (C$_1$–C$_2$)alkyl, (C$_2$–C$_3$)olefinic group or (C$_2$–C$_3$)alkynyl; any of which are optionally substituted by one or more, same or different substituents represented by R$_{12}$;

R$_d$ and R$_e$ represent independently hydrogen or (C$_1$–C$_2$) alkyl.

8. A compound according to claim 1, wherein, R$_1$ represents substituents selected from the group consisting of halogen, cyano, methyl and methoxy;

R$_2$ represents one or more substituents independently selected from the group consisting of hydrogen, halogen, cyano, methyl and methoxy;

R$_3$ represents one or more substituents independently selected from the group consisting of hydrogen, halogen, hydroxy, methyl, methoxy and cyano;

R$_4$ represents hydrogen, methyl or ethyl;

R$_5$ represents one or more substituents independently selected from the group consisting of hydrogen, halogen, hydroxy, trifluoromethyl, methyl, ethyl and methoxy;

and X represents O.

9. A compound according to claim 1 wherein the molecular weight of said compound is below about 1500 Da.

10. A compound according to claim 1 wherein the molecular weight of said compound is below about 1200 Da.

11. A compound according to claim 1 wherein the molecular weight of said compound is below about 800 Da.

12. A compound according to claim 1 selected from the group consisting of
[2-Chloro-4-({2-[2-(tetrahydro-2H-pyran-2-yloxy)ethyl]phenyl}amino)phenyl](2-methylphenyl)methanone;
(2-Chloro-4-{[2-(2-hydroxyethyl)phenyl]amino}phenyl)(2-methylphenyl)methanone;
2-(2-{[3-Chloro-4-(2-methylbenzoyl)phenyl]amino}phenyl)ethyl acetate;
4-(2-{2-[(3-Chloro-4-(2-methylbenzoyl)phenyl)amino]phenyl}ethoxy)-4-oxobutanoic acid;
2-(2-{[3-Chloro-4-(2-methylbenzoyl)phenyl]amino}phenyl)ethyl hexanoate;
2-(2-{[3-Chloro-4-(2-methylbenzoyl)phenyl]amino}phenyl)-1-methylethyl acetate;
(2-Chloro-4-{[2-(2-hydroxypropyl)phenyl]amino}phenyl)(2-methylphenyl)methanone;
[2-Chloro-4-({2-[(1E)-3-hydroxyprop-1-enyl]phenyl}amino)phenyl](2-methylphenyl)methanone;

(2-Chloro-4-{[2-(3-hydroxypropyl)phenyl]amino}phenyl)(2-methylphenyl)methanone;
[2-Chloro-4-({2-[(1E)-4-hydroxybut-1-enyl]phenyl}amino)phenyl](2-methylphenyl)methanone;
[4-({2-[(1E)-3-aminoprop-1-enyl]phenyl}amino)-2-chlorophenyl](2-methylphenyl)methanone;
Diethyl (2E)-3-(2-{[3-chloro-4-(2-methylbenzoyl)phenyl]amino}phenyl)prop-2-enylphosphonate;
[2-Chloro-4-({2-[(1E)-3-hydroxy-3-methylbut-1-enyl]phenyl}amino)phenyl](2-methylphenyl)methanone;
Ethyl (2E)-3-(2-{[3-chloro-4-(2-methylbenzoyl)phenyl]amino}phenyl)acrylate;
(2E)-3-(2-{[3-chloro-4-(2-methylbenzoyl)phenyl]amino}phenyl)acrylic acid;
{2-Chloro-4-[(2-{(1E)-3-[(2,2-dimethyl-1,3-dioxolan-4-yl)methoxy]prop-1-enyl}phenyl)amino]phenyl}(2-methylphenyl)methanone;
[2-Chloro-4-({2-[(1E)-3-(2,3-dihydroxypropoxy)prop-1-enyl]phenyl}amino)phenyl](2-methylphenyl)methanone;
Tert-butyl (1R)-3-{[(2E)-3-(2-{[3-chloro-4-(2-methylbenzoyl)phenyl]amino}phenyl)prop-2-enyl]amino}-1-(hydroxymethyl)-2-oxoethylylcarbamate;
Methyl O-(tert-butyl)-N-({[(2E)-3-(2-{[3-chloro-4-(2-methylbenzoyl)phenyl]amino}phenyl)prop-2-enyl]amino}carbonyl)-L-serinate;
N-(tert-butyl)-N'-[(2E)-3-(2-{[3-chloro-4-(2-methylbenzoyl)phenyl]amino}phenyl)prop-2-enyl]thiourea;
N-[(2E)-3-(2-{[3-chloro-4-(2-methylbenzoyl)phenyl]amino}phenyl)prop-2-enyl]-4-oxopentanamide;
N-[(2E)-3-(2-{[3-chloro-4-(2-methylbenzoyl)phenyl]amino}phenyl)prop-2-enyl]-N'-ethylurea;
Ethyl 4-{[(2E)-3-(2-{[3-chloro-4-(2-methylbenzoyl)phenyl]amino}phenyl)prop-2-enyl]amino}-4-oxobutanoate;
N-[(2E)-3-(2-{[3-chloro-4-(2-methylbenzoyl)phenyl]amino}phenyl)prop-2-enyl]N'-cyclohexylurea; N'-[(2E)-3-(2-{[3-chloro-4-(2-methylbenzoyl)phenyl]amino}phenyl)prop-2-enyl]-N,N-dimethylsuccinamide;
Dimethyl [(2E)-3-(2-{[3-chloro-4-(2-methylbenzoyl)phenyl]amino}phenyl)prop-2-enyl]malonate;
[2-Chloro-4-({2-[(1E)-3-morpholin-4-ylprop-1-enyl]phenyl}amino)phenyl](2-methylphenyl)methanone;
6-O-[(2E)-3-(2-{[3-chloro-4-(2-methylbenzoyl)phenyl]amino}phenyl)prop-2-enyl]-1,2:3,4-di-O-(1-methylethylidene)-α-D-galactopyranose;
Methyl 5-O-[(2E)-3-(2-{[3-chloro-4-(2-methylbenzoyl)phenyl]amino}phenyl)prop-2-enyl]-2,3-O-(1-methylethylidene)-β-D-ribofuranoside;
Methyl 5-O-[(2E)-3-(2-{[3-chloro-4-(2-methylbenzoyl)phenyl]amino}phenyl)prop-2-enyl]-β-D-ribofuranoside;
Methyl (4E)-5-(2-{[3-chloro-4-(2-methylbenzoyl)phenyl]amino}phenyl)-2-(methylsulfonyl)pent-4-enoate;
Ethyl {[(2E)-3-(2-{[3-chloro-4-(2-methylbenzoyl)phenyl]amino}phenyl)prop-2-enyl]thio}acetate;
[2-Chloro-4-{[2-((1E)-3-{bis[2-(acetyloxy)ethyl]amino}prop-1-enyl)phenyl]amino}phenyl](2-methylphenyl)methanone;
[2-Chloro-4-{[2-((1E)-3-{bis[2-(hydroxy)ethyl]amino}prop-1-enyl)phenyl]amino}phenyl](2-methylphenyl)methanone;
(2-Chloro-4-{[2-((1E)-3-{4-[2-(acetyloxy)ethyl]piperidin-1-yl}prop-1-enyl)phenyl]amino}phenyl)(2-methylphenyl)methanone;
{2-chloro-4-[(2-{(1E)-3-[4-(2-hydroxyethyl)piperidin-1-yl]prop-1-enyl}phenyl)amino]phenyl}(2-methylphenyl)methanone;
{2-Chloro-4-[(2-{2-[(tetrahydrofuran-2-ylmethyl)amino]ethyl}phenyl)amino]phenyl}(2-methylphenyl)methanone;
[2-Chloro-4-({2-[2-(4-methylpiperazin-1-yl)ethyl]phenyl}amino)phenyl](2-methylphenyl)methanone;
{2-Chloro-4-[(2-{2-[(3-morpholin-4-ylpropyl)amino]ethyl}phenyl)amino]phenyl}(2-methylphenyl)methanone;
(2-Chloro-4-{[2-(2-{[2-(dimethylamino)ethyl]amino}ethyl)phenyl]amino}phenyl)(2-methylphenyl)methanone;
{2-Chloro-4-[(2-{2-[(2-methoxyethyl)amino]ethyl}phenyl)amino]phenyl}(2-methylphenyl)methanone;
1-[3-({2-[2-({3-Chloro-4-[(2-methylphenyl)carbonyl]phenyl}amino)phenyl]ethyl}amino)propyl]pyrrolidin-2-one;
{2-Chloro-4-[(2-{2-[methyl(tetrahydrofuran-2-ylmethyl)amino]ethyl}phenyl)amino]phenyl}(2-methylphenyl)methanone;
(2-Chloro-4-{[2-(2-{[(2,2-dimethyl-1,3-dioxolan-4-yl)methyl]amino}ethyl)phenyl]amino}phenyl)(2-methylphenyl)methanone;
{2-Chloro-4-[(2-{2-[4-(2-methoxyethyl)piperazin-1-yl]ethyl}phenyl)amino]phenyl}(2-methylphenyl)methanone;
(2-Chloro-4-{[2-(2-morpholin-4-ylethyl)phenyl]amino}phenyl)(2-methylphenyl)methanone;
{2-Chloro-4-[(2-{2-[(2,3-dihydroxypropyl)amino]ethyl}phenyl)amino]phenyl}(2-methylphenyl)methanone;
(4-{[2-(Aminomethyl)phenyl]amino}-2-chlorophenyl)(2-methylphenyl)methanone;
(2-Chloro-4-{[2-({2-[2-(tetrahydro-2H-pyran-2-yloxy)ethoxy]ethoxy}methyl) phenyl]amino}phenyl) (2-methyl phenyl) methanone;
{2-Chloro-4-[(2-{[(tetrahydro-2H-pyran-2-yloxy)ethoxy]methyl}phenyl)amino]phenyl}(2-methylphenyl)methanone;
[2-Chloro-4-({2-[(2-{2-[2-(tetrahydro-2H-pyran-2-yloxy)ethoxy]ethoxy}ethoxy)methyl]phenyl}amino)phenyl](2-methylphenyl)methanone;
[2-Chloro-4-({2-[(3,3,3-trifluoropropoxy)methyl]phenyl}amino)phenyl](2-methylphenyl)methanone;
Diethyl 2-({3-chloro-4-[(2-methylphenyl)carbonyl]phenyl}amino)benzylphosphonate;
2-[2-({3-Chloro-4-[(2-methylphenyl)carbonyl]phenyl}amino)benzyl]-1H-isoindole-1,3(2H)-dione;
{2-Chloro-4-[(2-{[2-(2-hydroxyethoxy)ethoxy]methyl}phenyl)amino]phenyl}(2-methylphenyl)methanone;
[2-Chloro-4-({2-[(hydroxyethoxy)methyl]phenyl}amino)phenyl](2-methylphenyl)methanone;
(2-Chloro-4-{[2-({2-[2-(2-hydroxyethoxy)ethoxy]ethoxy}methyl)phenyl]amino}phenyl)(2-methylphenyl)methanone;
[4-({4-Bromo-2-[(2-hydroxyethoxy)methyl]phenyl}amino)-2-chlorophenyl](2-methylphenyl)methanone;
(4-{[4-Bromo-2-({2-[2-(2-hydroxyethoxy)ethoxy]ethoxy}methyl)phenyl]amino}-2-chlorophenyl)(2-methylphenyl)methanone;
{4-[(4-Bromo-2-{[2-(2-hydroxyethoxy)ethoxy]methyl}phenyl)amino]-2-chlorophenyl}(2-methylphenyl)methanone; Diethyl 5-bromo-2-({3-chloro-4-[(2-methylphenyl)carbonyl]phenyl}amino) benzylphosphonate;
[4-({4-Bromo-2-[(3,3,3-trifluoropropoxy)methyl]phenyl}amino)-2-chlorophenyl](2-methylphenyl)methanone;
2-{[2-({3-Chloro-4-[(2-methylphenyl)carbonyl]phenyl}amino)benzyl]oxy}ethyl 4-methylbenzenesulfonate;
2-{[5-Bromo-2-({3-chloro-4-[(2-methylphenyl)carbonyl]phenyl}amino)benzyl]oxy}ethyl 4-methylbenzenesulfonate;
2-(2-{[5-Bromo-2-({3-chloro-4-[(2-methylphenyl)carbonyl]phenyl}amino) benzyl]oxy}ethoxy)ethyl 4-methylbenzenesulfonate;
2-[2-(2-{[5-Bromo-2-({3-chloro-4-[(2-methylphenyl)carbonyl]phenyl}amino)benzyl]oxy}ethoxy)ethoxy]ethyl 4-methylbenzenesulfonate;
[4-({4-Bromo-2-[(2-iodoethoxy)methyl]phenyl}amino)-2-chlorophenyl](2-methylphenyl)methanone;
{4-[(4-Bromo-2-{[2-(2-iodoethoxy)ethoxy]methyl}phenyl)amino]-2-chlorophenyl}(2-methylphenyl)methanone;
(4-{[4-Bromo-2-({2-[2-(2-iodoethoxy)ethoxy]ethoxy}methyl)phenyl]amino}-2-chlorophenyl)(2-methylphenyl)methanone;
[2-Chloro-4-({2-[(2-iodoethoxy)methyl]phenyl}amino) phenyl](2-methylphenyl)methanone;
Diethyl 2-{[2-({3-chloro-4-[(2-methylphenyl)carbonyl]phenyl}amino)benzyl]oxy}ethylphosphonate;
Diethyl 2-{[5-bromo-2-({3-chloro-4-[(2-methylphenyl)carbonyl]phenyl}amino) benzyl]oxy}ethylphosphonate;
Diethyl 2-({[5-bromo-2-({3-chloro-4-[(2-methylphenyl)carbonyl]phenyl}amino) benzyl]oxy}ethoxy)ethylphosphonate;
Diethyl 2-[2-(2-{[5-bromo-2-({3-chloro-4-[(2-methylphenyl)carbonyl]phenyl}amino)benzyl]oxy}ethoxy)ethoxy]ethylphosphonate;
Diethyl 2-{[2-({3-chloro-4-[(2-methylphenyl)carbonyl]phenyl}amino)benzyl]amino}-2-oxoethylphosphonate;
Diethyl 2-{[5-bromo-2-({3-chloro-4-[(2-methylphenyl)carbonyl]phenyl}amino)phenyl]amino}-2-oxoethylphosphonate;
{[2-({5-Bromo-3-Chloro-4-[(2-methylphenyl)carbonyl]phenyl}amino)benzyl]oxy}ethyl (diethoxyphosphoryl)acetate;
2-({3-Chloro-4-[(2-methylphenyl)carbonyl]phenyl}amino)benzylphosphonic acid;
N-[2-({3-Chloro-4-[(2-methylphenyl)carbonyl]phenyl}amino)benzyl]-2,2,2-trifluoroethanesulfonamide;
N-[5-Bromo-2-({3-chloro-4-[(2-methylphenyl)carbonyl]phenyl}amino)phenyl]-2,2,2-trifluoroethanesulfonamide;
{2-Chloro-4-[(2-{[((tetrahydro-2H-pyran-2-yloxy)propoxy]methyl}phenyl)amino]phenyl}(2-methylphenyl)methanone;
[2-Chloro-4-({2-[(hydroxypropoxy)methyl]phenyl}amino)phenyl](2-methylphenyl)methanone;
Diethyl 3-{[2-({3-chloro-4-[(2-methylphenyl)carbonyl]phenyl}amino) benzyl]oxy}propylphosphonate;
Diethyl 2-[2-({3-chloro-4-[(2-methylphenyl)carbonyl]phenyl}amino) phenyl]ethylphosphonate;
Diethyl 2-[5-bromo-2-({3-chloro-4-[(2-methylphenyl)carbonyl]phenyl}amino)phenyl]ethylphosphonate;
2-{[2-({3-Chloro-4-[(2-methylphenyl)carbonyl]phenyl}amino) benzyl]amino}-2-oxoethylphosphonic acid;
(2-{[3-Chloro-4-(2-methylbenzoyl)phenyl]amino}phenyl)-carbamic acid phenethyl ester;
N-(2-{[3-Chloro-4-(2-methylbenzoyl)phenyl]amino}phenyl)-2-phenoxy-acetamide;
N-(2-{[3-Chloro-4-(2-methylbenzoyl)phenyl]amino}phenyl)-3-phenoxy-propionamide;
N-(2-{[3-Chloro-4-(2-methylbenzoyl)phenyl]amino}phenyl)-2-(1,3-dioxo-1,3-dihydro-isoindole-2-yl)-acetamide;
N-(2-{[3-Chloro-4-(2-methylbenzoyl)phenyl]amino}phenyl)-succinamic acid 2-(2-methoxy-ethoxy)ethyl ester;
N-(2-{[3-Chloro-4-(2-methylbenzoyl)phenyl]amino}phenyl)-benzenesulfonamide;
Acetic acid (2-{[3-chloro-4-(2-methylbenzoyl)phenyl]amino}phenylcarbamoyl)-methyl ester;
1-(2-{[3-Chloro-4-(2-methylbenzoyl)phenyl]amino}phenyl)pyrrolidine-2,5-dione;
2-(2-{[3-Chloro-4-(2-methylbenzoyl)phenyl]amino}phenyl)ethyl propionate;
2,2-Dimethyl-propionic acid 2-(2-{[3-chloro-4-(2-methylbenzoyl)phenyl]amino}phenyl)ethyl ester;
[2-Chloro-4-({2-[3-(tetrahydro-2H-pyran-2-yloxy)propoxy]phenyl}amino) phenyl](2-methylphenyl)methanone;
(2-Chloro-4-{[2-(3-hydroxypropoxy)phenyl]amino}phenyl)(2-methylphenyl)methanone;
tert-Butyl 2-(2-{[3-chloro-4-(2-methylbenzoyl)phenyl]amino}phenyl)ethyl carbonate;
2-({[(5-Bromo-2-{[3-chloro-4-(2-methylbenzoyl)phenyl]amino}phenyl)amino]carbonyl}amino)ethyl 2-methylacrylate;
(4-{[4-Bromo-2-(2-hydroxyethyl)phenyl]amino}-2-chloro-phenyl)(2-methylphenyl)methanone;
3-(2-{[3-Chloro-4-(2-methylbenzoyl)phenyl]amino}phenoxy)propyl acetate;
[2-Chloro-4-({2-[3-(morpholin-4-yl)propoxy]phenyl}amino)phenyl](2-methylphenyl)methanone;
N-(2-{[3-Chloro-4-(2-methylbenzoyl)phenyl]amino}phenyl)-N'-(4-phenoxybutyl)succinamide;
N-(2-{[3-Chloro-4-(2-methylbenzoyl)phenyl]amino}phenyl)-N'-(6-hydroxyhexyl)succinamide;
N-(2-{[3-Chloro-4-(2-methylbenzoyl)phenyl]amino}phenyl)-N'-(2,3-dihydroxyproyl)succinamide;
tert-Butyl (1R)-3-(2-{[3-chloro-4-(2-methylbenzoyl)phenyl]amino}phenyl)-1-(hydroxymethyl)propylcarbamate;
Diethyl 6-[3-(2-{[3-chloro-4-(2-methylbenzoyl)phenyl]amino}phenylcarbamoyl)propionylamino]-hexyl phosphate;
Ethyl N-({[(2E)-3-(2-{[3-chloro-4-(2-methylbenzoyl)phenyl]amino} phenyl)prop-2-enyl]amino}carbonyl)glycinate;
tert-Butyl 2-(2-{[3-chloro-4-(2-methylbenzoyl)phenyl]amino}phenyl) ethyl(methyl)carbamate;
N-(5-Bromo-2-{[3-chloro-4-(2-methylbenzoyl)phenyl]amino}phenyl) —N'-(6-hydroxyhexyl)succinamide;
N-(5-Bromo-2-{[3-chloro-4-(2-methylbenzoyl)phenyl]amino}phenyl)-N'-(2,3-dihydroxyproyl)succinamide;
(2Z)-N-[(2E)-3-(2-{[3-chloro-4-(2-methylbenzoyl)phenyl]amino}phenyl)prop-2-enyl]-2-(2,5-dioxoimidazolidin-4-ylidene)acetamide;
(2-Chloro-4-{[2-(difluoromethyl)phenyl]amino}phenyl)(2-methylphenyl)methanone;

3-{[2-({3-Chloro-4-[(2-methylphenyl)carbonyl]phenyl}amino) phenyl]ethyl}-1-methylimidazolidine-2,4-dione;
3-{[2-({3-Chloro-4-[(2-methylphenyl)carbonyl]phenyl}amino) phenyl]ethyl}-5,5-dimethyloxazoline-2,4-dione;
4-{[2-({3-Chloro-4-[(2-methylphenyl)carbonyl]phenyl}amino) phenyl]ethyl}morpholine-3,5-dione;
1-{[2-({3-Chloro-4-[(2-methylphenyl)carbonyl]phenyl}amino) phenyl]ethyl}piperidine-2,6-dione;
4-(2-{[5-Bromo-2-({3-chloro-4-[(2-methylphenyl)carbonyl]phenyl}amino)benzyl]oxy}ethyl)morpholine-3,5-dione;
1-(2-{[5-Bromo-2-({3-chloro-4-[(2-methylphenyl)carbonyl]phenyl}amino)benzyl]oxy}ethyl)pyrrolidine-2,5-dione;
Ethyl 2-[3-(2-{5-bromo-[2-({3-chloro-4-[(2-methylphenyl) carbonyl]phenyl}amino)bezyloxy}ethyl)-2,4,5-trioxoimidazolidin-1-yl]acetate;
3-(2-{[5-Bromo-2-({3-chloro-4-[(2-methylphenyl)carbonyl]phenyl}amino)benzyl]oxy}ethyl)imidazolidine-2,4-dione;
1-(2-{[5-Bromo-2-({3-chloro-4-[(2-methylphenyl)carbonyl]phenyl}amino)benzyl]oxy}ethyl)-3,4-cis-diacetoxypyrrolidine-2,5-dione;
3-(2-{[5-Bromo-2-({3-chloro-4-[(2-methylphenyl)carbonyl]phenyl}amino)benzyl]oxy}ethyl)thiazoline-2,4-dione;
3-(2-{[5-Bromo-2-({3-chloro-4-[(2-methylphenyl)carbonyl]phenyl}amino)benzyl]oxy}ethyl)-1-methylimidazolidine-2,4-dione;
1-(2-{[5-Bromo-2-({3-chloro-4-[(2-methylphenyl)carbonyl]phenyl}amino)benzyl]oxy}ethyl)imidazolidine-2,4,5-trione;
(2-Chloro-4-{[(2-hydroxymethyl)phenyl]amino}phenyl)(2-methyl phenyl)methanone;
2-{[3-Chloro-4-(2-methylbenzoyl)phenyl]amino}benzyl acetate; and pharmaceutically acceptable salts, solvates and hydrates thereof.

13. A pharmaceutical composition comprising a compound according to claim 1, optionally together with a pharmaceutical acceptable excipient and optionally another pharmaceutically active ingredient selected from the group consisting of glucocorticoids, vitamin D analogues, anti-histamines, platelet activating factor (PAF) antagonists, anticolergenic agents, methyl xanthines, β-adregenic agents, COX-2 inhibitors, salicylates, indomethacin, flufenamate, naproxen, timegadine, gold salts, peniciliamine, serum cholesterol reducing agents, retinoids, zinc salts and salicylazosulfapyridin.

14. A pharmaceutical composition according to claim 13 wherein said composition comprises 0.1% to 100% of a compound of formula I.

15. A pharmaceutical composition according to claim 13 in dosage unit form comprising between 0.07 mg and 1 g of a compound of formula I.

16. A method for treatment or profylaxis of asthma, allergy, arthritis, rheumatoid arthritis, gout, atherosclerosis, chronic inflammatory bowel disease (Crohn's disease), proliferative and inflammatory skin disorders, psoriasis, atopic dermatitis, uveitis, septic shock, AIDS, osteroporosis and acne comprising administering to a patient in need thereof an effective amount of a compound according to any claims 1, optionally together with a pharmaceutically acceptable excipient, and optionally together with another pharmaceutically active ingredient selected from the group consisting of glucocorticoids, vitamin D analogues, anti-histamines, platelet activating factor (PAF) antagonists, anticolergenic agents, methyl xanthines, β-adregenic, COX-2 inhibitors, salicylates, indomethacin, flufenamate, naproxen, timegadine, gold salts, peniciliamine, serum cholesterol reducing agents, retinoids, zinc salts and salicylazosulfapyridin.

17. A compounds selected from the list consisting of
2-(2-Bromophenyl)-1-methylethyl acetate;
(3E)-2-Methyl-4-(tributylstannyl)but-3-en-2-ol;
Tributyl{(1E)-3-[(2,2-dimethyl-1,3-dioxolan-4-yl)methoxy]prop-1-enyl}stannane;
Dimethyl [(2E)-3-(tributylstannyl)prop-1-enyl]malonate;
4-[(2E)-3-(tributylstannyl)prop-2-enyl]morpholine;
1,2:3,4-di-O-(1-methylethylidene)-6-O-[(2E)-3-(tributylstannyl)prop-2-enyl]-α-D-galactopyranose;
Methyl 2,3-O-(1-methylethylidene)-5-O-[(2E)-3-(tributylstannyl)prop-2-enyl]-β-D-ribofuranoside;
Methyl (4E)-2-(methylsulfonyl)-5-(tributylstannyl)pent-4-enoate;
Ethyl {[(2E)-3-(tributylstannyl)prop-2-enyl]thio}acetate;
Tributyl{(1E)-3-[bis(2-hydroxyethyl)amino]prop-1-enyl}stannane;
Tributyl((1E)-3-{bis[2-(acetyloxy)ethyl]amino}prop-1-enyl)stannane;
Tributyl{(1E)-3-[4-(2-hydroxyethyl)piperidin-1-yl]prop-1-enyl}stannane;
Tributyl((1E)-3-{4-[2-(acetyloxy)ethyl]piperidin-1-yl}prop-1-enyl)stannane;
2-(2-{(2-Bromobenzyl)oxy}ethoxy)ethanol;
2-(2-{2-[(2-Bromobenzyl)oxy]ethoxy}ethoxy)ethanol;
2-Bromobenzyl 3,3,3-trifluoropropyl ether;
2-(2-{2-[(2-Bromobenzyl)oxy]ethoxy}ethoxy)tetrahydro-2H-pyran;
2-[2-(2-{2-[(2-Bromobenzyl)oxy]ethoxy}ethoxy)ethoxy]tetrahydro-2H-pyran;
2-{2-[(2-Bromobenzyl)oxy]ethoxy}tetrahydro-2H-pyran;
2-{3-[(2-Bromobenzyl)oxy]propoxy}tetrahydro-2H-pyran;
3-[(2-Bromobenzyl)oxy]propyl 4-methylbenzenesulfonate;
1-Bromo-2-(3-iodo-propoxymethyl)benzene;
Diethyl 3-[(2-bromobenzyl)oxy]propylphosphonate;
Diethyl 2-(2-bromophenyl)ethylphosphonate;
(2-Chloro-4-iodophenyl)(2-methylphenyl)methanone;
tert-Butyl (4R)-4-[2-(2-aminophenyl)ethyl]-2,2-dimethyl-1,3-oxazolidine-3-carboxylate;
tert-Butyl (4R)-4-[2-(2-{[3-chloro-4-(2-methylbenzoyl)phenyl]amino}phenyl)ethyl]-2,2-dimethyl-oxazolidine-3-carboxylate;
tert-Butyl [2-(2-bromophenyl)ethyl](methyl)carbamate;
3-[2-(2-Bromophenyl)ethyl]-1-methylimidazolidine-2,4-dione;
3-[2-(2-Bromophenyl)ethyl]-5,5-dimethyloxazolidine-2,4-dione;
4-[2-(2-Bromophenyl)ethyl]morpholine-3,5-dione;
1-[2-(2-Bromophenyl)ethyl]piperidine-2,6-dione; 2-Bromobenzyl (triisopropyl)silyl ether;
{2-Chloro-4-[(2-{[(triisopropyl)siloxy]methyl}phenyl)amino]phenyl}(2-methylphenyl)methanone.

18. A compound according to claim 1 wherein $R_2$ is in an ortho position with respect to C=X if $R_2$ is other than hydrogen.

19. A compound according to claim 1 wherein $R_1$ is selected from the group consisting of methyl, chloro and methoxy.

20. A compound according to claim 1 wherein $R_2$ is selected from the group consisting of hydrogen, methyl, chloro and methoxy.

21. A compound according to claim 19 wherein $R_2$ is selected from the group consisting of hydrogen, methyl, chloro and methoxy.

22. A compound according to claim 1 wherein $R_1$ is selected from the group consisting of methyl, chloro and methoxy; $R_2$ is selected from the group consisting of hydrogen, methyl, chloro and methoxy; and wherein $R_2$ is in an ortho position with respect to C=X if $R_2$ is other than hydrogen.

* * * * *